(12) United States Patent
Stranix et al.

(10) Patent No.: US 6,632,816 B1
(45) Date of Patent: Oct. 14, 2003

(54) AROMATIC DERIVATIVES AS HIV ASPARTYL PROTEASE INHIBITORS

(75) Inventors: Brent Richard Stranix, Pointe-Claire (CA); Jean-François Lavallée, Mille-Iles (CA); Nicolas LeBerre, Montreal (CA); Valérie Perron, Laval (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 10/326,488

(22) Filed: Dec. 23, 2002

(51) Int. Cl.$^7$ ............... A61K 31/455; A61K 31/5375; C07C 311/44; C07D 213/82; C07D 295/215
(52) U.S. Cl. ............... 514/237.5; 544/148; 544/159; 544/406; 546/316; 546/323; 548/333.5; 548/537; 549/438; 549/487; 560/10; 560/13; 562/427; 562/430; 564/86
(58) Field of Search ............... 544/159; 560/10; 546/316; 564/86; 514/237.5

(56) References Cited

U.S. PATENT DOCUMENTS 6,506,786 B2 * 1/2003 Stranix et al. ............... 548/482

FOREIGN PATENT DOCUMENTS

WO   WO 02/064551   8/2002

OTHER PUBLICATIONS

Meek et al., Nature, 343, p.p. 90–90–(1990).
Matayoshi et al. (Science 247: 954–954, (1990).
A.J. Japour et al. Antimicrobial Agents and Chemotherapy, vol. 37 (1993) pp. 1095–1101.
R. Pauwels et al. Journal of Virological Methods, vol. 20 (1988) pp. 309–321.

* cited by examiner

Primary Examiner—Robert W. Ramsuer
(74) Attorney, Agent, or Firm—Ronald S. Kosie; Robert Brouillette; Gaetan Prince

(57) ABSTRACT

The present invention provides HIV aspartyl protease inhibitors of the formula;

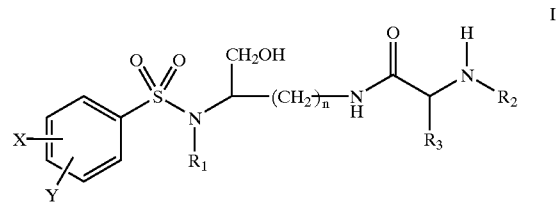

and when the compound of formula I comprises an amino group, pharmaceutically acceptable ammonium salts thereof, wherein n is 3 or 4, wherein $R_1$ may be, for example, iso-butyl, wherein X and Y, same or different, may be, for example, $NH_2$ and F, and wherein $R_2$ and $R_3$ are as defined herein.

62 Claims, No Drawings

AROMATIC DERIVATIVES AS HIV ASPARTYL PROTEASE INHIBITORS

TECHNICAL FIELD OF THE INVENTION

This invention concerns a novel class of aromatic derivatives possessing aspartyl protease inhibitory properties. It describes the synthetic methodology used to make these derivatives from readily available L-lysine analogues and their biological applications. In addition, this invention relates to different pharmaceutical compositions comprising these compounds. The compounds and the pharmaceutical compositions of this invention have been shown to inhibit the activity of HIV aspartyl protease, an enzyme essential for virus maturation and infectivity. The inhibitory property may be advantageously used to provide compounds with antiviral properties against HIV viruses, including the HIV-1 and HIV-2 viruses.

BACKGROUND OF THE INVENTION

HIV, the human immunodeficiency virus, causes AIDS through infection of specialized cells of the immune system carrying CD4 receptors. The HIV retrovirus reproduces in these cells, especially the so-called T-helper cells, and kills them in the process. While the body has the ability to re-generate T-helper cells to some extent, after years of continuous cell destruction by HIV and fighting back by the immune system, the virus eventually emerges as the battle's winner. The progressive destruction of T-helper cells leads to weakening of the immune system which in turn, opens the door to opportunistic pathogens. When this happens, HIV-infected people start to show clinical symptoms. If left unchecked, HIV infection leads to death in a matter of years.

In order to reproduce in infected cells, HIV needs three major enzymes that are carried inside the viral particle. These three enzymes, reverse transcriptase, protease and integrase, thus represent ideal targets for antiviral therapy. Of these, reverse transcriptase has been the first enzyme targeted by the pharmaceutical industry. Inhibitors of the viral protease have been developed more recently and their use as drugs for AIDS treatment began only in 1996.

Although the development of reverse transcriptase and protease inhibitors has improved significantly the survival time and quality of life of HIV-infected patients, their use leads to unwanted side effects, such as anemia, neurotoxicity, bone marrow suppression and lipodystrophy. Most of the currently available anti-protease drugs are large molecules with limited ability to cross the blood-brain barrier. New compounds devoid of these drawbacks are urgently needed to treat HIV infections. In addition, HIV has the ability to develop resistance to the currently available drugs, so new compounds with original structure are desirable to fight these resistant viral strains.

In an international patent application no PCT/CA02/00190 (Stranix et al.) published under No. WO 02/064551, HIV protease inhibitors based on amino acid derivaties are disclosed. This patent application includes, more particularly, N-amino acid substituted L-lysine derivatives (and analogs) possessing aspartyl protease inhibitory properties. However, it would be advantageous to be able to provide alternate compounds with such properties.

SUMMARY OF THE INVENTION

The present invention provides a novel class of compounds, including their pharmaceutically acceptable derivatives. These compounds have an affinity for aspartyl proteases, in particular, HIV-1 aspartyl protease. They also presents potent antiviral activity when tested on HIV-1 viral strain (NL4.3 as the wild type virus) as well as several mutant strains. Therefore, these compounds are useful as inhibitors of such proteases. These compounds can be used alone or in combination with other therapeutic or prophylactic agents for the treatment or prophylaxis of viral infection.

Compounds of the present invention may inhibit HIV viral replication in human cells (e.g., CD4+ T-cells), by inhibiting (reducing, impairing) the ability of HIV aspartyl protease to catalyse the hydrolysis of peptide bonds present in viral Gag and Gag-Pol polyproteins. These novel compounds may serve to reduce the production of infectious virions from acutely and chronically infected cells, and may inhibit (at least partially) the initial or further infection of host cells. Accordingly, these compounds may be useful as therapeutic and prophylactic agents to treat or prevent infection by HIV-1 and HIV-2, which may result in asymptomatic infection, AIDS-related complex (ARC), acquired immunodeficiency syndrome (AIDS), ADS-related dementia, or similar diseases of the immune system, and related viruses such as HTLV-I and HTLV-II, and simian immunodeficiency virus.

It is the main objective of this invention to provide an improved class of molecules that are aspartyl protease inhibitors, and particularly, HIV aspartyl protease inhibitors.

The present invention relates to improved Nε-synthetic amino acid substituted L-lysine derivatives (including its lower homologue (i.e. L-ornithine)) as well as their pharmaceutically acceptable derivatives (e.g., salts).

Accordingly, the present invention in accordance with one aspect thereof provides a compound(s) of formula I

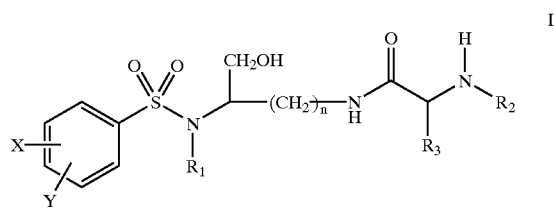

and when the compound of formula I comprises an amino group, pharmaceutically acceptable ammonium salts thereof, wherein n may be 3 or 4, wherein X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$ and —$CH_2OH$ or X and Y together define a alkylenedioxy group selected from the group consisting of a methylenedioxy group of formula —$OCH_2O$— and an ethylenedioxy group of formula —$OCH_2CH_2O$—, wherein $R_1$ may be selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein $R_2$ may be selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms (e.g. methyl, ethyl-, propyl, iso-propyl, butyl, iso-butyl, tert-butyl, tert-butyl-$CH_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-$CH_2$—, cyclohexyl-$CH_2$—, etc.), an alkyloxy group of 1 to 6 carbon atoms (e.g. $CH_3O$—, $CH_3CH_2O$—, iso-butylO-, tert-butylO-(Boc), etc.), tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

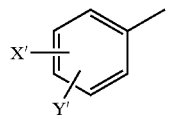

a picolyl group selected from the group consisting of

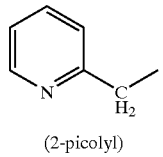 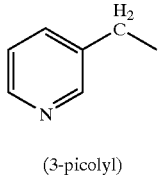 and 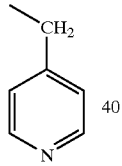

(2-picolyl)     (3-picolyl)     (4-picolyl)

a picolyloxy group selected from the group consisting of

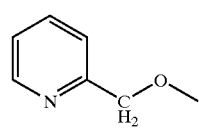 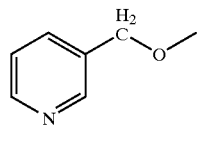 and (2-picolyloxy)   (3-picolyloxy)

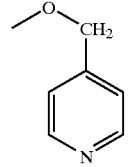

(4-picolyloxy)

a substituted pyridyl group selected from the group consisting of

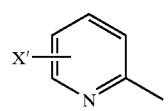 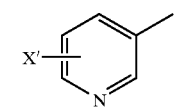 and (substituted 2-pyridyl)   (substituted 3-pyridyl)

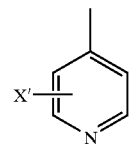

(substituted 4-pyridyl)

a group of formula,

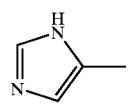

a group of formula,

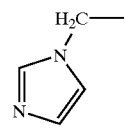

and a group of formula,

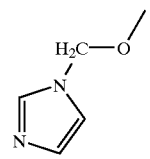

wherein X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R_4$ and $R_5$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms, wherein $R_3$ may be selected from the group consisting of a diphenylmethyl group of formula IV

IV

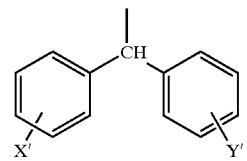

a naphthyl-1-CH$_2$— group of formula V

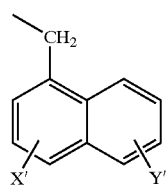

a naphthyl-2-CH$_2$— group of formula VI

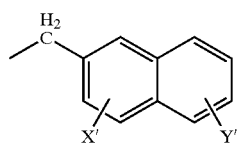

a biphenylmethyl group of formula VII

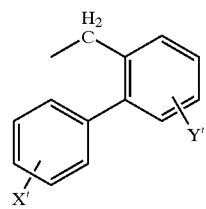

and an anthryl-9-CH$_2$— group of formula VIII

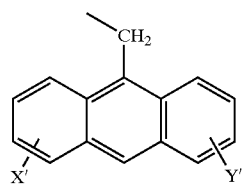

wherein X' and Y' are as defined herein.

In a further aspect, the present invention provides, a compound(s) of formula II,

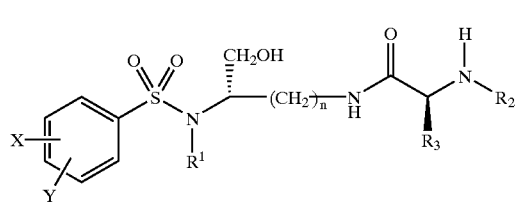

and when the compound of formula II comprises an amino group, pharmaceutically acceptable ammonium salts thereof, wherein n may be 3 or 4, wherein X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —OR$_4$, —SR$_4$, —COOR$_4$, —COR$_4$ and —CH$_2$OH or X and Y together define an alkylenedioxy group selected from the group consisting of a methylenedioxy group of formula —OCH$_2$O— and an ethylenedioxy group of formula —OCH$_2$CH$_2$O—, wherein R$_1$ may be selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R$_2$ may be selected from the group consisting of H, a straight alkyl group of 1 to 6 carbon atoms, a branched alkyl group of 3 to 6 carbon atoms, a cycloalkyl group of 3 to 6 carbon atoms, and a group of formula R$_{2A}$—CO—, R$_{2A}$ being selected from the group consisting of a straight or branched alkyl group of 1 to 6 carbon atoms (e.g. methyl, ethyl-, propyl, iso-propyl, butyl, iso-butyl, tert-butyl, tert-butyl-CH$_2$—, etc.), a cycloalkyl group having 3 to 6 carbon atoms (e.g. cyclopropyl-, cyclohexyl- etc.), a cycloalkylalkyl group having 3 to 6 carbon atoms in the cycloalkyl part thereof and 1 to 3 carbon atoms in the alkyl part thereof, (e.g. cyclopropyl-CH$_2$—, cyclohexyl-CH$_2$—, etc.), an alkyloxy group of 1 to 6 carbon atoms (e.g. CH$_3$O—, CH$_3$CH$_2$O—, iso-butylO-, tert-butylO-(Boc), etc.), tetrahydro-3-furanyloxy, —CH$_2$OH, —CF$_3$, —CH$_2$CF$_3$, —CH$_2$CH$_2$CF$_3$, pyrrolidinyl, piperidinyl, 4-morpholinyl, CH$_3$O$_2$C—, CH$_3$O$_2$CCH$_2$—, Acetyl-OCH$_2$CH$_2$—, HO$_2$CCH$_2$—, 3-hydroxyphenyl, 4-hydroxyphenyl, 4-CH$_3$OC$_6$H$_4$CH$_2$—, CH$_3$NH—, (CH$_3$)$_2$N—, (CH$_3$CH$_2$)$_2$N—, (CH$_3$CH$_2$CH$_2$)$_2$N—, HOCH$_2$CH$_2$NH—, CH$_3$OCH$_2$O—, CH$_3$OCH$_2$CH$_2$O—, C$_6$H$_5$CH$_2$O—, 2-pyrrolyl, 2-pyridyl, 3-pyridyl, 4-pyridyl, 2-pyrazinyl, 2-quinolyl, 3-quinolyl, 4-quinolyl, 1-isoquinolyl, 3-isoquinolyl, 2-quinoxalinyl, a phenyl group of formula

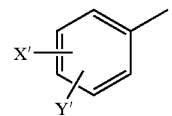

a picolyl group selected from the group consisting of

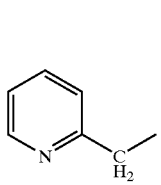 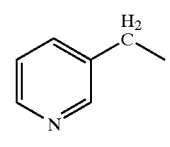 and 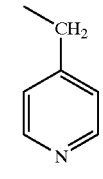

(2-picolyl)　　(3-picolyl)　　(4-picolyl)

a picolyloxy group selected from the group consisting of

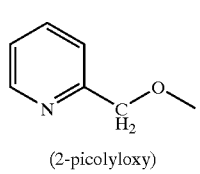 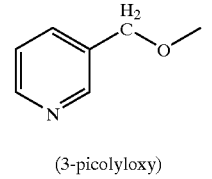 and (2-picolyloxy)　　(3-picolyloxy)

-continued

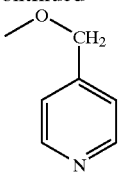

(4-picolyloxy)

a substituted pyridyl group selected from the group consisting of

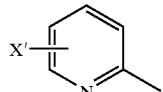  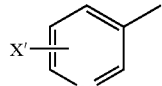   and (substituted 2-pyridyl)   (substituted 3-pyridyl)

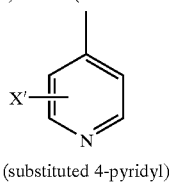

(substituted 4-pyridyl)

a group of formula,

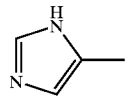

a group of formula,

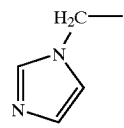

and a group of formula,

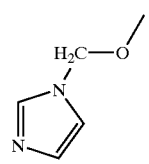

wherein X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R_4$ and $R_5$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms, wherein $R_3$ may be selected from the group consisting of a diphenylmethyl group of formula IV

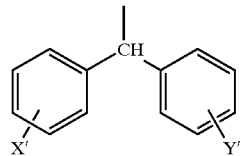

a naphthyl-1-$CH_2$— group of formula V

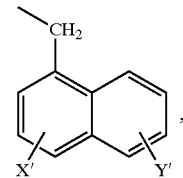

a naphthyl-2-$CH_2$— group of formula VI

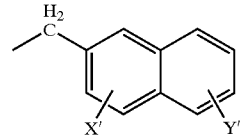

a biphenylmethyl group of formula VII

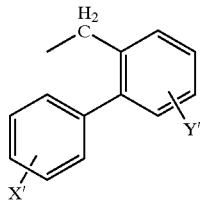

and an anthryl-9-$CH_2$— group of formula VIII

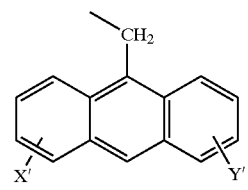

wherein X' and Y' are as defined herein.

Compounds of formula I or II wherein $R_1$ may be, more particularly iso-butyl are encompassed by the present invention.

In accordance with the present invention, n may be 3 or 4.

Also in accordance with the present invention, $R_2$ may be selected, more particularly from the group consisting of $CH_3O$—CO, $(CH_3)_2N$—CO, 3-pyridyl-CO, 4-pyridyl-CO and 4-morpholinyl-CO.

In accordance with the present invention X may be 4-$NH_2$ while Y may be H. Alternatively, X may be 3-Cl, while Y may be 4-$NH_2$. On the other hand, X may be 4-$NH_2$ while Y may be 3-F. Also, for example, X may be 3-$NH_2$ while Y may be 4-F.

More particularly, when $R_1$, $R_2$, n, X and Y are as defined above, $R_3$ may be, for example, selected from the group consisting of a diphenylmethyl group of formula IV, a naphthyl-1-$CH_2$— group of formula V, a naphthyl-2-$CH_2$— group of formula VI, a biphenylmethyl group of formula VII and an anthryl-9-$CH_2$— group of formula VIII. More particularly, $R_3$ may be, for example, selected from the group consisting of a diphenylmethyl group of formula IV, a naphthyl-1-$CH_2$— group of formula V, a naphthyl-2-$CH_2$— group of formula VI, and a biphenylmethyl group of formula VII.

In accordance with the present invention X' and Y' may both be H.

In an additional aspect, the present invention provides a compound(s) of formula IIa

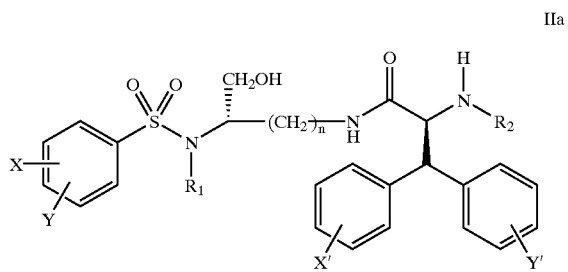

IIa and when the compound of formula IIa comprises an amino group, pharmaceutically acceptable ammonium salts thereof, wherein X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, and wherein n, $R_1$, $R_2$, $R_4$, and $R_5$ may be as defined above.

Compounds of formula IIa wherein $R_1$ may be, more particularly iso-butyl are encompassed by the present invention.

In accordance with the present invention, n may be 3 or 4.

Also in accordance with the present invention, $R_2$ may be, more particularly selected from the group consisting of $CH_3O$—CO, $(CH_3)_2N$—CO, 3-pyridyl-CO, 4-pyridyl-CO and 4-morpholinyl-CO.

In accordance with the present invention X may be 4-$NH_2$ while Y, X' and Y' may be H. Alternatively, X may be 3-$NH_2$ and Y may be 4-F while X' and Y' may both be H. On the other hand, X may be 4-$NH_2$ and Y may be 3-F, while X' and Y' may both be H.

Accordingly, compounds of formula IIa wherein X may be 4-$NH_2$, Y may be H, X' may be H, Y' may be H and $R_2$ may be $CH_3O$—CO are encompassed by the present invention. Also encompassed by the present invention, are, for example, compounds of formula IIa wherein X may be 4-F, Y may be 3-$NH_2$, X' may be H, Y' may be H and $R_2$ may be $CH_3O$—CO. Alternatively, compounds wherein X may be 4-$NH_2$, Y may be H, X' may be H, Y' may be H and $R_2$ may be cyclopropyl-CO are also encompassed by the present invention. On the other hand, compounds wherein X may be 4-$NH_2$, Y may be H, X' may be H, Y' may be H and $R_2$ may be $(CH_3)_2N$—CO are also encompassed by the present invention. Again, compounds wherein X may be 4-$NH_2$, Y may be H, X' may be H, Y' may be H and $R_2$ may be 3-pyridyl-CO are also included. Furthermore, compounds wherein X may be 4-$NH_2$, Y may be H, X' may be H, Y' may be H and $R_2$ may be 4-pyridyl-CO and compounds wherein X may be 4-$NH_2$, Y may be H, X' may be H, Y' may be H and $R_2$ may be 2-picolylO—CO are also included. The compounds listed above are examplary embodiments of the present invention and it is to be understood that the present invention is not restricted to these compounds only.

In yet a further aspect, the present invention provides a compound(s) of formula IIb

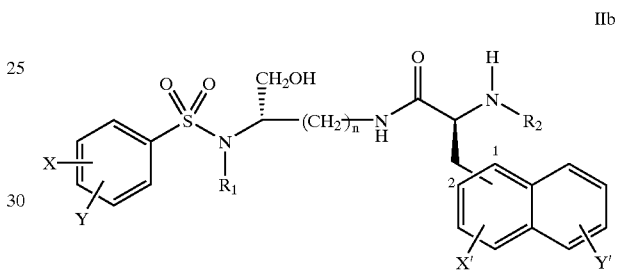

IIb and when the compound of formula IIb comprises an amino group, pharmaceutically acceptable ammonium salts thereof, wherein X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$ and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, and wherein n, $R_1$, $R_2$, $R_4$, and $R_5$ may be as defined above.

Compounds of formula IIb wherein $R_1$ may more particularly be iso-butyl are encompassed by the present invention.

In accordance with the present invention n may be 3 or 4.

Also in accordance with the present invention, $R_2$ may be more particularly selected from the group consisting of $CH_3O$—CO, $(CH_3)_2N$—CO, 3-pyridyl-CO, 4-pyridyl-CO and 4-morpholinyl-CO.

Further in accordance with the present invention, X may be 4-$NH_2$, while Y, X' and Y' may be H. On the other hand, compounds of formula IIb wherein X may be 3-NH$_2$, and Y may be 4-F while X' and Y' may be H are also encompassed by the present invention. Alternatively, compounds wherein X may be 4-NH$_2$ and Y may be 3-F while X' and Y' may be H are also included.

In accordance with the present invention, compounds of formula IIb wherein X may be 4-NH$_2$, Y may be H, X' and Y' may be H and R$_2$ may be (CH$_3$)$_2$N—CO are encompassed by the present invention.

Also in accordance with the present invention the naphthyl group of compounds of formula IIb may be, more particularly naphthyl-2-CH$_2$.

In another aspect, the present invention provide a compound(s) of formula IIc

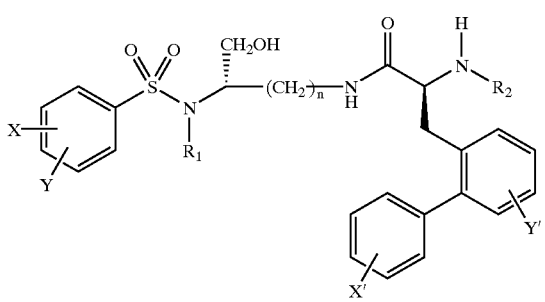

IIc and when the compound of formula IIc comprises an amino group, pharmaceutically acceptable ammonium salts thereof, wherein X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —OCF$_3$, —CN, —NO$_2$, —NR$_4$R$_5$, —NHCOR$_4$, —OR$_4$, —SR$_4$, —COOR$_4$, —COR$_4$ and —CH$_2$OH or X and Y together define an alkylenedioxy group selected from the group consisting of a methylenedioxy group of formula —OCH$_2$O— and an ethylenedioxy group of formula —OCH$_2$CH$_2$O—, wherein X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, and wherein n, R$_1$, R$_2$, R$_4$, and R$_5$ may be as defined above.

Compounds of formula IIc wherein R$_1$ may be more particularly iso-butyl are encompassed by the present invention.

Further in accordance with the present invention n may be 3 or 4.

Also in accordance with the present invention, R$_2$ may more particularly be selected from the group consisting of CH$_3$O—CO, (CH$_3$)$_2$N—CO, 3-pyridyl-CO, 4-pyridyl-CO and 4-morpholinyl-CO.

Further in accordance with the present invention X may be 4-NH$_2$ while Y, X' and Y' may be H. On the other hand compounds of formula IIc, wherein X may be 3-NH$_2$ and Y may be 4-F while X' and Y' may be H are also encompassed by the present invention. Alternativley, compounds where X may be 4-NH$_2$ and Y may be 3-F while and Y' may be H are also included herein. Again, this list (as well as any other list or example enumerated herein) is not exhaustive of the compounds encompassed by the present invention.

This invention also provides in a further aspect, pharmaceutical compositions comprising a pharmaceutically acceptable carrier and at least one compound of formula I, II, IIa, IIb, or IIc (and combination thereof) as defined herein. The pharmaceutical composition may comprise, for example, a pharmaceutically effective amount of such one or more compounds or as applicable, pharmaceutically acceptable ammonium salts thereof.

The present invention also relates in an additional aspect thereof, to pharmaceutical compositions comprising a pharmaceutically acceptable carrier and at least one of the following compounds;

a compound of formula IIa wherein R$_1$ is iso-butyl, n is 4, X is 4-NH$_2$, Y is H, X' is H, Y' is H and R$_2$ is CH$_3$O—CO, a compound of formula IIa wherein R$_1$ is iso-butyl, n is 4, X is 4-F, Y is 3-NH$_2$, X' is H, Y' is H and R$_2$ is CH$_3$O—CO, a compound of formula IIa wherein R$_1$ is iso-butyl, n is 4, X is 4-NH$_2$, Y is H, X' is H, Y' is H and R$_2$ is cyclopropyl-CO, a compound of formula IIa wherein R$_1$ is iso-butyl, n is 4, X is 4-NH$_2$, Y is H, X' is H, Y' is H and R$_2$ is (CH$_3$)$_2$N—CO, a compound of formula IIa wherein R$_1$ is iso-butyl, n is 4, X is 4-NH$_2$, Y is H, X' is H, Y' is H and R$_2$ is 3-pyridyl-CO, a compound of formula IIa wherein R$_1$ is iso-butyl, n is 4, X is 4-NH$_2$, Y is H, X' is H, Y' is H and R$_2$ is 4-pyridyl-CO, a compound of formula IIa wherein R$_1$ is iso-butyl, n is 4, X is 4-NH$_2$, Y is H, X' is H, Y' is H and R$_2$ is 2-picolylO—CO or;

a compound of formula IIb wherein R$_1$ is iso-butyl, n is 4, X is 4-NH$_2$, Y is H, X' is H, Y' is H, R$_2$ is (CH$_3$)$_2$N—CO and wherein the naphthyl group is a naphthyl-2-CH$_2$ group.

The term "pharmaceutically effective amount" refers to an amount effective in treating HIV infection in a patient. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount having an inhibitory effect on HIV (HIV-1 and HIV-2 as well as related viruses (e.g., HTLV-I and HTLV-II, and simian immunodeficiency virus)) infection cycle (e.g., inhibition of replication, reinfection, maturation, budding etc.) and on any organism depending on aspartyl proteases for their life cycle.

In addition, this invention provides pharmaceutical compositions in which these novel compounds of formula I, (as well as of formulae II, IIa, IIb, and IIc) derived from L-lysine or L-lysine derivatives (as well as its lower homologue (i.e. L-ornithine)) are used to inhibit aspartyl proteases, including HIV aspartyl protease, thus providing protection against HIV infection.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "prophylactically effective amount" refers to an amount effective in preventing HIV infection in a patient. As used herein, the term "patient" refers to a mammal, including a human.

The terms "pharmaceutically acceptable carrier", "pharmaceutically acceptable adjuvant" and "physiologically acceptable vehicle" refer to a non-toxic carrier or adjuvant that may be administered to a patient, together with a compound of this invention, and which does not destroy the pharmacological activity thereof.

The compounds of this invention include pharmaceutically acceptable derivatives of the compounds of formula I (as well as of formulae II, IIa, IIb, and IIc) and as applicable pharmaceutically acceptable ammonium salts thereof. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof.

It is to be understood herein that a "straight alkyl group of 1 to 6 carbon atoms" includes for example, methyl, ethyl, propyl, butyl, pentyl, hexyl.

It is to be understood herein that a "branched alkyl group of 3 to 6 carbon atoms" includes for example, without limitation, iso-butyl, tert-butyl, 2-pentyl, 3-pentyl, etc.

It is to be understood herein, that a "cycloalkyl group having 3 to 6 carbon" includes for example, without limitation, cyclopropyl, cyclobutyl, cyclopentyl, cyclocyclohexyl (i.e., $C_6H_{11}$).

Salts derived from appropriate bases include alkali metal (e.g., sodium), alkaline earth metal (e.g., magnesium), ammonium and $N-(C_{1-4}$ alkyl$)_4^+$ salts.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

with respect to reaction time, a time of 1 minute or more is to be understood as specifically incorporating herein each and every individual time, as well as sub-range, above 1 minute, such as for example 1 minute, 3 to 15 minutes, 1 minute to 20 hours, 1 to 3 hours, 16 hours, 3 hours to 20 hours etc.;

and similarly with respect to other parameters such as concentrations, elements, etc. . .

It is in particular to be understood herein that the compound formulae each include each and every individual compound described thereby as well as each and every possible class or sub-group or sub-class of compounds whether such class or sub-class is defined as positively including particular compounds, as excluding particular compounds or a combination thereof; for example an exclusionary definition for the formula (e.g. I) may read as follows: "provided that when one of A and B is —COOH and the other is H, —COOH may not occupy the 4' position".

It is also to be understood herein that "g" or "gm" is a reference to the gram weight unit and "C", or "° C." is a reference to the Celsius temperature unit.

The compounds of this invention are easily prepared using conventional techniques from readily available starting materials. Two different approaches were used to prepare the new aspartyl protease inhibitors. The first approach starts from an L-ornithine derivative which is transformed into the key intermediate (1S)-4-amino-N-(4-amino-1-hydroxymethyl-butyl)-N-isobutyl-benzenesulfonamide (VII, example 1, step F) which is further reacted with various acid to yield the end products VIII. The second approach starts from L-α-amino-ε-caprolactam which leads to key intermediates (such as, (1S)-4-amino-N-(5-amino-1-hydroxymethyl-pentyl)-N-isobutyl-benzenesulfonamide (XII, X=NH$_2$, Y=H, example 28, step D)) which are further transformed into various end products (XIII) upon coupling with a suitable acid synthon. The detailed description of these approaches are presented in schemes 1 to 4 discussed below.

Scheme 1 illustrates the preparation of a key L-ornithine intermediate VII needed for the synthesis of HIV protease inhibitors according to the first approach (see example 1 in the experimental portion of this document).

Note:
a) R represents the "residue" of the acid molecule which is linked to the free primary amino group present on intermediate VII.

The synthesis of intermediate VII uses Nε-Z-ornithine (I) as the starting material. The ester II was obtained upon treatment with trimethylsilyl chloride in methanol. Then, sulfonation with 4-nitrobenzenesulfonyl chloride (or other substituted-benzenesulfonyl chloride) in the presence of triethylamine in dichloromethane gave compound III in excellent yields for the two first steps. Alkylation of the sulfonyl amine was performed with iso-butanol in the presence of triphenylphosphine and diethylazodicarboxylate (DEAD) to give compound IV in excellent yield. The nitro function was reduced with sodium borohydride in the presence of nickel (II) acetate in ethanol. The intermediate V was obtained in 97% yield. Subsequent reduction of the ester function with lithium borohydride in ethanol gave the alcohol VI quantitatively. Removal of the benzyloxycarbonyl group (Z group) by hydrogen gas in presence of 10% Pd/C yielded the free Nε-amino derivative VII quantitatively (T. W. Greene and P. G. M. Wuts, Protective groups in Organic Synthesis, $3^{rd}$ Edition, John Wiley & Sons, Inc. 2000). Acylation with an appropriate acid in the presence of 1-hydroxybenzotriazole (HOBt) and 1-[3-(dimethylamino)propyl]-3-ethylcarbodiimide hydrochloride (EDAC) led to the desired end products VIII generally in good to excellent yield (50–95%).

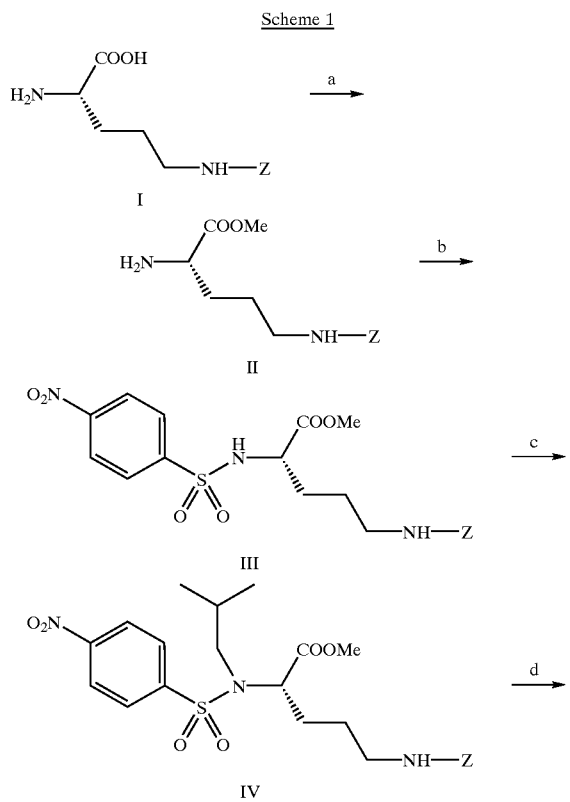

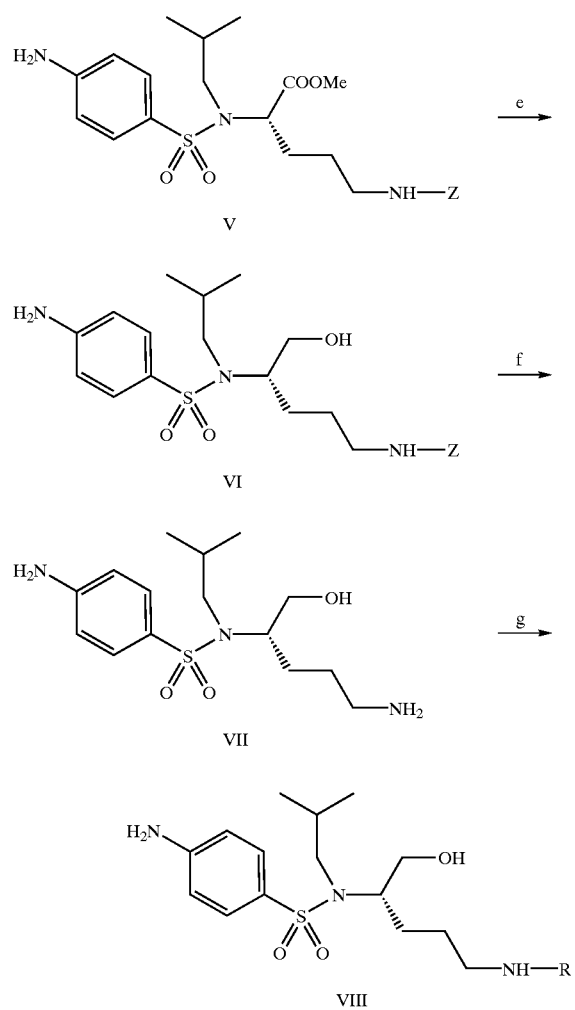

Reagents: a) TMS—Cl/MeOH; b) 4-$NO_2C_6H_4SO_2Cl$, $Et_3N/CH_2Cl_2$;
c) i-Bu—OH, $PPh_3$, DEAD/THF; d) $Ni(OAc)_2$·4 $H_2O$, $NaBH_4$/EtOH;
e) $LiBH_4$/EtOH; f) $H_2$, Pd—C 10%/MeOH;
g) R—OH, HOBt, EDAC/DMF—$CH_2Cl_2$ Scheme 2 illustrates a generic example for the preparation of HIV protease inhibitors made with the second approach starting from L-α-amino-ε-caprolactam to give compounds of the general formula XIII.

Note:
a) For scheme 2, X and Y, same or different, represents H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, —$CH_2OH$, and wherein X and Y may be bound together as a methylenedioxy group of formula —$OCH_2O$—, or as an ethylenedioxy group of formula —$OCH_2CH_2O$—, ($R_4$ and $R_5$ are as defined above)
b) R represents the "residue" of the acid molecule which is linked to the free primary amino group present on intermediate XII.

As shown in scheme 2, the Nα,Nα-disubstituted L-lysinol derivative XII was obtained from L-α-amino-ε-caprolactam in a four-step reaction sequence. Initially, L-α-amino-ε-caprolactam was transformed into (2S)-3-isobutylamino-azepan-2-one (IX) by reductive alkylation of the amine with an appropriate aldehyde (i.e. isobutyraldehyde), NaBH(OAc)$_3$ and acetic acid in dichloroethane. Then, sulfonation with an arylsulfonyl chloride (or a substituted-arylsulfonyl chloride) in the presence of triethylamine in dichloromethane gave compound X in excellent yields. The derivative XI was obtained quantitatively upon treatment of X with di-tert-butyl pyrocarbonate and DMAP in acetonitrile. The reductive ring opening with sodium borohydride in ethanol and acid deprotection of the Boc protective group lead to key intermediates XII in good yield. Finally, coupling of the free amino group present on intermediate XII with a variety of acid in the presence of 1-hydroxybenzotriazole (HOBt) and 1-[3-(dimethylamino)propyl]-3-ethylcarbodiimide hydrochloride (EDAC) led to the desired end HIV protease inhibitors XIII.

(XIV) into an unsubstituted or a substituted biphenyl derivative of general formula XVI.

Note:
a) For scheme 3, R represents the "residue" of the acid molecule which is linked to the free primary amino group present on compound XIV.
b) X' represents a straight alkyl group of 1 to 6 carbon atoms, a branched alkyl group of 3 to 6 carbon atoms, a cycloalkyl group of 3 to 6 carbon atoms, F, Cl, Br, I, —CF$_3$, —NO$_2$, —NR$_4$R$_5$, —NHCOR$_4$, —OR$_4$, —SR$_4$, —COOR$_4$, —COR$_4$ and —CH$_2$OH, (R$_4$ and R$_5$ are as defined above)

As shown in scheme 3, the unsubstituted (or substituted) biphenyl derivative of general formula XVI was obtained from commercially available (2S)-2-amino-3-(2-bromo-phenyl)-propionic acid (XIV, L-2-bromo-Phe (Peptech Corp.)) in a two-step reaction sequence. First, the amine is acylated with an appropriate synthon under standard reaction conditions to give the intermediate XV in excellent yield. The latter was transformed into the biphenyl derivative XVI upon treatment with phenylboronic acid (or a substituted phenylboronic acid) in the presence of Pd/C

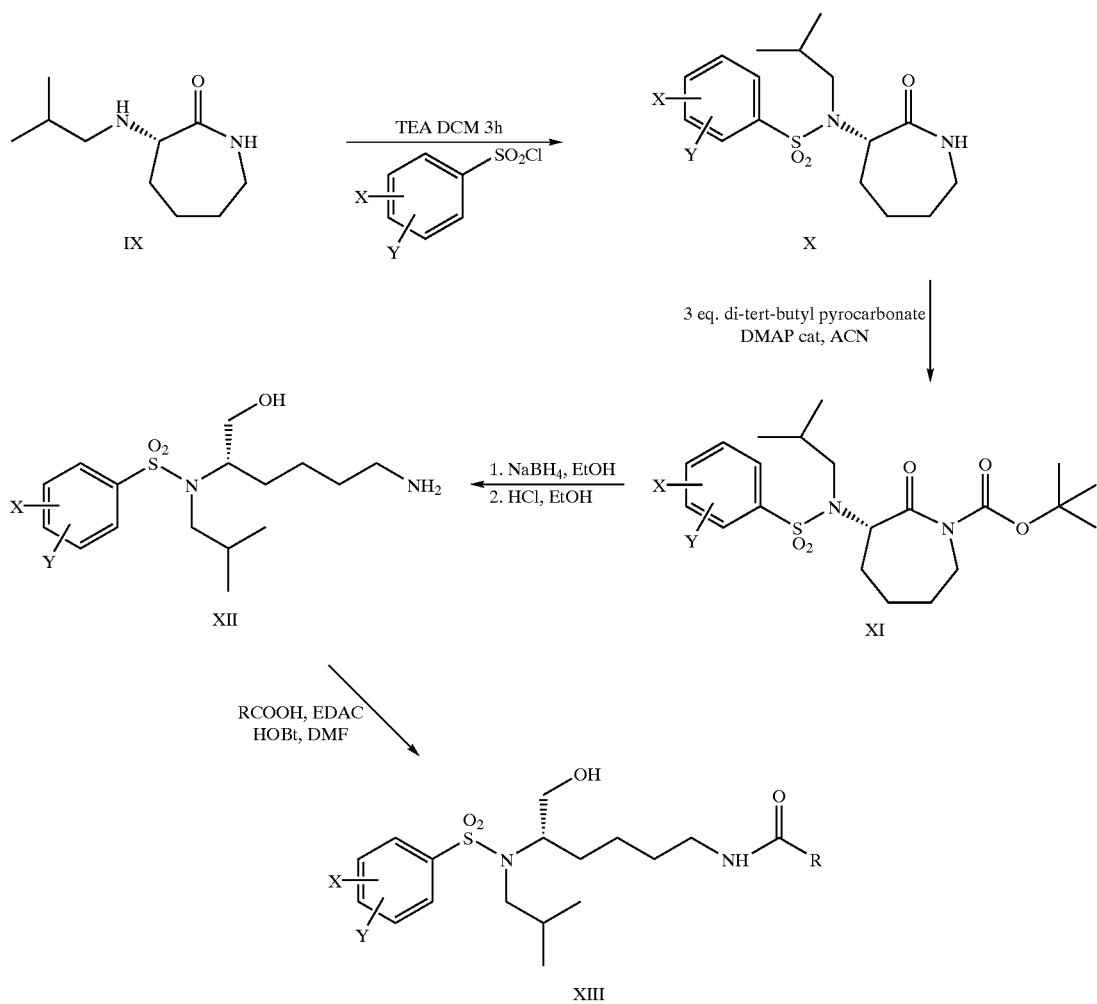

Scheme 2

Scheme 3 illustrates a generic example for the transformation of (2S)-2-amino-3-(2-bromo-phenyl)-propionic acid Degussa type E 101 under basic reaction condition. The biphenyl derivative are obtained in excellent yield with this methodology. The biphenyl derivatives hence obtained are linked to the key intermediates VII or XII as described on schemes 1 and 2.

Scheme 3

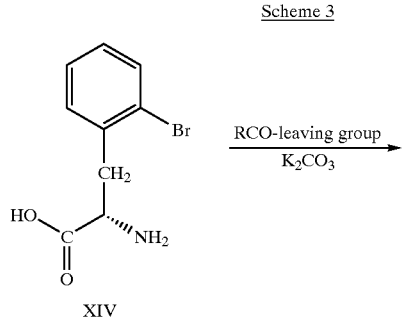

XIV

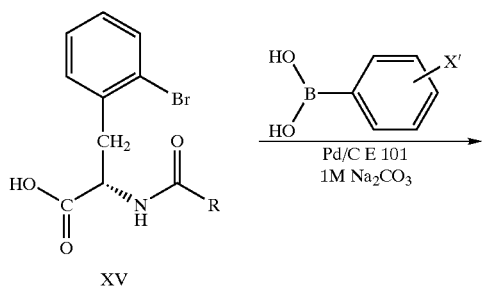

XV

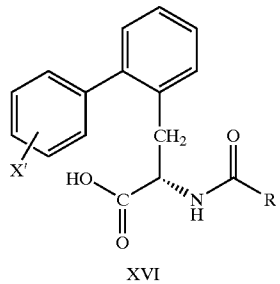

XVI

Scheme 4 presents the transformation of a 2-naphthyl derivative XVII into a variety of N-substituted molecules of general formula XIX. This reaction sequence could be used to produce any other similar compounds made of unsubstituted (or substituted) diphenylmethyl, 1-naphthyl, 2-naphthyl, biphenyl and 9-anthryl described in this invention.

Note:
a) For scheme 4, R represents the "residue" of the molecule (an acid, acid chloride, an aldehyde or a succinimidylcarbonate ester) which is linked to the free primary amino group present on compound XVIII.

Initially, the Boc protective group is cleaved under standard acidic reaction conditions with hydrochloric acid in ethanol to give 2-amino-N-{5-[(4-amino-benzenesulfonyl)-isobutyl-amino]-6-hydroxy-hexyl}-3-naphthalen-2-yl-propionamide (XVIII) in 94% yield (see example 49, in the experimental section). The free amino group on molecule XVIII was transformed into a variety of HIV aspartyl protease inhibitors of formula XIX using either general procedures C or D, for the linkage of an acid chloride, general procedures A, B or E, for the linkage of a carboxylic acid, general procedure F, for the linkage of an aldehyde or general procedure G, for the linkage of an activated carbonate diester.

Scheme 4

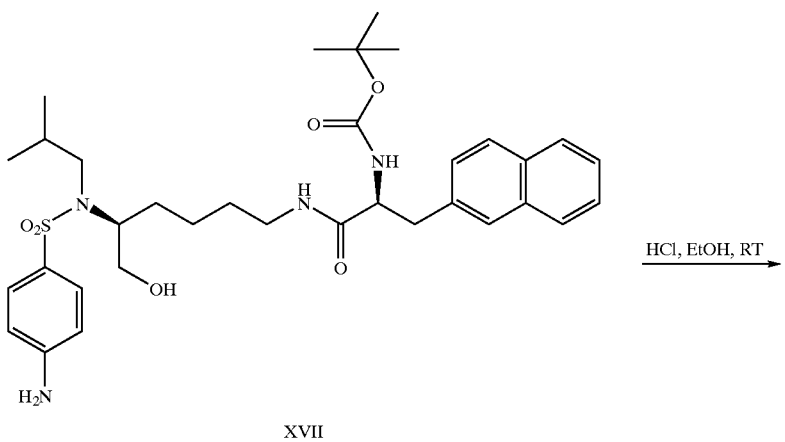

XVII

-continued

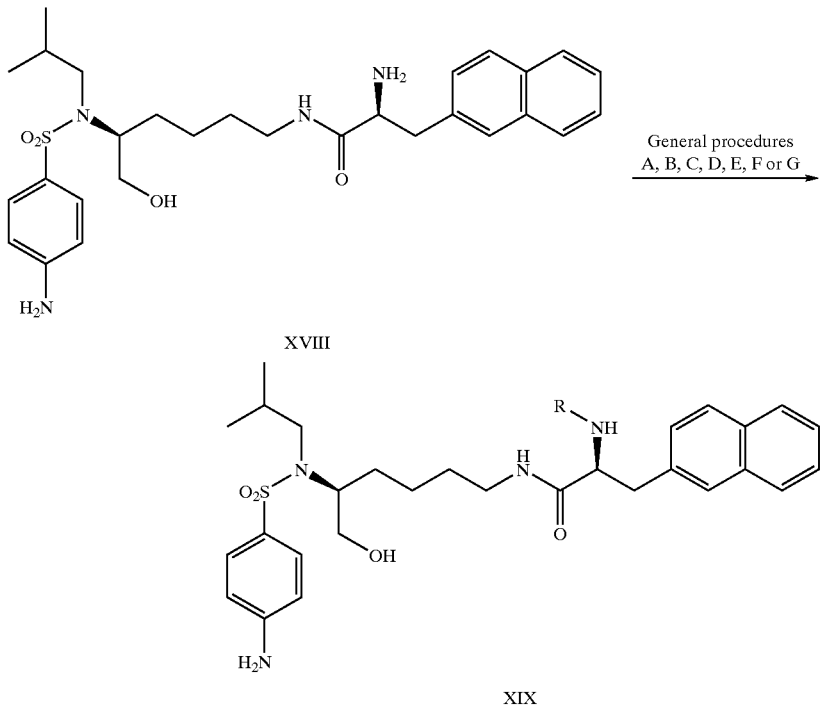

XVIII

General procedures
A, B, C, D, E, F or G
→

XIX

As it can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the novel compounds of the present invention are excellent ligands for aspartyl proteases, particularly HIV-1 protease. Accordingly, these compounds are capable of targeting and inhibiting late stage events in the replication, i.e. the processing of the viral polyproteins by HIV encoded protease. Compounds according to this invention advantageously inhibit the ability of the HIV-1 virus to infect immortalized human T cells over a period of days, as determined by an assay measuring the amount of extracellular p24 antigen—a specific marker of viral replication (see, Meek et al., Nature, 343, pp. 90–92 (1990)).

In addition to their use in the prophylaxis or treatment of HIV or HTLV infection, the compounds according to this invention may also be used as inhibitory or interruptive agents for other viruses which depend on aspartyl proteases, similar to HIV or HTLV aspartyl proteases, for obligatory events in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from acutely and chronically infected cells. The compounds of this invention advantageously inhibit aspartyl proteases, thus blocking the ability of aspartyl proteases to catalyse the hydrolysis of peptide bonds.

The compounds of this invention may be employed in a conventional manner for the treatment or prevention of HIV, HTLV, and other viral infections, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against viral infections, such as HIV infection. As such, the novel protease inhibitors of this invention can be administered as agents for treating or preventing viral infections, including HIV infection, in a mammal.

The compounds of this invention may be administered to a healthy or HIV-infected patient either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent can be one which targets early events in the viral life cycle, such as attachment to the cell receptor and cell entry, reverse transcription and viral DNA integration into cellular DNA. Antiviral agents targeting such early life cycle events include among others polysulfated polysaccharides, sT4 (soluble CD4) and other compounds which block binding of virus to CD4 receptors on CD4 bearing T-lymphocytes and other CD4(+) cells, or inhibit fusion of the viral envelope with the cytoplasmic membrane, and didanosine (ddI), zalcitabine (ddC), stavudine (d4T), zidovudine (AZT) and lamivudine (3TC) which inhibit reverse transcription. Other anti-retroviral and antiviral drugs may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, other types of drugs may be used to potentiate the effect of the compounds of this invention, such as viral uncoating inhibitors, inhibitors of Tat or Rev trans-activating proteins, antisense molecules or inhibitors of the viral integrase. These compounds may also be co-administered with other inhibitors of HIV aspartyl protease.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC, d4T or other reverse transcriptase inhibitors.

Alternatively, the compounds of this invention may also be co-administered with other HIV protease inhibitors such as Ro 31-8959 (Saquinavir; Roche), L-735,524 (Indinavir; Merck), AG-1343 (Nelfinavir; Agouron), A-84538 (Ritonavir; Abbott), ABT-378/r (Lopinavir; Abbott), and VX-478 (Amprenavir; Glaxo) to increase the effect of therapy or prophylaxis against various viral mutants or members of other HIV quasi species.

We prefer administering the compounds of this invention as single agents or in combination with retroviral reverse transcriptase inhibitors, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbamate sodium, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar aspartyl proteases for obligatory events in their life cycle. These viruses include, but are not limited to, retroviruses causing AIDS-like diseases such as simian immunodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene or polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide by an aspartyl protease, or may be derivatized to bind to a stable resin as a tethered substrate for affinity chromatography applications. These and other uses which characterize commercial aspartyl protease inhibitors will be evident to those of ordinary skill in the art.

In the description herein, the following abbreviations are used:

| Abbreviation | Meaning |
| --- | --- |
| Ac | Acetyl |
| AcOH | Acetic acid |
| CAN | Acetonitrile |
| APCI | Atmospheric pressure chemical ionization |
| ARC | AIDS-related complex |
| AIDS | Acquired Immunodeficiency Syndrome |
| AZT | 3-Azido-3-deoxythymine (Zidovudine) |
| i-$C_4H_9$ | iso-Butyl |
| t-Butyl | tert-Butyl |
| CAM | Cerium ammonium molybdate |
| CDI | N,N'-carbonyldiimidazole |
| DABCYL | 4-[[4'-(dimethylamino)phenyl]azo]benzoic acid |
| DCC | Dicyclohexylcarbodiimide |
| DCE | Dichloroethane |
| DCM | Dichloromethane |
| DEAD | Diethylazodicarboxylate |
| DIEA | N,N-Diisopropylethylamine |
| DMAP | N,N-dimethylaminopyridine |
| DMSO | Dimethylsulfoxide |
| DMF | Dimethylformamide |
| DNA | Deoxyribonucleic acid |
| EDAC | 1-[3-(dimethylamino)propyl]-3-ethylcarbodiimide hydrochloride |
| EDANS | 5-[(2'-aminoethyl)amino]naphthalene sulfonic acid |
| EtOAc | Ethyl acetate |
| EtOH | Ethyl alcohol |
| FRET | Fluorescence resonance energy transfer |
| g | Gram |
| h | hour |
| HIV-1,-2 | Human immunodeficiency virus type 1, type 2 |
| HOBt | 1-Hydroxybenzotriazole |
| HPLC | High performance liquid chromatography |
| HTLV-I, -II | Human T-cell lymphotropic virus type I, type II |
| IL-2 | Interleukin-2 |
| Kg | Kilogram |

-continued

| Abbreviation | Meaning |
|---|---|
| L | Liter |
| LAH | Lithium aluminum hydride |
| LC-MS | Liquid chromatography-mass spectrometry |
| M | Molar |
| MeOH | Methyl alcohol |
| mg | Milligram |
| mp | Melting point |
| min | Minute |
| Moc | Methoxycarbonyl |
| mol | Mole |
| mL | Milliliter |
| mmol | Millimole |
| MTT | 3-(dimethylthiazol-2-yl)-2,5-diphenyl-2H-tetrazolium bromide |
| nM | Nanomolar |
| rEPO | Recombinant erythropoietin |
| RNA | Ribonucleic acid |
| TLC | Thin layer chromatography |
| 3TC | 2',3'-Dideoxy-3-thiacytidine |
| TFA | Trifluoroacetic acid |
| THF | Tetrahydrofuran |
| Z | Benzyloxycarbonyl |

EXAMPLES

This section describes the synthesis of several molecules that are presented in this document. These examples are for the purpose of illustration only and are not to be construed as limiting the scope of the invention in any way. This section presents the detailed synthesis of compounds no. 1 to 116 of this invention.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were perform on a Gilson apparatus equipped with a C18 column, a 215 liquid handler module and 25 mL/min capacity head pumps. The HPLC is operated with a Gilson UniPoint System Software.

Semi-preparative HPLC Conditions for Purification of Test Compounds

HPLC system: 2 Gilson #305-25 mL pumps, Gilson #215 liquid handler for injection and collection and a Gilson #155 UV-Vis absorbance detector, all controlled from a Gilson Unipoint V1.91 software Column: Alltech (#96053) Hyperprep PEP, C-18, 100 Å α, 8 μm, 22×250 mm Flow: 15 mL/min Solvents: A:$H_2O$; B:$CH_3CN$ Gradient: 25% to 80% of B over 40 min Detector: absorbance; λ: 210 & 265 nm The crude material dissolved in acetonitrile to a concentration of around 50 to 80 mg/2 mL were injected in each run. Fractions were collected in amounts of 9 mL pertaining absorbance was detected at the UV detector.

Unless otherwise indicated, all starting materials were purchased from a commercial source such as Aldrich Co. or Sigma Co.

Melting points (mp) were determined on a Büchi 530 melting point apparatus in capillary tubes and were uncorrected.

Optical rotations ($[\alpha]_D^t$) were measured using a Jasco DIP-370 digital polarimeter at 589 nm (the D line of sodium). Specific rotation is calculated from the observed rotation according to the expression:

$$[\alpha]_D^t = 100\alpha/l\cdot c.$$

where $[\alpha]_D$=specific rotation,

α=observed rotation, c=concentration of the sample in grams per 100 mL of solution, l=the length of the polarimeter cell in decimeters, t=temperature (° C.).

Mass spectra were recorded on a Hewlett Packard LC/MSD 1100 system using APCI or electrospray sources either in negative mode or positive mode.

Nuclear magnetic resonance (NMR) spectra were recorded on a Bruker AMX-II-500 equipped with a reversed or QNP probe. Samples were dissolved in deuterochloroform ($CDCl_3$), deuteroacetone (acetone-$d_6$), deuteromethanol ($CD_3OD$) or deuterodimethylsulfoxide (DMSO-$d_6$) for data acquisition using tetramethylsilane as internal standard. Chemical shifts (δ) are expressed in parts per million (ppm), the coupling constants (J) are expressed in hertz (Hz) whereas multiplicities are denoted as s for singlet, d for doublet, 2d for two doublets, dd for doublet of doublets, t for triplet, q for quartet, quint. for quintet, m for multiplet, and br s for broad singlet.

GENERAL PROCEDURES

General Procedure for the Preparation of Test Compounds

A. General Coupling Procedure with HOBt and EDAC

Method Used in Scheme 1 of This Invention.

To the acid to be condensed (0.8 eq.) and 1-hydroxybenzotriazole (25 mg, 0.18 mmol, 1.2 eq.) in solution in 1 mL of dichloromethane and few drops of dimethylformamide, the minimum as to solubilize the reagents, was added 1-[3-(dimethylamino)propyl]-3-ethylcarbodiimide hydrochloride (EDAC) (26 mg, 0.14 mmol, 0.9 eq). The mixture was stirred for 15 min before addition of the amine ((1S)-4-amino-N-(4-amino-1-hydroxymethyl-butyl)-N-isobutyl-benzenesulfonamide (VII, example 1, step F)) (50 mg, 0.15 mmol) in 1 mL DMF. The resulting mixture was stirred for several hours, generally overnight, before pouring into an extraction funnel containing 15 mL hydrochloric acid 1.0 N and 30 mL ethyl acetate and extracted. The organic layers were washed with 20 mL of water, dried over magnesium sulfate, filtered and evaporated. The crude mixture was purified by reverse phase semi-preparative HPLC under the conditions described in the materials and methods section. The fractions containing the desired compound were combined and evaporated. The residue was taken up in a minimal amount of acetonitrile, diluted with water and lyophilized.

B. General Coupling Procedure with HOBt and EDAC

Method Used in Scheme 2 of this Invention.

To a suitable vessel was added 100 mg N-substituted amino acids, and a 1 mL aliquot of DMF, 150 mg EDAC, 75 mg HOBt were added. After 30 min at 40° C. 1.5 eq. of the amino alcohol, (1S)-4-amino-N-(5-amino-1-hydroxymethyl-pentyl)-N-isobutyl-benzenesulfonamide (XII, example 28, step D) was added along with 100 mg N-methyl morpholine. The solution was then stirred at 23° C. for 4–12 h. A 1M $K_2CO_3$ (20 mL aliquot) is added and left for 1 h. Then, EtOAc is added (50 mL). The aqueous phase is separated and extracted with citric acid (10%) 50 mL. The organic phase was separated and evaporated. The residue was purified by semi-preparative HPLC and lyophilized.

C. Preparation of Amides Using Acid Chlorides

To the amine (VII) dissolved in dichloromethane and N,N-dimethylformamide (DMF), the minimum as to dissolve the product, were added 1.5 eq. of diisopropylethylamine and the mixture cooled in an ice bath under stirring for 10–15 min. The acid chloride (1.1 eq.) was added dropwise and the reaction continued at 0° C. for 20–30 min and at room temperature an additional 2–4 hours. The reaction mixture was poured into an extraction funnel containing aqueous 1.0N sodium hydroxide and EtOAc and separated. The organic layer was washed with 1.0N hydrochloric acid, with brine, and then dried over magnesium sulfate. The crude product obtained after evaporation was generally purified by semi-preparative HPLC as described earlier (see materials and methods section).

D. Alternative Procedure for the Preparation of Amide Derivatives From Acid Chloride In a dried flask and under nitrogen atmosphere, dry acetonitrile (1 mL), triethylamine (4 eq.) and N-hydroxybenzotriazole (1.2 eq.) were added and stirred at room temperature. The corresponding acid chloride (1.1 eq.) was added slowly and the mixture was stirred for 30 minutes. The amine (product of example 8 (1 eq.) or other appropriate amine) was then added and the mixture was stirred until completion by TLC (100% EtOAc). The mixture was poured into an extracting funnel containing 50 mL of ethyl acetate. The organic layers were washed with water, saturated $NaHCO_3$ and brine, dried over sodium sulfate, filtered and evaporated. The crude mixture was purified by flash chromatography with 100% AcOEt.

E. General Procedure for the Preparation of Amide Derivatives From Acid

N-Hydroxybenzotriazole (1.9 eq.), 1-[3-(dimethylamino) propyl]-3-ethylcarbodiimide hydrochloride (EDAC) (2.5 eq.) and the corresponding carboxylic acid (0.8 eq.) were added to 1 mL of N,N-dimethylformamide and stirred at room temperature for 30–60 minutes. The amine (product of example 8 (1 eq.) or other appropriate amine) was then added and the mixture was stirred until completion by TLC (100% EtOAc). The mixture was poured into an extracting funnel with 50 mL of ethyl acetate. The organic layers were washed with water, saturated $NaHCO_3$ and brine, dried over sodium sulfate, filtered and evaporated. The crude mixture was purified by flash chromatography with 100% EtOAc.

F. General Procedure for the Preparation of Secondary Amine Derivatives From Aldehydes (5S)-2-Amino-N-{5-[(4-amino-benzenesulfonyl)-isobutyl-amino]-6-hydroxy-hexyl}-3-naphthalen-2-yl-propionamide (or the product of example 8 for the ornithine derivatives or other amine) (1.0 eq.) was added to dichloromethane (1 mL) and stirred at 0° C. The corresponding aldehyde (1.0 eq.) and acetic acid (1.0 eq.) were added to the mixture. After stirring for 10 minutes, sodium triacetoxyborohydride (1.5 eq.) was added and the mixture stirred until completion by TLC (100% EtOAc). The solvent was evaporated and the crude mixture was purified by reverse phase semi-preparative HPLC under the conditions described in the Materials and Methods section.

G. General Procedure for the Preparation of Carbamates From Alcohols

In a dried flask and under inert atmosphere, the alcohol was dissolved in dry dichloromethane (0.2M) and dissuccinimidyl carbonate (1.0 eq.) was added. The mixture was stirred at room temperature for 2–3 hours before addition of the solid amine. The mixture was stirred an additional hour and then poured in an extraction funnel containing 1.0N sodium hydroxide and ethyl acetate and extracted. The organic layer was washed with a 1.0N hydrochloric acid solution (if the alcohol moiety do not bear a basic site) and with brine, dried with magnesium sulphate, filtered and evaporated to dryness. The crude residue was then purified by semi-preparative HPLC using the conditions described in the Materials and Methods section.

DETAILED DESCRIPTION OF THE INVENTION

EXAMPLES

Specific Examples for the Preparation of Derivatives of General Formula I

The following compounds were prepared from either L-lysine or L-ornithine derivatives using the procedures summarized in schemes 1, 2, 3 and 4.

Example 1

Preparation of (1S,4S)-(1-{4-[(4-Amino-benzenesulfonyl)-isobutyl-amino]-5-hydroxy-pentylcarbamoyl}-2-naphthalen-2-yl-ethyl)-carbamic Acid Methyl Ester (MX-61)

The preparation of the title compound is based on scheme 1 of this invention.

Step A. Preparation of L-Methyl Nε-benzyloxycarbonyl-ornithinoate (II)

To a stirred suspension of Nε-Z-ornithine (I) (5.0 g, 18.8 mmol.) in ice cooled methanol (50 mL) were cannulated 5.95 mL of chlorotrimethylsilane (47 mmol., 2.5 eq.). The ice bath was removed and the precipitate slowly solubilized. The mixture was than heated to reflux for few hours until completion. This is verified by regular aliquot NMR analysis. The mixture is then evaporated to dryness and the residue taken up with sodium carbonate (120 mL) and ethyl acetate (200 mL) and extracted. The organic layers washed with brine, dried over magnesium sulfate, filtered, evaporated and dried under vacuum to give 4.31 g (72%) of clear liquid. The ester was used without further purification for the next step.

$^1$H NMR (DMSO-$d_6$): δ 1.37–1.49 (m, 3H), 1.50–1.57 (m, 1H), 1.79 (br s, 2H), 2.95–2.98 (m, 2H), 3.26–3.29 (m, 1H), 3.60 (s, 3H), 5.00 (s, 2H), 7.26 (t, J=5.3, 1H), 7.29–7.37 (m, 5H).

Step B. Preparation of L-Methyl Nα-(4-nitrobenzenesulfonyl)-Nε-benzyloxycarbonyl-ornithinoate (III)

L-Methyl Nε-benzyloxycarbonyl-ornithinoate (II) (3.5 g, 12.5 mmol) and triethylamine (3.5 mL, 25 mmol, 2 eq.) in 100 mL dichloromethane (DCM) were cooled using an ice bath. 4-nitrobenzenesulfonyl chloride 90% (3.7 g, 15 mmol, 1.2 eq. ) was slowly added portionwise over 10 min. The ice bath was removed and the reaction continued for an additional hour under stirring. The mixture was poured into an extraction funnel containing 100 mL $CH_2Cl_2$ and 50 mL hydrochloric acid 1.0 N and separated. The organic layers were washed with brine, dried over magnesium sulfate, filtered, evaporated and dried in vacuo to give 5.6 g (96%) of brown solid (TLC: Rf=0.43, 50% EtOAc/hexanes).

$^1$H NMR (DMSO-$d_6$): δ 1.28–1.40 (m, 2H), 1.47–1.45 (m, 1H), 1.60–1.66 (m, 1H), 2.89–2.93 (m, 2H), 3.38 (s, 3H), 3.86–3.91 (m, 1H), 4.99 (s, 2H), 7.20 (t, J=5.4, 1H), 7.28–7.37 (m, 5H), 8.00 (d, J=8.7, 2H), 8.39 (d, J=8.7, 2H), 8.72 (d, J=8.7, 1H).

Step C. Preparation of L-Methyl Nα-(4-nitrobenzenesulfonyl)-Nα-isobutyl-Nε-benzyloxycarbonyl-ornithinoate (IV)

The sulfonamide (III) (5.0 g, 10.7 mmol), 2-methyl-1-propanol (1.2 mL, 13.0 mmol, 1.2 eq.) and triphenylphosphine (3.4 g, 13.0 mmol, 1.2 eq.) were successively added in 50 mL anhydrous tetrahydrofuran. The mixture was stirred and diethylazodicarboxylate (DEAD, 2.1 mL, 13.3 mmol, 1.2 eq.) was added dropwise over 5 min. The reaction was pursued overnight at room temperature under stirring. The solvent was evaporated and the residue purified by flash chromatography (10 to 30% EtOAc/hexanes). The pure compound (5.07 g, 91%) was isolated as yellow oil (TLC: Rf=0.40, 40% EtOAc/hexanes, Indicator: CAM).

$^1$H NMR (DMSO-$d_6$): δ 0.79 (d, J=6.5, 3H), 0.83 (d, J=6.5, 3H), 1.35–1.37 (m, 2H), 1.54–1.62 (m, 2H), 1.82–1.90 (m, 2H), 2.88 (dd, J=7.7, 14.6, 1H), 2.92–3.00 (m, 2H), 2.03 (dd, J=7.1, 14.3, 1H), 3.42 (s, 3H), 4.42–4.45 (m, 1H), 4.99 (s, 2H), 7.25 (t, J=5.5, 1H), 7.28–7.37 (m, 5H), 8.08 (d, J=8.7, 2H), 8.39 (d, J=8.7, 2H).

Step D. Preparation of L-Methyl Nα-(4-aminobenzenesulfonyl)-Nα-isobutyl-Nε-benzyloxycarbonyl-ornithinoate (V)

To the nitro compound (IV) (3.18 g, 6.1 mmol) in 40 mL denatured ethanol were added 3.03 g (12.2 mmol, 2 eq.) nickel acetate tetrahydrate. The suspension was vigorously stirred for 10 min and sodium borohydride (0.5 g, 13 mmol, 2eq.) was added portionwise (as to control effervescence) over 15 min. The resulting mixture is stirred until the reduction was completed as shown by TLC (30 min). 30 mL of water were added to quench the excess hydride and stirred for 40 min and the resulting slurry evaporated to dryness. The residue was taken up with methanol and 30 g of silica gel added before evaporating the suspension again. This drypack was placed over a flash chromatography column containing about 40 g of silica and conditioned in ethyl acetate. The compound was eluted using the same solvent and the fractions of interest grouped and evaporated to give pure product as a brown oil (2.90 g, 97%) (TLC: Rf=0.37, 60% EtOAc/hexanes, pink vs ninhydrin).

LC-MS: 492.1 (M+H)$^+$, >98% pure; $^1$H NMR (DMSO-$d_6$): δ 0.84 (d, J=6.6, 3H), 0.85 (d, J=6.6, 3H), 1.49–1.67 (m, 3H), 1.88–1.99 (m, 2H), 2.93 (dd, J=7.8, 14.6, 1H), 3.00 (dd, J=7.1, 14.6, 1H), 3.14–3.18 (m, 2H), 3.51 (s, 3H), 4.37 (t, J=7.4, 1H), 5.06 (s, 2H), 5.45 (s, 2H), 6.34 (t, J=5.0, 1H), 6.73 (d, J=8.6, 2H), 7.28–7.36 (m, 5H), 7.50 (d, J=8.6, 2H).

Step E. Preparation of (4S)-{4-[(4-Aminobenzenesulfonyl)-isobutyl-amino]-5-hydroxy-pentyl}-carbamic Acid Benzyl Ester (VI)

To the ester (V) (4.83 g, 9.8 mmol) in 80 mL denatured anhydrous ethanol at room temp. and under vigorous agitation were added portionwise over 1 hour lithium borohydride (900 mg, 41 mmol, 4 eq.). The resulting mixture was stirred overnight and 50 mL of water were added. After 1 hour the solvent was evaporated and the residue taken up in 200 mL ethyl acetate and 100 mL water and extracted. The organic layers were washed with brine, dried over magnesium sulfate and concentrated in vacuo. The isolated compound (4.55 g, quantitative) showed to be pure from NMR analysis. (TLC: Rf=0.39, 75% EtOAc/hexanes, pink vs ninhydrin).

LC-MS: 464.2 (M+H)$^+$, >95% pure; $^1$H NMR (DMSO-$d_6$): δ 0.79 (d, 6.0, 3H), 0.81 (d, J=6.0, 3H), 1.19–1.31 (m, 2H), 1.32–1.40 (m, 1H), 1.53–1.59 (m, 1H), 1.81–1.86 (m, 1H), 2.73 (dd, J=7.1, 14.3, 1H), 2.83 (dd, J=7.7, 14.3, 1H), 2.87–2.93 (m, 2H), 3.19–3.24 (m, 1H), 3.28–3.30 (m, 1H), 3.45–3.49 (m, 1H), 4.60 (t, J=5.1, 11H), 5.00 (s, 2H), 5.91 (s, 2H), 6.58 (d, J=8.6, 2H), 7.19 (t, J=5.5, 1H), 7.28–7.36 (m, 5H), 7.38 (d, J=8.6, 2H).

Step F. Preparation of (1S)-4-Amino-N-(4-amino-1-hydroxymethyl-butyl)-N-isobutyl-benzenesulfonamide (VII)

To 2.21 g of the carbamate (VI) (4.8 mmol) in 25 mL of methanol were added 230 mg of palladium on carbon 10%. The flask was closed by use of a septum through witch a needle was connected to a balloon filled with hydrogen. The septum was also pierced using a 26 gauge needle serving as an exhaust in order to generate a stream of gas over the solution. The suspension was stirred for 2 hours using 3 fills of balloons before disappearance of starting material from TLC. The mixture was filtered on a pad of celite, washed with methanol and the filtrate evaporated and dried under vacuum. This gave quantitatively (1.57 g) the free amine as a brownish foam.

This is the amine used as starting material for a series of test compounds (VIII) (see general procedure A).

$^1$H NMR (DMSO-$d_6$): δ 0.81 (d, J=6.1, 3H), 0.83 (d, J=6.1, 3H), 1.09–1.28 (m, 3H), 1.53–1.60 (m, 1H), 1.81–1.89 (m, 1H), 2.40 (t, J=6.7, 2H), 2.74 (dd, J=6.1, 14.3, 1H), 2.86 (dd, J=7.8, 14.3, 1H), 3.24 (dd, J=6.9, 10.7, 1H), 3.34 (dd, J=5.3, 10.7, 1H), 3.44–3.49 (m, 1H), 5.90 (s, 2H), 6.59 (d, J=8.6, 2H), 7.39 (d, J=8.6, 2H). $^{13}$C NMR (DMSO-$d_6$): δ 21.4, 21.5, 28.1, 29.5, 31.9, 42.9, 52.9, 61.1, 64.1, 114.0, 127.1, 130.1, 153.9. [α]$_D$, 25° C.: –1.7° (c=1.9, $CH_3OH$).

Step G. Preparation of the Final Test Compound:

The title compound, (1S,4S)-(1-{4-[(4-aminobenzenesulfonyl)-isobutyl-amino]-5-hydroxy-pentylcarbamoyl}-2-naphthalen-2-yl-ethyl)-carbamic acid methyl ester, was prepared from general procedure A using (2S)-2-methoxycarbonylamino-3-naphthalen-2-yl-propionic acid and amine intermediate VII. The final product was obtained in 60% yield. Rf=0.39, EtOAc 100%.

LC-MS: 585.3 (M+H)$^+$, >98% pure; $^1$H NMR (CD$_3$OD): δ 0.88 (d, J=6.6, 3H), 0.89 (d, J=6.6, 3H), 1.12–130 (m, 3H), 1.32–1.43 (m, 1H), 1.81–1.88 (m, 1H), 2.81 (dd, J=7.0, 14.4, 1H), 2.91 (dd, J=7.9, 14.4, 1H), 2.99–3.02 (m, 2H), 3.05 (dd, J=8.5, 13.6, 1H), 3.22 (dd, J=6.6, 13.6, 1H), 3.29–3.32 (m, 1H), 3.45 (dd, J=5.7, 10.8, 1H), 3.47–3.58 (m, 1H), 3.58 (s, 3H), 4.39 (t, J=7.3, 1H), 6.67 (d, J=8.7, 2H), 7.39 (d, J=8.5, 1H), 7.43–7.48 (m, 2H), 7.47 (d, J=8.7, 2H), 7.69 (s, 1H), 7.80–7.84 (m, 3H).

Example 2

Preparation of (1S,4S)-(1-{4-[(4-Amino-benzenesulfonyl)-isobutyl-amino]-5-hydroxy-pentylcarbamoyl}-2-naphthalen-1-yl-ethyl)-carbamic Acid Methyl Ester (MX-62)

The title compound was prepared from general procedure A using (2S)-2-methoxycarbonylamino-3-naphthalen-1-ylpropionic acid and amine intermediate VII. The final product was obtained in 76% yield. Rf=0.57, EtOAc 100%.

LC-MS: 585.3 (M+H)⁺, >97% pure; $^1$H NMR (CD$_3$OD): δ 0.89 (d, J=6.5, 3H), 0.90 (d, J=6.5, 3H), 1.12–1.33 (m, 3H), 1.39–1.49 (m, 1H), 1.86–1.93 (m, 1H), 2.84 (dd, J=7.1, J=14.5, 1H), 2.94 (dd, J=7.9, 14.5, 1H), 2.92–3.01 (m, 3H), 3.29–3.34 (m, 1H), 3.38 (dd, J=6.5,10.5, 1H), 3.49–3.61 (m, 3H), 3.58 (s, 3H), 4.44 (t, J=7.5, 1H), 6.68 (d, J=8.6, 2H), 7.36 (d, J=6.8, 1H), 7.41 (t, J=7.5, 1H), 7.48–7.51 (m, 1H), 7.49 (d, J=8.6, 2H), 7.56 (t, J=7.5, 1H), 7.78 (d, J=8.1, 1H), 7.88 (d, J=8.1, 1H), 8.20 (d, J=8.3, 1H).

Example 3

Preparation of (1R,S,4S)-(1-{4-[(4-Amino-benzenesulfonyl)-isobutyl-amino]-5-hydroxy-pentylcarbamoyl}-2-biphenyl-2-yl-ethyl)-carbamic Acid Methyl Ester (MX-63)

The title compound was prepared from general procedure A using (2R,S)-3-biphenyl-2-yl-2-methoxycarbonylamino-propionic acid and amine intermediate VII. The final product was obtained in 76% yield. Rf=0.59, EtOAc 100%.

LC-MS: 611.3 (M+H)⁺, >95% pure; $^1$H NMR (CD$_3$OD): δ 0.89 (d, J=6.3, 3H), 0.90 (d, J=6.3, 3H), 1.19–1.37 (m, 3H), 1.45–1.56 (m, 1H), 1.86–1.94 (m, 1H), 2.82–2.87 (m, 2H), 2.92–3.04 (m, 3H), 3.13 (dd, J=6.0, 14.0, 1H), 3.40 (dd, J=6.8, 10.9, 1H), 3.48–3.60 (m, 2H), 3.55 (s, 3H), 4.11 (t, J=6.9, 1H), 6.69 (d, J=8.7, 2H), 7.18 (d, J=6.9, 1H), 7.26–7.40 (m, 6H), 7.42–7.46 (m, 2H), 7.50 (d, J=8.7, 2H).

Example 4

Preparation of (1S,4S)-Morpholine-4-carboxylic Acid (1-{4-[(4-Amino-benzenesulfonyl)-isobutyl-amino]-5-hydroxy-pentylcarbamoyl}-2-naphthalen-1-yl-ethyl)-amide (MX-99)

The title compound was prepared from general procedure A using (2S)-2-[(morpholine-4-carbonyl)-amino]-3-naphthalen-1-yl-propionic acid and amine intermediate VII. The final product was obtained in 11% yield.

LC-MS: 640.3 (M+H)⁺, >98% pure; $^1$H NMR (DMSO-d$_6$): δ 0.79 and 0.81 (d, J=6.8, 2×3H), 1.20–1.30 (m, 2H), 1.31–1.42 (m, 1H), 1.49–1.60 (m, 1H), 1.80–1.92 (m, 1H), 2.74 (dd, J=7.2, 14.2, 1H), 2.85 (dd, J=7.5, 14.2, 1H), 2.94–3.05 (m, 2H), 3.10–3.60 (m, 11H), 4.39–4.47 (m, 1H), 5.75 (s, 2H), 6.57–6.62 (m, 3H), 7.38–7.41 (m, 4H), 7.50 (t, J=7.2, 1H), 7.55 (t, J=7.3), 7.77 (d, J=7.0, 7.86–7.91 (m, 2H), 8.22 (d, J=8.3, 1H).

Example 5

Preparation of (2S,4S)-N-{4-[(4-Amino-benzenesulfonyl)-isobutyl-amino]-5-hydroxy-pentyl}-2-[2-(4-methoxy-phenyl)-acetylamino]-3-naphthalen-1-yl-propionamide (MX-120)

The title compound was prepared from general procedure A using (2S)-2-[2-(4-methoxy-phenyl)-acetylamino]-3-naphthalen-1-yl-propionic acid. The final product was obtained in 5% yield.

LC-MS: 675.3 (M+H)⁺, >95% pure.

Example 6

Preparation of (1S,4S)-[1-{4-[(4-Amino-benzenesulfonyl)-isobutyl-amino]-5-hydroxy-pentylcarbamoyl}-2-(4'-methoxy-biphenyl-2-yl)-ethyl]-carbamic Acid Methyl Ester (MX-121)

The title compound was prepared from general procedure A using (2S)-3-(4'-methoxy-biphenyl-2-yl)-2-methoxycarbonylamino-propionic acid. The final product was obtained in 34% yield.

LC-MS: 641.2 (M+H)⁺, >98% pure.

Example 7

Preparation of (1S,4S)-(1-{4-[(4-Amino-benzenesulfonyl)-isobutyl-amino]-5-hydroxy-pentylcarbamoyl}-2-naphthalen-1-yl-ethyl)-carbamic Acid 2,2,2-Trifluoro-ethyl Ester (MX-124)

To a stirred solution of (2S,4S)-2-amino-N-{4-[(4-amino-benzenesulfonyl)-isobutyl-amino]-5-hydroxy-pentyl}-3-naphthalen-1-yl-propionamide (0.09 g, 0.17 mmol, product of example 8) in K$_2$CO$_3$ 1M (3 mL) and THF (1 mL) was added carbonic acid 2,5-dioxo-pyrrolidin-1-yl ester 2,2,2-trifluoroethyl ester (0.05 g, 0.20 mmol), prepared from 2,2,2-trifluoroethanol, N,N'-disuccinimidyl carbonate and triethylamine in tetrahydrofuran. The mixture was stirred to room temperature for 24 h. Ethyl acetate was added and the organic layer was washed with water, then dried with MgSO$_4$ and concentrated. The residue was purified by flash chromatography eluting with a mixture of hexane/EtOAc. The yield obtained was 10%.

LC-MS: 653.2 (M+H)⁺, >98% pure; $^1$H NMR (CD$_3$OD): δ 0.88 (2d, J=6.2, 6H), 1.22 (m, 4H), 1.40 (m, 1H), 1.89 (m, 1H), 2.82 (dd, J=7.1, 14.3, 1H), 2.94 (m, 3H), 3.36 (m, 2H), 3.50 (m, 2H), 3.59 (dd, J=7.1, 13.9, 1H), 4.45 (m, 2H), 6.66 (d, J=8.8, 2H), 7.38 (m, 2H), 7.48 (m, 3H), 7.54 (d, J=7.8, 1H), 7.77 (d, J=8.0, 1H), 7.87 (d, J=8.0, 1H), 8.18 (d, J=8.3, 1H).

Example 8

Preparation of (2S,4S)-2-Amino-N-{4-[(4-amino-benzenesulfonyl)-isobutyl-amino]-5-hydroxy-pentyl}-3-naphthalen-1-yl-propionamide (MX-143)

The title compound was prepared from (1S,4S)-(1-{4-[(4-amino-benzenesulfonyl)-isobutyl-amino]-5-hydroxy-pentylcarbamoyl}-2-naphthalen-1-yl-ethyl)-carbamic acid tert-butyl ester as described for the preparation of (2S,5S)-2-amino-N-{5-[(4-amino-benzenesulfonyl)-isobutyl-amino]-6-hydroxy-hexyl}-3-naphthalen-2-yl-propionamide (example 49). The final product was obtained in 94% yield.

LC-MS: 527.81 (M+H)⁺, >95% pure; $^1$H NMR (CD$_3$OD): δ 0.88 (2d, J=6.5, 6H), 1.20 (m, 3H), 1.41 (m, 1H), 1.87 (m, 1H), 2.82 (dd, J=7.1, 14.3, 1H), 2.93 (m, 3H), 3.21 (dd, J=7.1, 13.4, 1H), 3.41 (m, 1H), 3.50 (m, 3H), 3.63 (d, J=7.2, 1H), 6.66 (d, J=8.4, 2H), 7.35 (d, J=7.0, 1H), 7.42 (m, 1H), 7.47 (m, 3H), 7.53 (m, 1H), 7.77 (d, J=8.0, 1H), 7.87 (d, J=8.0, 1H), 8.17 (d, J=8.3, 1H).

Example 9

Preparation of (1S,4S)-Morpholine-4-carboxylic Acid (1-{4-[(4-Amino-benzenesulfonyl)-isobutyl-amino]-5-hydroxy-pentylcarbamoyl}-2,2-diphenyl-ethyl)-amide (MX-151)

The title compound was prepared from general procedure A using (2S)-2-[(morpholine-4-carbonyl)-amino]-3,3-diphenyl-propionic acid and amine intermediate VII. The final product was obtained in 36% yield. Rf=0.15 EtOAc 100%.

LC-MS: 666.3 (M+H)⁺, >98% pure; $^1$H NMR (CD$_3$OD): δ 0.89 and 0.90 (2d, J=6.1, 2×3H), 0.98–1.20 (m, 3H), 1.24–1.38 (m, 1H), 1.84–1.96 (m, 1H), 2.74–2.87 (m, 3H), 2.92 (dd, J=7.7, 14.5, 1H), 3.08–3.17 (m, 2H), 3.20–3.53 (m, 11H), 4.39 (d, J=11.3, 1H), 5.05 (d, J=11.3, 1H), 6.69 (d, J=8.5, 2H), 7.18–7.21 (m, 2H), 7.25–7.36 (m, 8H), 7.49 (d, J=8.5, 2H).

Example 10

Preparation of (1S,4S)-(1-{4-[(4-Amino-benzenesulfonyl)-isobutyl-amino]-5-hydroxy-pentylcarbamoyl}-2,2-diphenyl-ethyl)-carbamic Acid Methyl Ester (MX-152)

The title compound was prepared from general procedure A using (2S)-2-methoxycarbonylamino-3,3-diphenyl-propionic acid (see example 34, step A) and amine intermediate VII. The final product was obtained in 74% yield. Rf=0.57 EtOAc 100%.

LC-MS: 611.2 (M+H)$^+$, >98% pure; $^1$H NMR (CD$_3$OD): δ 0.89 and 0.90 (2d, J=6.2, 2×3H), 0.97–1.20 (m, 3H), 1.27–1.38 (m, 1H), 1.84–1.95 (m, 1H), 2.72–2.81 (m, 2H), 2.82 (dd, J=7.1, 14.5, 1H), 2.91 (dd, J=7.7, 14.3, 1H), 3.37 (dd, J=6.6, 10.9, 1H), 3.42–3.52 (m, 2H), 3.55 (s, 3H), 4.30 (d, J=11.4, 1H), 4.90 (d, J=11.4, 1H), 6.70 (d, J=8.5, 2H), 7.15–7.22 (m, 2H), 7.23–7.32 (m, 6H), 7.35 (d, J=7.6, 2H), 7.49 (d, J=8.5, 2H).

Example 11

Preparation of (1S,4S)-N-(1-{4-[(4-Amino-benzenesulfonyl)-isobutyl-amino]-5-hydroxy-pentylcarbamoyl}-2-naphthalen-1-yl-ethyl)-oxalamic Acid Methyl Ester (MX-165)

The title compound was prepared from (2S,4S)-2-amino-N-{4-[(4-amino-benzenesulfonyl)-isobutyl-amino]-5-hydroxy-pentyl}-3-naphthalen-1-yl-propionamide (see example 8) as described in general procedure D using methyl chlorooxoacetate. The final product was obtained in 75% yield.

LC-MS: 613.3 (M+H)$^+$, >85% pure; $^1$H NMR (CD$_3$OD): δ 0.88 (2d, J=6.2, 6H), 1.22 (m, 4H), 1.43 (m, 1H), 1.87 (m, 1H), 2.83 (dd, J=7.1, 14.5, 1H), 2.96 (m, 3H), 3.36 (m, 1H), 3.52 (m, 3H), 3.66 (dd, J=7.1, 14.0, 1H), 3.82 (s, 3H), 6.66 (d, J=8.8, 2H), 7.38 (m, 2H), 7.48 (m, 3H), 7.54 (m, 1H), 7.76 (d, J=8.0, 1H), 7.86 (d, J=8.0, 1H), 8.20 (d, J=8.3, 1H).

Example 12

Preparation of (1S,4S)-N-(1-{4-[(4-Amino-benzenesulfonyl)-isobutyl-amino]-5-hydroxy-pentylcarbamoyl}-2-naphthalen-1-yl-ethyl)-3,3,3-trifluoro-propionamide (MX-169)

The title compound was prepared from (2S,4S)-2-amino-N-{4-[(4-amino-benzenesulfonyl)-isobutyl-amino]-5-hydroxy-pentyl}-3-naphthalen-1-yl-propionamide (see example 8) as described in general procedure E using 3,3,3-trifluoropropionic acid. The final product was obtained in 76% yield.

LC-MS: 637.3 (M+H)$^+$, >98% pure; $^1$H NMR (CD$_3$OD): δ 0.87 (2d, J=6.4, 6H), 1.21 (m, 3H), 1.38 (m, 1H), 1.88 (m, 1H), 2.82 (dd, J=7.1, 14.3, 1H), 2.91 (m, 3H), 3.19 (m, 2H), 3.37 (m ,2H), 3.48 (m, 3H), 4.72 (t, J=7.3, 1H), 6.65 (d, J=8.8, 2H), 7.34 (m, 1H), 7.39 (m, 1H), 7.48 (m, 3H), 7.55 (m, 1H), 7.76 (d, J=8.0, 1H), 7.86 (d, J=8.0, 1H), 8.19 (d, J=8.3, 1H).

Example 13

Preparation of (1S,4S)-Cyclohexanecarboxylic Acid (1-{4-[(4-Amino-benzenesulfonyl)-isobutyl-amino]-5-hydroxy-pentylcarbamoyl}-2-naphthalen-1-yl-ethyl)-amide (MX-171)

The title compound was prepared from (2S,4S)-2-amino-N-{4-[(4-amino-benzenesulfonyl)-isobutyl-amino]-5-hydroxy-pentyl}-3-naphthalen-1-yl-propionamide (see example 8) as described in general procedure D using cyclohexanecarbonyl chloride. The final product was obtained in 74% yield.

LC-MS: 637.3 (M+H)$^+$, >98% pure; $^1$H NMR (CD$_3$OD): δ 0.88 (2d, J=6.4, 6H), 1.27 (m, 7H), 1.44 (m, 1H), 1.56 (m, 1H), 1.63 (m, 1H), 1.71 (m, 3H), 1.88 (m, 1H), 2.16 (m, 1H), 2.83 (dd, J=7.2, 14.5, 1H), 2.93 (dd, J=7.5, 14.3, 1H), 2.98 (m, 2H), 3.35 (m, 2H), 3.52 (m, 3H), 4.71 (m, 1H), 6.66 (d, J=8.8, 2H), 7.37 (m, 2H), 7.48 (m, 3H), 7.55 (m, 1H), 7.71 (t, J=5.2, 1H), 7.75 (d, J=8.0, 1H), 7.85 (m, 1H), 8.20 (d, J=8.3, 1H).

Example 14

Preparation of (2S,4S)-2-Amino-N-{4-[(4-amino-benzenesulfonyl)-isobutyl-amino]-5-hydroxy-pentyl}-3-biphenyl-2-yl-propionamide (MX-172)

The title compound was prepared from (1S,4S)-(1-{4-[(4-amino-benzenesulfonyl)-isobutyl-amino]-5-hydroxy-pentylcarbamoyl}-2-biphenyl-2-yl-ethyl)-carbamic acid tert-butyl ester as described for the acid hydrolysis of (1S,5S)-(1-{5-[(4-amino-benzenesulfonyl)-isobutyl-amino]-6-hydroxy-hexylcarbamoyl}-2-naphthalen-2-yl-ethyl)-carbamic acid tert-butyl ester (see example 49). The final product was obtained in 90% yield.

LC-MS: 553.3 (M+H)$^+$, >95% pure; $^1$H NMR (CD$_3$OD): δ 0.88 (m, 6H), 1.24 (m, 2H), 1.30 (m, 2H), 1.48 (m, 1H), 1.90 (m, 1H), 2.83 (m, 2H), 2.97 (m, 4H), 3.39 (m, 1H), 3.50 (m, 1H), 3.55 (m, 1H), 6.67 (d, J=8.2, 2H), 7.18 (d, J=7.2, 1H), 7.32 (m, 6H), 7.42 (d, J=7.1, 2H), 7.49 (d, J=8.3, 2H).

Example 15

Preparation of (1S,4S)-(1-{4-[(4-Amino-benzenesulfonyl)-isobutyl-amino]-5-hydroxy-pentylcarbamoyl}-2-naphthalen-1-yl-ethylamino)-acetic Acid Methyl Ester (MX-173)

To a stirred solution of (2S,4S)-2-amino-N-{4-[(4-amino-benzenesulfonyl)-isobutyl-amino]-5-hydroxy-pentyl}-3-naphthalen-1-yl-propionamide (product of example 8) (0.023 g, 0.044 mmol) in DMF (0.7 mL) was added triethylamine (12.0 μL, 0.087 mmol) and methyl bromoacetate (4.0 μL, 0.054 mmol). The mixture was stirred to room temperature for 1 h. Ethyl acetate was added and the organic layer was washed with a saturated solution of NaHCO$_3$, then dried with MgSO$_4$ and concentrated. The residue was purified by flash chromatography eluting with a mixture of hexane/EtOAc. The yield obtained was 47%.

LC-MS: 599.3 (M+H)$^+$, >95% pure; $^1$H NMR (CD$_3$OD): δ 0.90 (m, 6H), 1.20 (m, 1H), 1.29 (m, 2H), 1.45 (m, 1H), 1.90 (m, 1H), 2.85 (m, 1H), 2.98 (m, 3H), 3.31 (m, 3H), 3.39 (m, 1H), 3.52 (m, 7H), 6.66 (d, J=8.8, 2H), 7.38 (d, J=6.8, 1H), 7.43 (m, 1H), 7.51 (m, 3H), 7.57 (m, 1H), 7.80 (d, J=7.9, 1H), 7.89 (d, J=8.0, 1H), 8.20 (d, J=8.3, 1H).

Example 16

Preparation of (1S,4S)-(1-{4-[(4-Amino-benzenesulfonyl)-isobutyl-amino]-5-hydroxy-pentylcarbamoyl}-2,2-diphenyl-ethyl)-carbamic Acid tert-Butyl Ester (MX-174)

The title compound was prepared from general procedure A using (2S)-2-tert-butoxycarbonylamino-3,3-diphenyl-propionic acid. The final product was obtained in quantitative yield.

LC-MS: 653.4 (M+H)$^+$, >95% pure; $^1$H NMR (CD$_3$OD): δ 0.89 and 0.90 (2d, J=6.2, 2×3H), 0.98–1.07 (m, 1H), 1.07–1.23 (m, 2H), 1.33 (s, 9H), 1.35–1.45 (m, 1H), 1.85–1.95 (m, 1H), 2.82 (dd, J=7.2, 14.3, 1H), 2.76–2.85 (m, 2H), 2.92 (dd, J=7.6, 14.3, 1H), 3.47 (d, J=11.2, 1H), 4.28 (d, J=11.2, 1H), 6.70 (d, J=8.8, 2H), 7.15–7.23 (m, 2H), 7.23–32 (m, 6H), 7.35 (d, J=7.6, 2H), 7.49 (d, J=8.8, 2H).

Example 17

Preparation of (1S,4S)-(1-{4-[(4-Amino-benzenesulfonyl)-isobutyl-amino]-5-hydroxy-pentylcarbamoyl}-2-naphthalen-1-yl-ethyl)-carbamic Acid 2-Methoxy-ethyl Ester (MX-175)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in example 7 using 2-methoxyethanol. The final product was obtained in 18% yield.

LC-MS: 629.2 (M+H)$^+$, >98% pure; $^1$H NMR (CD$_3$OD): δ 0.88 (2d, J=6.3, 6H), 1.18 (m, 1H), 1.24 (m, 2H), 1.44 (m, 1H), 1.88 (m, 1H), 2.83 (dd, J=6.9, 14.3, 1H), 2.96 (m, 3H), 3.35 (m, 4H), 3.38 (m, 1H), 3.51 (m, 4H), 3.60 (dd, J=6.5, 13.8, 1H), 4.08 (m, 2H), 4.44 (t, J=7.2, 1H), 6.66 (d, J=8.8, 2H), 7.38 (m, 2H), 7.48 (m, 3H), 7.54 (m, 1H), 7.76 (d, J=7.9, 1H), 7.86 (d, J=8.0, 1H), 8.18 (d, J=8.4, 1H).

Example 18

Preparation of (1S,4S)-(1-{4-[(4-Amino-benzenesulfonyl)-isobutyl-amino]-5-hydroxy-pentylcarbamoyl}-2-naphthalen-1-yl-ethyl)-carbamic Acid Ethyl Ester (MX-181)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure D using ethyl chloroformate. The final product was obtained in 60% yield.

LC-MS: 599.3 (M+H)$^+$, >98% pure; $^1$H NMR (CD$_3$OD): δ 0.88 (m, 7H), 1.16 (m, 3H), 1.28 (m, 2H), 1.43 (m, 1H), 1.89 (m, 1H), 2.83 (m, 1H), 2.93 (m, 3H), 3.37 (m, 1H), 3.54 (m, 3H), 3.99 (m, 2H), 4.43 (t, J=7.2, 1H), 6.67 (d, J=8.8, 2H), 7.38 (m, 2H), 7.48 (m, 3H), 7.55 (m, 1H), 7.76 (d, J=8.0, 1H), 7.86 (d, J=8.0, 1H), 8.18 (d, J=8.4, 1H).

Example 19

Preparation of (2S,4S)-N-{4-[(4-Amino-benzenesulfonyl)-isobutyl-amino]-5-hydroxy-pentyl}-2-(2-methoxy-acetylamino)-3-naphthalen-1-yl-propionamide (MX-182)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure E using methoxyacetic acid. The final product was obtained in 30% yield.

LC-MS: 599.3 (M+H)$^+$, 97% pure; $^1$H NMR (CD$_3$OD): δ 0.90 (2d, J=6.4, 6H), 1.26 (m, 3H), 1.46 (m, 1H), 1.90 (m, 1H), 2.85 (dd, J=8.2, 15.4, 1H), 2.98 (m, 3H), 3.33 (s, 3H), 3.39 (m, 1H), 3.45 (m, 1H), 3.51 (m, 1H), 3.55 (m, 1H), 3.60 (m, 1H), 3.76 (d, J=15.1, 1H), 3.88 (d, J=15.0, 1H), 4.78 (t, J=7.4, 1H), 6.68 (d, J=8.4, 2H), 7.37 (d, J=6.9, 1H), 7.43 (t, J=7.4, 1H), 7.51 (m, 3H), 7.58 (t, J=7.4, 1H), 7.79 (d, J=8.0, 1H), 7.88 (d, J=8.1, 1H), 8.23 (d, J=8.4, 1H).

Example 20

Preparation of (2S,4S)-N-{4-[(4-Amino-benzenesulfonyl)-isobutyl-amino]-5-hydroxy-pentyl}-2-butylamino-3-naphthalen-1-yl-propionamide (MX-183)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure F using butyraldehyde. The final product was obtained in 13% yield.

LC-MS: 583.3 (M+H)$^+$, >98% pure; $^1$H NMR (CD$_3$OD): δ 0.87 (m, 9H), 1.23 (m, 5H), 1.33 (m, 1H), 1.42 (m, 2H), 1.88 (m, 1H), 2.46 (m, 1H), 2.54 (m, 1H), 2.82 (dd, J=7.3, 14.5, 1H), 2.93 (m, 3H), 3.35 (m, 2H), 3.43 (m, 1H), 3.47 (m, 1H), 3.51 (m, 2H), 6.67 (d, J=8.8, 2H), 7.35 (d, J=6.9, 1H), 7.43 (t, J=7.2, 1H), 7.50 (m, 3H), 7.57 (t, J=7.1, 1H), 7.79 (d, J=8.2, 1H), 7.89 (d, J=8.1, 1H), 8.16 (d, J=8.4, 1H).

Example 21

Preparation of (1S,4S)-Acetic Acid 2-(1-{4-[(4-Amino-benzenesulfonyl)-isobutyl-amino]-5-hydroxy-pentylcarbamoyl}-2-naphthalen-1-yl-ethylamino)-ethyl Ester (MX-185)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in example 15 using 2-bromoethylacetate. The final product was obtained in 21% yield.

LC-MS: 613.3 (M+H)$^+$, 90% pure; $^1$H NMR (CD$_3$OD): δ 0.88 (m, 6H), 1.27 (m, 3H), 1.44 (m, 1H), 1.88 (m, 3H), 2.58 (m, 1H), 2.71 (m, 1H), 2.83 (dd, J=7.2, 14.5, 1H), 2.93 (dd, J=7.9, 14.5, 1H), 3.02 (m, 3H), 3.23 (m, 1H), 3.37 (m, 1H), 3.52 (m, 4H), 3.99 (t, J=5.3, 2H), 6.66 (d, J=8.8, 2H), 7.35 (d, J=6.9, 1H), 7.42 (d, J=8.2, 1H), 7.49 (m, 3H), 7.56 (t, J=7.1, 1H), 7.78 (d, J=8.2, 1H), 7.88 (d, J=8.1, 1H), 8.18 (d, J=8.4, 1H).

Example 22

Preparation of (2S,4S)-N-{4-[(4-Amino-benzenesulfonyl)-isobutyl-amino]-5-hydroxy-pentyl}-3-naphthalen-1-yl-2-propylamino-propionamide (MX-188)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure F using propionaldehyde. The final product was obtained in 54% yield.

LC-MS: 569.3 (M+H)$^+$, 90% pure; $^1$H NMR (DMSO-d$_6$): δ 0.72 (t, J=7.2, 3H), 0.80 (m, 6H), 1.23 (m, 7H), 1.51 (m, 2H), 1.83 (m, 1H), 2.22 (m, 1H), 2.36 (m, 1H), 2.73 (dd, J=7.4, 14.2, 1H), 2.83 (dd, J=7.4, 14.2, 1H), 3.00 (m, 2H), 3.11 (m, 1H), 3.16 (d, J=5.2, 1H), 3.21 (m, 1H), 3.48 (m, 1H), 4.58 (m, 1H), 5.91 (s, 2H), 6.58 (d, J=8.8, 2H), 7.34 (d, J=6.8, 1H), 7.44 (m, 3H), 7.54 (m, 2H), 7.78 (d, J=7.9, 2H), 7.90 (d, J=7.9, 1H), 8.12 (d, J=8.4, 1H).

Example 23

Preparation of (1S,4S)-Cyclopentanecarboxylic Acid (1-{4-[(4-Amino-benzenesulfonyl)-isobutyl-amino]-5-hydroxy-pentylcarbamoyl}-2-naphthalen-1-yl-ethyl)-amide (MX-197)

The title compound was prepared from (2S,4S)-2-amino-N-{4-[(4-amino-benzenesulfonyl)-isobutyl-amino]-5- hydroxy-pentyl}-3-naphthalen-1-yl-propionamide (product of example 8) as described in general procedure D using cyclopentanecarbonyl chloride. The final product was obtained in 52% yield.

LC-MS: 623.3 (M+H)$^+$, >98% pure; $^1$H NMR (CD$_3$OD): δ 0.88 (2d, J=6.4, 6H), 1.16–1.27 (m, 3H), 1.41 (m, 2H), 1.51 (m, 2H), 1.60 (m, 2H), 1.71 (m, 1H), 1.78 (m, 1H), 1.88 (m, 1H), 2.61 (m, 1H), 2.83 (dd, J=7.2, 14.2, 1H), 2.96 (m, 3H), 3.36 (m, 2H), 3.54 (m, 4H), 4.72 (t, J=7.2, 1H), 6.66 (d, J=8.8, 2H), 7.38 (m, 2H), 7.48 (m, 2H), 7.54 (m, 1H), 7.75 (d, J=7.9, 1H), 7.85 (d, J=7.9, 1H), 8.20 (d, J=8.4, 1H).

Example 24

Preparation of (2S,4S)-2-Amino-N-{4-[(4-amino-benzenesulfonyl)-isobutyl-amino]-5-hydroxy-pentyl}-3,3-diphenyl-propionamide (MX-198)

To 0.59 g of (1S,4S)-(1-{4-[(4-amino-benzenesulfonyl)-isobutyl-amino]-5-hydroxy-pentylcarbamoyl}-2,2-diphenyl-ethyl)-carbamic acid tert-butyl ester in 5 mL of dichloromethane under stirring were added 5 mL of trifluoroacetic acid. The reaction was followed by TLC and upon disappearance of the starting material the mixture was evaporated in vacuo. The residue was taken up in ethyl acetate and the organic layer washed with aqueous 1.0N sodium hydroxide, with brine, dried over magnesium sulfate and filtered. The filtrate was evaporated and then placed under mechanical vacuum overnight to provide 0.49 g (94%) of title compound as a light brown foam. The product was used without further purification to give a series of diphenyl-propionamide derived tests compounds.

LC-MS: 553.3 (M+H)$^+$, >95% pure; $^1$H NMR (DMSO-d$_6$): δ 0.79 and 0.81 (2d, J=6.7, 2×3H), 0.98–1.20 (m, 3H), 1.31–1.42 (m, 1H), 1.77–1.87 (m, 1H), 2.67–2.84 (m, 4H), 3.13–3.45 (m, 5H), 3.95 (d, J=9.1, 1H), 4.11 (d, J=9.1, 1H), 4.57 (t, J=4.9, 1H), 5.91 (s, 2H), 6.59 (d, J=8.7, 2H), 7.11 (t, J=7.2, 1H), 7.14–7.22 (m, 3H), 7.25–7.31 (m, 6H), 7.38 (d, J=8.7, 2H), 7.70 (t, J=5.5, 1H).

Example 25

Preparation of (2S,4S)-N-{4-[(4-Amino-benzenesulfonyl)-isobutyl-amino]-5-hydroxy-pentyl}-2-isobutylamino-3-naphthalen-1-yl-propionamide (MX-204)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure F using isobutyraldehyde. The final product was obtained in 41% yield.

LC-MS: 583.3 (M+H)$^+$, 97% pure; $^1$H NMR (CD$_3$OD): δ 0.81 (2d, J=7.5, 6H), 0.87 (2d, J=6.8, 6H), 1.23 (m, 4H), 1.37 (m, 1H), 1.65 (m, 1H), 1.88 (m, 1H), 2.27 (d, J=6.4, 2H), 2.82 (dd, J=7.3, 14.3, 1H), 2.91 (dd, J=7.6, 14.3, 1H), 2.98 (m, 2H), 3.45 (m, 4H), 3.50 (m, 1H), 6.66 (d, J=8.4, 2H), 7.35 (d, J=6.8, 1H), 7.42 (m, 1H), 7.49 (m, 3H), 7.55 (m, 1H), 7.78 (d, J=8.1, 1H), 7.88 (d, J=8.1, 1H), 8.17 (d, J=8.4, 1H).

Example 26

Preparation of (2S,4S)-N-{4-[(4-Amino-benzenesulfonyl)-isobutyl-amino]-5-hydroxy-pentyl}-2-ethylamino-3-naphthalen-1-yl-propionamide (MX-205)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) as described in general procedure F using acetaldehyde. The final product was obtained in 64% yield.

LC-MS: 555.2 (M+H)$^+$, >98% pure; $^1$H NMR (CD$_3$OD): δ 0.83 (m, 6H), 1.06 (m, 6H), 1.24 (m, 2H), 1.82 (m, 1H), 2.69 (m, 2H), 2.84 (m, 5H), 3.28 (m, 3H), 3.38 (m, 2H), 3.47 (m, 2H), 3.64 (m, 1H), 6.62 (d, J=8.6, 2H), 7.31 (d, J=14.1, 1H), 7.40 (m, 3H), 7.46 (m, 1H), 7.51 (m, 1H), 7.76 (d, J=7.9, 1H), 7.85 (d, J=7.9, 1H), 8.09 (d, J=8.4, 1H).

Example 27

Preparation of (1S,4S)-(1-{4-[(4-Amino-benzenesulfonyl)-isobutyl-amino]-5-hydroxy-pentylcarbamoyl}-2-naphthalen-1-yl-ethylamino)-acetic Acid (MX-206)

The title compound was prepared from (2S,4S)-2-amino-N-{4-[(4-amino-benzenesulfonyl)-isobutyl-amino]-5-hydroxy-pentyl}-3-naphthalen-1-yl-propionamide (product of example 8) using tert-butyl bromoacetate. The final product was hydrolysed using lithium hydroxide to obtain the acid in 74% yield.

LC-MS: 585.3 (M+H)$^+$, 90% pure.

Example 28

Preparation of (1S,5S)-(1-{5-[(4-Amino-benzenesulfonyl)-isobutyl-amino]-6-hydroxy-hexylcarbamoyl}-2-naphthalen-1-yl-ethyl)-carbamic Acid Methyl Ester (MX-36)

The preparation of the title compound is based on scheme 2 of this invention.

Step A. Preparation of (2S)-3-Isobutylamino-azepan-2-one (IX)

L-α-amino-ε-caprolactam (22.0 g) was dissolved in cold dichloroethane (DCM, 200 mL). isobutyraldehyde (12.6 g) was added slowly and stirred until the heat evolved was dissipated (water forms at the surface). The cold solution was added to 46.5 g of powdered NaBH(OAc)$_3$ in DCM (0.5 L). AcOH (70 mL) was added to the solution. The slightly turbid mixture was stirred at 20° C. for 4 h. A 500 mL solution of 2M NaOH was added slowly to the turbid mixture and the pH adjust to 11 using a concentrated NaOH solution, and then the mixture stirred for a further 20 min. After extraction, the DCM layer was dried with MgSO$_4$, filtered and evaporated. The oil thus obtained crystallizes slowly on standing (27.8 g, 85%) and was used without further purification in the next step.

$^1$H NMR (CDCl$_3$): δ 0.93 (d, J=6.5, 3H), 0.97 (d, J=6.5, 3H), 1.39 (t, J=9.8, 1H), 1.47 (m, 1H), 1.78–1.65 (m, 2H), 2.00–1.93 (m, 2H), 2.32–2.2 (m, 2H), 2.38 (t, J=9.7, 1H), 3.16 (m, 3H), 6.62 (s, 1H (NH)). mp 52–54° C. (hexanes).

A small sample was converted to the S-methyl benzyl urea by adding the solid to a solution of S-methyl benzyl isocyanate in MeCN. NMR gives 98% ee.

Step B. Preparation of Nα-Isobutyl-Nα-(4-acetamidobenzenesulfonyl)-L-α-amino-ε-caprolactam (X)

Nα-isobutyl-L-α-amino-ε-caprolactam (IX) (4.1 g free base) was dissolved in DCM (200 mL) and treated with 4.0 g triethylamine, followed by 4-acetamidobenzenesulfonyl chloride (5.2 g). A 0.1 g portion of dimethylaminopyridine was added and the mixture was stirred 5 h. The resulting thick slurry was poured into 500 mL 0.5 M HCl and shaken vigorously. The solid in the biphasic solution was filtered out and washed with cold acetone to give 7.3 g (87%) of clean product.

¹H NMR (DMSO-d₆): δ 0.93 (d, J=6.0, 3H), 0.96 (d, J=6.0, 3H), 1.39 (t, J=12.0, 1H), 1.85–1.65 (m, 3H), 2.08–2.18 (m and s, 6H), 2.90–2.97 (m, 1H), 3.00–3.06 (m, 2H), (dd, J=14.2, 8.5, 1H), 4.65 (d, J=8.7, 1H), 6.3 (s, 1H), 7.42 (d, J=8.8, 2H), 7.6 (d, J=8.8, 2H). mp 230–233° C. (EtOH).

Step C. Preparation of (3S)-3-[(4-Acetylamino-benzenesulfonyl)-isobutyl-amino]-2-oxo-azepane-1-carboxylic Acid tert-Butyl Ester (Boc Activation) (XI)

4.2 g of Nα-isobutyl-Nα-(4-acetamidobenzenesulfonyl)-L-α-amino-ε-caprolactam (X) was suspended in 30 mL MeCN and briefly sonicated to break up any large chunks. To this white suspension was added 6.7 g (3 eq.) of di-tert-butyl pyrocarbonate in 10 mL MeCN. The suspension was stirred with a magnetic bar and a 120 mg portion of DMAP was added. The solution becomes a clear light yellow after a few minutes. TLC (EtOAc) reveals 1 product Rf 0.9 (starting material Rf at 0.4). The solution is poured in distilled water 20 mL and extracted with ether, dried with Na₂SO₄ and evaporated yielding 6.90 g. A sample was recrystallized from hexanes.

¹H NMR (DMSO-d₆): δ 0.68 (d, J=6.0, 3H), 0.85 (d, J=6.0, 3H), 1.39 (s, 10H), 1.47 (s, 9H), 1.85–1.65 (m, 3H ), 2.15 (s, 3H), 2.80 (q, J=4, 1H), 3.10–3.36 (m, 2H), 4.01 (d, J=8.0, 1H), 4.85 (d, J=8.7, 1H), 7.32 (d, J=8.8, 2H), 7.87 (d, J=8.8, 2H). mp 123–124° C.

Step D. Preparation of (1S)-4-Amino-N-(5-amino-1-hydroxymethyl-pentyl)-N-isobutyl-benzenesulfonamide (XII) (Reductive Ring Opening and Deprotection)

A 3.0 g portion of (3S)-3-[(4-acetylamino-benzenesulfonyl)-isobutyl-amino]-2-oxo-azepane-1-carboxylic acid tert-butyl ester (XI, step C) is dissolved in 40 mL EtOH followed by 750 mg NaBH₄. Brief heating with a heat gun gives a clear solution. TLC reveals one streaky spot after 20 min (EtOAc). The solution is concentrated to a paste, poured in 40 mL 1N NaOH and extracted with ethyl acetate, the organic phase dried with NaSO₄ and evaporated to give 2.8 g of product.

The above product is dissolved in 5 mL EtOH and 5 mL 12 N HCl is added. Vigorous gas evolution is observed for a few minutes. After 2 h the solution is evaporated and rendered basic with concentrated KOH and extracted with EtOAc yielding 1.75 g off a white powder.

¹H NMR (DMSO-d₆): δ 0.82 (m, 6H), 0.97–1.12 (m, 2H), 1.15–1.30 (m, 3H), 1.57 (m, 1H), 1.84 (m, 1H), 2.40 (t, J=7.8, 2H), 2.75 (m, 1H), 2.85 (m, 1H), 3.21 (m, 1H), 3.44 (d, J=6.4, 2H), 5.92 (br s, 2H), 6.59 (d, J=8.0, 2H), 7.39 (d, J=8.0, 2H).

Step E. Preparation of (2S)-2-Methoxycarbonylamino-3-naphthalen-1-yl-propionic Acid To a solution of L-1-naphthylalanine (215 mg, 1 mmol) (Peptech Corp.) in 5 mL 1N NaOH and 0.5 mL saturated Na₂CO₃ (resulting solution at pH 10) was added methoxycarbonyloxysuccinimide (187 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na₂SO₄, filtered and evaporated to an oil which solidifies to yields 200 mg (73%) of the desired material. This intermediate (referred as the N-substituted amino acid) was used without further purification in the next step.

Step F. Preparation of (1S,5S)-(1-{5-[(4-Amino-benzenesulfonyl)-isobutyl-amino]-6-hydroxy-hexylcarbamoyl}-2-naphthalen-1-yl-ethyl)-carbamic Acid Methyl Ester To a suitable vessel was added 100 mg N-substituted amino acids, and a 1 mL aliquot of DMF, 150 mg EDAC, 75 mg HOBt were added. After 30 min at 40° C., 1.5 eq. of the amino alcohol, (1S)-4-amino-N-(5-amino-1-hydroxymethyl-pentyl)-N-isobutyl-benzenesulfonamide (product of step D) was added along with 100 mg N-methyl morpholine. The solution was then stirred at 23° C. for 4–12 h. A 1M K₂CO₃ (20 mL aliquot) is added and left for 1 h. Then EtOAc is added (50 mL). The aqueous phase is separated and extracted with citric acid (10%) 50 mL. The organic phase was separated and evaporated. The residue was purified by semi-preparative HPLC and lyophilized to yield 85 mg, 35% of the desired material.

LC-MS: 599.2 (M+H)⁺, >95% pure; ¹H NMR (CD₃OD): δ 0.83–0.87 (m, 3H), 0.88 (d, J=6.3, 6H), 1.08–1.11 (m, 2H), 1.29–1.34 (m, 2H), 1.41–1.52 (m, 1H), 1.82–1.92 (m, 1H), 2.74–3.09 (m, 4H), 3.33–3.49 (m, 6H), 3.52 (s, 3H), 4.40 (t, J=5.1, 1H), 6.70 (d, J=8.0, 2H), 7.30–7.38 (m, 2H), 7.41–7.55 (m, 4H), 7.73 (d, J=7.6, 1H), 7.83 (d, J=7.6, 1H), 8.19 (d, J=7.6, 1H).

Example 29

Preparation of (1S,5S)-(1-{5-[(4-Amino-benzenesulfonyl)-isobutyl-amino]-6-hydroxy-hexylcarbamoyl}-2-naphthalen-2-yl-ethyl)-carbamic Acid Methyl Ester (MX-70)

The title compound was prepared from (1S)-4-amino-N-(5-amino-1-hydroxymethyl-pentyl)-N-isobutyl-benzenesulfonamide (XII) (example 28, step D) as described in general procedure B using L-2-naphthylalanine. The L-2-naphthylalanine was initially transformed into its 2-methoxycarbonylamino-3-naphthalen-2-yl-propionic acid derivative following the procedure used for L-1-naphthylalanine (example 28, step E). The final product was obtained in 41% yield (165 mg).

LC-MS: 599.2 (M+H)⁺, >95% pure; ¹H NMR (CD₃OD): δ 0.83–0.87 (m, 1H), 0.88 (d, J=6.3, 6H), 1.11–1.15 (m, 2H), 1.16–1.24 (m, 1H), 1.41–1.50 (m, 1H) 1.82–1.92 (m, 1H), 2.74–2.96 (m, 3H), 3.02–3.09 (m, 2H), 3.23–3.28 (m, 1H), 3.39–3.42 (m, 1H), 3.47–3.50 (m, 2H), 3.57 (s, 3H), 4.35 (t, J=5.1, 1H), 6.65 (d, J=8.0 2H), 7.30–7.46 (m, 5H), 7.66 (s, 1H), 7.70–7.85 (m, 3H).

Example 30

Preparation of (1S,5R,S)-(1-{5-[(4-Amino-benzenesulfonyl)-isobutyl-amino]-6-hydroxy-hexylcarbamoyl}-2-biphenyl-2-yl-ethyl)-carbamic Acid Methyl Ester (MX-39)

This derivative was prepared as described for the synthesis of the S,S diastereoisomer (1S,5S)-(1-{5-[(4-amino-benzenesulfonyl)-isobutyl-amino]-6-hydroxy-hexylcarbamoyl}-2-biphenyl-2-yl-ethyl)-carbamic acid methyl ester (see example 39). The spectral characteristics of the final compound are the same as for the S,S diastereoisomer.

Example 31

Preparation of (1S,5S)-[1-{5-[(4-Amino-benzenesulfonyl)-isobutyl-amino]-6-hydroxy-hexylcarbamoyl}-2-(4'-methoxy-biphenyl-2-yl)-ethyl]-carbamic Acid Methyl Ester (MX-85)

The preparation of the title compound is based on schemes 2 and 3 of this invention.

Step A. Preparation of (2S)-3-(2-Bromo-phenyl)-2-methoxycarbonylamino-propionic Acid 1.0 g L-2-bromo-Phe (Peptech Corp.) is dissolved in 6 mL 1M $K_2CO_3$ followed by 0.77 g methoxycarbonyloxysuccinimide in 20 mL acetone. The resulting clear biphasic solution is stirred for 4 h, then concentrated to 10 mL. The resulting basic solution is extracted with ether and the aqueous phase rendered acidic with 6 M HCl. The oily precipitate is extracted with EtOAc (2×20 mL) and evaporated to yield 1.16 g of a clear oil which crystallizes upon standing.

$^1$H NMR (CD$_3$OD): δ 2.94–3.02 (m, 1H), 3.30–3.36 (m, 1H), 3.51 (s, 3H) 4.52 (t, J=7.6, 1H), 7.04 (t, J=6.8 1H), 7.20–7.26 (m, 2H), 7.52 (d, J=7.0, 2H).

Step B. Preparation of (2S)-3-(4'-Methoxy-biphenyl-2-yl)-2-methoxycarbonylamino-propionic Acid 250 mg of (2S)-3-(2-bromo-phenyl)-2-methoxycarbonylamino-propionic acid (step A) and 150 mg 4-methoxyphenyl boronic acid are dissolved in 5 mL warm 1 M $Na_2CO_3$ followed by 2 mL EtOH. The mixture is degassed for 15 min after which 300 mg of 10% Pd/C Degussa type E 101 is added. The solution is then heated to reflux for 4 h after which it is cooled and filtered through a thin pad of celite. The solids are washed with 1 M NaOH aliquots (2 mL) and the aqueous solution extracted once with 20 mL EtOAc. The aqueous phase is then acidified with 6N HCl and the resulting solution extracted with EtOAc (2×20 mL). The organic extracts are then combined and evaporated to yield 201 mg of product 73%.

$^1$H NMR (CD$_3$OD): δ 3.36–3.39 (m, 1H), 3.50 (br s, 4H), 3.80 (s, 3H) 4.16 (t, J=7.6, 1H), 6.94 (d, J=7.8 2H), 7.10 (t, J=3.6 1H), 7.14–7.21 (m, 5H), 7.27 (t, J=4.0 1H).

Step C. Preparation of (1S,5S)-[1-{5-[(4-Amino-benzenesulfonyl)-isobutyl-amino]-6-hydroxy-hexylcarbamoyl}-2-(4'-methoxy-biphenyl-2-yl)-ethyl]-carbamic Acid Methyl Ester This derivative was prepared from (1S)-4-amino-N-(5-amino-1-hydroxymethyl-pentyl)-N-isobutyl-benzenesulfonamide (XII) (example 28, step D) as described in general procedure B using 3-(4'-methoxy-biphenyl-2-yl)-2-methoxycarbonylamino-propionic acid (step B). The final product was obtained in 51% yield (83 mg).

LC-MS: 655.3 (M+H)$^+$, >95% pure; $^1$H NMR (CD$_3$OD) δ 0.87 (d, J=6.3, 6H), 0.98–1.15 (m, 2H), 1.19–1.38 (m, 3H), 1.51–1.54 (m, 1H) 1.88–1.97 (m, 1H), 2.74–3.14 (m, 6H), 3.36–3.39 (m, 1H), 3.50 (br s, 4H), 3.80 (s, 3H), 4.06 (t, J=7.6, 1H), 6.63 (d, J=8.8, 2H), 6.99 (d, J=7.8, 2H), 7.14 (t, J=3.6, 1H), 7.23 (d, J=6.8, 2H), 7.27 (t, J=4.0, 1H), 7.47 (d, J=7.8, 2H).

Example 32

Preparation of (1S,5S)-Morpholine-4-carboxylic Acid (1-{5-[(4-Amino-benzenesulfonyl)-isobutyl-amino]-6-hydroxy-hexylcarbamoyl}-2-naphthalen-1-yl-ethyl)-amide (MX-86)

Step A. Preparation of (2S)-2-[(Morpholine-4-carbonyl)-amino]-3-naphthalen-1-yl-propionic Acid To a solution of L-1-naphthylalanine (215 mg, 1 mmol) (Peptech Corp.) in 5 mL 1N NaOH and 0.5 mL saturated $Na_2CO_3$ (resulting solution at pH 10) was added morpholine-4-carbonyl chloride (150 mg, 1.0 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over $Na_2SO_4$, filtered and evaporated to an oil which solidifies to yields 125 mg (38%) of the desired material. This compound was used as such in the next step.

Step B. Preparation of (1S,5S)-Morpholine-4-carboxylic Acid (1-{5-[(4-Amino-benzenesulfonyl)-isobutyl-amino]-6-hydroxy-hexylcarbamoyl}-2-naphthalen-1-yl-ethyl)-amide This material was prepared from (1S)-4-amino-N-(5-amino-1-hydroxymethyl-pentyl)-N-isobutyl-benzenesulfonamide (XII) (example 28, step D) as described in general procedure B using 2-[(morpholine-4-carbonyl)-amino]-3-naphthalen-1-yl-propionic acid (step A). The final product was obtained in 32% yield (33 mg).

LC-MS: 654.3 (M+H)$^+$, >95% pure; $^1$H NMR (CD$_3$OD): δ 0.83–0.87 (m, 1H), 0.88 (d, J=6.3, 6H), 1.18–1.21 (m, 2H), 1.29–1.34 (m, 1H), 1.41–1.52 (m, 1H), 1.82–1.92 (m, 1H), 2.74–2.89 (m, 2H), 2.90–2.99 (m, 1H), 3.09–3.15 (m, 1H), 3.25–3.36 (m, 3H), 3.44–3.49 (m, 2H), 3.51–3.69 (m, 6H), 4.60 (t, J=4.9, 1H), 6.61 (d, J=8.0, 2H), 7.30–7.38 (m, 2H), 7.41 (d, J=8.0, 2H), 7.50–7.55 (m, 2H), 7.73 (d, J=7.6, 1H) 7.83 (d, J=7.6, 1H), 8.19 (d, J=7.6, 1H).

Example 33

Preparation of (1S,5S)-Morpholine-4-carboxylic Acid (1-{5-[(4-Amino-benzenesulfonyl)-isobutyl-amino]-6-hydroxy-hexylcarbamoyl}-2-naphthalen-2-yl-ethyl)-amide (MX-95)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure D using 4-morpholinecarbonyl chloride. The final product was obtained in 21% yield.

LC-MS: 654.3 (M+H)$^+$, >95% pure; $^1$H NMR (CD$_3$OD): δ 0.89 (d, J=6.4, 6H), 1.02–0.93 (m, 2H), 1.27–1.17 (m, 2H), 1.41–1.37 (m, 1H), 1.98 (quint, J=6.8, 1H), 2.80 (dd, J=6.9, 14.4, 2H), 2.97–2.90 (m, 2H), 3.12–3.06 (m, 2H), 3.33–3.23 (m, 5H), 3.39–3.36 (m, 1H), 3.54–3.45 (m, 6H), 4.54 (t, J=7.8, 1H), 6.67 (d, J=8.6, 2H), 7.47–7.39 (m, 5H), 7.69 (s, 1H), 7.83–7.77 (m, 3H).

Example 34

Preparation of (1S,5S)-(1-{5-[(4-Amino-benzenesulfonyl)-isobutyl-amino]-6-hydroxy-hexylcarbamoyl}-2,2-diphenyl-ethyl)-carbamic Acid Methyl Ester (MX-100)

Step A. Preparation (2S)-2-Methoxycarbonylamino-3,3-diphenyl-propionic Acid

To a solution of L-diphenylalanine (241 mg, 1.0 mmol) (Peptech Corp.) in 5 mL 1N NaOH and 0.5 mL saturated $Na_2CO_3$ (resulting solution at pH 10) was added methoxycarbonyloxysuccinimide (carbonic acid 2,5-dioxo-pyrrolidin-1-yl ester methyl ester) (180 mg, 1.1 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over $Na_2SO_4$, filtered and evaporated to an oil which solidifies to yields 250 mg (83%) of the desired material. This derivative was used as such in the next step.

Step B. Preparation of (1S,5S)-(1-{5-[(4-Amino-benzenesulfonyl)-isobutyl-amino]-6-hydroxy-hexylcarbamoyl}-2,2-diphenyl-ethyl)-carbamic Acid Methyl Ester The title compound was prepared from (1S)-4-amino-N-(5-amino-1-hydroxymethyl-pentyl)-N-isobutyl-benzenesulfonamide (XII) (example 28, step D) as described in general procedure B using (2S)-2-methoxycarbonylamino-3,3-diphenyl-propionic acid (step A). The final product was obtained in 67% yield (121 mg).

LC-MS: 625.3 (M+H)$^+$, >95% pure; $^1$H NMR (CD$_3$OD): δ 0.71–0.85 (m, 2H), 0.88 (d, J=6.3, 5H), 0.91–0.96 (m, 2H), 1.29–1.34 (m, 1H), 1.41–1.52 (m, 1H) 1.82–1.92 (m, 1H), 2.61–2.68 (m, 1H), 2.81–2.85 (m, 2H), 2.94–3.05 (m, 2H), 3.38–3.40 (t, J=5.0, 1H), 3.50–3.51 (m, 1H), 3.52 (s, 3H), 4.28 (d, J=11.0, 1H), 4.87 (d, J=11.0, 1H), 6.69 (d, J=8.0, 2H), 7.15–718 (m, 2H), 7.20–7.31 (m, 6H), 7.33 (d, J=7.9, 2H), 7.47 (d, J=7.5, 1H). $^{13}$C NMR (CD$_3$OD): δ 20.0, 20.1, 23.3, 25.4, 28.1, 28.5, 28.9, 38.1, 40.0, 51.2, 51.6, 53.1, 57.2, 57.4, 59.5, 61.9, 62.4, 112.6, 125.7, 126.2, 126.3, 127.9, 128.1, 128.15, 128.2, 128.4, 128.7, 141.3, 141.9, 152.4, 155.9, 169.9, 172.5.

Example 35

Preparation of (1S,5S)-Morpholine-4-carboxylic Acid (1-{6-Hydroxy-5-[isobutyl-(4-methoxy-benzenesulfonyl)-amino]-hexylcarbamoyl}-2-naphthalen-2-yl-ethyl)-amide (MX-108)

Step A. Preparation of Nα-Isobutyl-Nα-(4-methoxybenzenesulfonyl)-L-α-amino-ε-caprolactam (2S)-3-Isobutylamino-azepan-2-one (example 28, step A) (4.1 g free base) was dissolved in DCM (200 mL) and treated with 4.0 g triethylamine followed by 4-methoxybenzenesulfonyl chloride (5.1 g). A 0.1 g portion of DMAP was added and the mixture was stirred 5 h. The resulting solution was poured into 500 mL 0.5 M HCl and shaken vigorously. The organic phase was separated and dried with MgSO$_4$, then evaporated to give 6.6 g (75%) of clean product.

$^1$H NMR (DMSO-d$_6$): δ 0.93 (d, J=6.0, 3H), 0.96 (d, J=6.0, 3H), 1.39 (t, J=12.0, 1H), 1.85–1.65 (m, 3H), 2.08–2.18 (m and s, 6H), 2.90–2.97 (m, 1H), 3.00–3.06 (m, 2H), 3.35 (dd, J=14.2, 8.5, 1H), 3.90 (s, 3H), 4.65 (d, J=8.7, 1H), 6.3 (s, 1H), 7.11 (d, J=9.0, 2H), 7.86 (d, J=8.8, 2H).

Step B. Preparation of (1S)-N-(5-Amino-1-hydroxymethyl-pentyl)-N-isobutyl-4-methoxy-benzenesulfonamide This compound was prepared from Nα-isobutyl-Nα-(4-methoxybenzenesulfonyl)-L-α-amino-ε-caprolactam (step A) in a three step reaction sequence (Boc activation, reductive ring opening and deprotection) as described for the preparation of (1S)4-amino-N-(5-amino-1-hydroxymethyl-pentyl)-N-isobutyl-benzenesulfonamide (example 28, steps C and D). The final product was obtained in 70% yield. This material was used as such in the next step.

Step C. Preparation of (1S,5S)-Morpholine-4-carboxylic Acid (1-{6-Hydroxy-5-[isobutyl-(4-methoxy-benzenesulfonyl)-amino]-hexylcarbamoyl}-2-naphthalen-2-yl-ethyl)-amide This derivative was prepared from (1S)-N-(5-amino-1-hydroxymethyl-pentyl)-N-isobutyl-4-methoxy-benzenesulfonamide (XII) (this example, step B) as described in general procedure B using (2S)-2-[(morpholine4-carbonyl)-amino]-3-naphthalen-2-yl-propionic acid. The (2S)-2-[(morpholine-4-carbonyl)-amino]-3-naphthalen-2-yl-propionic acid derivative was prepared from L-2-naphthylalanine as described for the preparation of (2S)-2-[(morpholine-4-carbonyl)-amino]-3-naphthalen-1-yl-propionic acid (example 32, step A). The final product was obtained in 46% yield (47 mg).

LC-MS: 669.3 (M+H)$^+$, >95% pure; $^1$H NMR (CD$_3$OD): δ 0.87 (d, J=6.3 6H), 1.08–1.11 (m, 2H), 1.29–1.38 (m, 3H), 1.51–1.54 (m, 1H) 1.88–1.97 (m, 1H), 2.84–3.20 (m, 6H), 3.23–3.26 (m, 1H), 3.31–3.35 (m, 4H), 3.50–3.57 (m, 5H), 3.56–3.60 (m, 1H), 3.85 (s, 3H), 4.52 (t, J=7.6, 1H), 7.04 (d, J=8.8, 2H), 7.33–7.43 (m, 2H), 7.66 (s, 1H), 7.71–7.85 (m, 6H).

Example 36

Preparation of (1S,5S)-[1-{6-Hydroxy-5-[isobutyl-(4-methoxy-benzenesulfonyl)-amino]-hexylcarbamoyl}-2-(4'-methoxy-biphenyl-2-yl)-ethyl]-carbamic Acid Methyl Ester (MX-109)

This derivative was prepared from (1S)-N-(5-amino-1-hydroxymethyl-pentyl)-N-isobutyl-4-methoxy-benzenesulfonamide (XII) (example 35, step B) as described in general procedure B using 3-(4'-methoxy-biphenyl-2-yl)-2-methoxycarbonylamino-propionic acid (example 31, step B). The final product was obtained in 32% yield (18 mg).

LC-MS: 670.3 (M+H)$^+$, >95% pure.

Example 37

Preparation of (1S,3R,S,5S)-Tetrahydro-furan-3-carboxylic Acid (1-{5-[(4-Amino-benzenesulfonyl)-isobutyl-amino]-6-hydroxy-hexylcarbamoyl}-2-naphthalen-2-yl-ethyl)-amide (MX-110)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure E using (3R,S)-3-tetrafuranoic acid. The final product was obtained in 6% yield.

LC-MS: 639.3 (M+H)$^+$, >90% pure; $^1$H NMR (CD$_3$OD): δ 0.89 (d, J=6.6, 6H), 0.99–0.93 (m, 2H), 1.25–1.16 (m, 2H), 1.45–1.37 (m, 2H), 1.62–1.59 (m, 1H), 1.93–1.85 (m, 2H), 3.11–2.78 (m, 6H), 3.28–3.23 (m, 1H), 3.46–3.37 (m, 1H), 3.51–3.49 (m, 2H), 3.78–3.63 (m, 3H), 3.89–3.83 (m, 1H), 4.68–4.65 (m, 1H), 6.67 (d, J=8.6, 2H), 7.48–7.37 (m, 5H), 7.68 (d, J=6.2, 1H), 7.82–7.78 (m, 3H).

Example 38

Preparation of (1S,5S)-Morpholine-4-carboxylic Acid [1-{5-[(4-Amino-benzenesulfonyl)-isobutyl-amino]-6-hydroxy-hexylcarbamoyl}-2-(4'-methoxy-biphenyl-2-yl)-ethyl]-amide (MX-117)

The preparation of the title compound is based on schemes 2 and 3 of this invention.

Step A. Preparation (2S)-3-(2-Bromo-phenyl)-2-[(morpholine-4-carbonyl)-amino]-propionic Acid 1.0 g L-2-bromo-Phe (Peptech Corp.) is dissolved in 6 mL 1M K$_2$CO$_3$ followed by 0.7 g morpholine-4-carbonyl chloride (4.7 mmol) dissolved in 20 mL acetone. The resulting clear biphasic solution is stirred for 4 h, then concentrated to 10 mL. The resulting basic solution is extracted with ether and the aqueous phase rendered acidic with 6 M HCl. The oily precipitate is extracted with EtOAc (2×20 mL) and evaporated to yield 1.2 g (76%) of a clear oil which crystallizes upon standing. This material was used as such in the next step.

Step B. Preparation of (2S)-3-(4'-Methoxy-biphenyl-2-yl)-2-[(morpholine4-carbonyl)-amino]-propionic Acid 250 mg of (2S)-3-(2-bromo-phenyl)-2-[(morpholine-4-carbonyl)-amino]-propionic acid (step A) and 150 mg 4-methoxyphenyl boronic acid are dissolved in 5 mL warm 1 M Na$_2$CO$_3$ followed by 2 mL EtOH. The mixture is degassed for 15 min after which 300 mg of 10% Pd/C Degussa type E 101 is added. The solution is then heated to reflux for 4 h after which it is cooled and filtered through a thin pad of celite. The solids are washed with 1 M NaOH aliquots (2 mL) and the aqueous solution extracted once with 20 mL EtOAc. The aqueous phase is then acidified with 6N HCl and the resulting solution extracted with EtOAc (2×20 mL). The organic extracts are then combined and evaporated to yield 201 mg (73%) of product. This material was used as such in the next step.

Step C. Preparation of (1S,5S)-Morpholine-4-carboxylic Acid [1-{5-[(4-Amino-benzenesulfonyl)-isobutyl-amino]-6-hydroxy-hexylcarbamoyl}-2-(4'-methoxy-biphenyl-2-yl)-ethyl]-amide This derivative was prepared from (1S)-N-(5-amino-1-hydroxymethyl-pentyl)-N-isobutyl-4-methoxy-benzenesulfonamide (XII) (example 35, step B) as described in general procedure B (2S)-3-(4'-methoxy-biphenyl-2-yl)-2-[(morpholine-4-carbonyl)-amino]-propionic acid (step B). The final product was obtained in 33% yield (100 mg).

LC-MS: 710.3 (M+H)+, >95% pure.

Example 39

Preparation of (1S,5S)-(1-{5-[(4-Amino-benzenesulfonyl)-isobutyl-amino]-6-hydroxy-hexylcarbamoyl}-2-biphenyl-2-yl-ethyl)-carbamic Acid Methyl Ester (MX-118)

The preparation of the title compound is based on schemes 2 and 3 of this invention.

Step A. Preparation of (2S)-3-Biphenyl-2-yl-2-methoxycarbonylamino-propionic Acid 91 mg of (2S)-3-(2-bromo-phenyl)-2-methoxycarbonylamino-propionic acid (product of example 31, step A) and 30 mg phenyl boronic acid are dissolved in 3 mL warm 1 M $Na_2CO_3$ followed by 2 mL EtOH. The mixture is degassed for 15 min after which 150 mg of 10% Pd/C Degussa type E 101 is added. The solution is then heated to reflux for 4 h after which it is cooled and filtered through a thin pad of celite. The solids are washed with 1 M NaOH aliquots (2 mL) and the aqueous solution extracted once with 10 mL EtOAc. The aqueous phase is then acidified with 6N HCl and the resulting solution extracted with EtOAc (2×10 mL). The organic extracts are then combined and evaporated to yield 86 mg (89%) of product. This material was used as such in the next step.

Step B. Preparation of (1S,5S)-(1-{5-[(4-Amino-benzenesulfonyl)-isobutyl-amino]-6-hydroxy-hexylcarbamoyl}-2-biphenyl-2-yl-ethyl)-carbamic Acid Methyl Ester This derivative was prepared from (1S)-4-amino-N-(5-amino-1-hydroxymethyl-pentyl)-N-isobutyl-benzenesulfonamide (XII) (example 28, step D) as described in general procedure B using (2S)-3-biphenyl-2-yl-2-methoxycarbonylamino-propionic acid (step A). The final product was obtained in 41% yield (27 mg).

LC-MS: 625.3 (M+H)+, >95% pure.

Example 40

Preparation of (1S,5S)-Morpholine-4-carboxylic Acid (1-{5-[(4-Amino-benzenesulfonyl)-isobutyl-amino]-6-hydroxy-hexylcarbamoyl}-2,2-diphenyl-ethyl)-amide (MX-119)

The title compound was prepared from (1S)-4-amino-N-(5-amino-1-hydroxymethyl-pentyl)-N-isobutyl-benzenesulfonamide (XII) (example 28, step D) as described in general procedure B using (2S)-2-[(morpholine-4-carbonyl)-amino]-3,3-diphenyl-propionic acid. The (2S)-2-[(morpholine-4-carbonyl)-amino]-3,3-diphenyl-propionic acid derivative was prepared from L-diphenylalanine as described for the preparation of (2S)-2-[(morpholine-4-carbonyl)-amino]-3-naphthalen-1-yl-propionic acid (example 32, step A). The final product was obtained in 28% yield (14 mg).

LC-MS: 680.3 (M+H)+, >95% pure.

Example 41

Preparation of (2S,5S)-N-{5-[(4-Amino-benzenesulfonyl)-isobutyl-amino]-6-hydroxy-hexyl}-2-(3,3-dimethyl-ureido)-3-naphthalen-2-yl-propionamide (MX-125)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure D using dimethylcarbamyl chloride. The final product was obtained in 11% yield.

LC-MS: 612.3 (M+H)+, >95% pure; $^1$H NMR ($CD_3OD$): δ 0.89 (d, J=6.7, 6H), 1.00–0.93 (m, 1H), 1.26–1.15 (m, 3H), 1.14–1.37 (m, 1H), 1.88 (quint, J=6.8, 1H), 2.83–2.78 (m, 7H), 2.97–2.88 (m, 2H), 3.14–3.06 (m, 2H), 3.26–3.22 (m, 1H), 3.40–3.35 (m, 1H), 3.52–3.49 (m, 2H), 4.51 (t, J=7.5, 1H), 6.67 (d, J=8.5, 2H), 7.47–7.39 (m, 5H), 7.70 (s, 1H), 7.83–7.77 (m, 3H).

Example 42

Preparation of (1S,5S)-Cyclohexanecarboxylic Acid (1-{5-[(4-Amino-benzenesulfonyl)-isobutyl-amino]-6-hydroxy-hexylcarbamoyl}-2-naphthalen-2-yl-ethyl)-amide (MX-126)

The title compound was prepared from (2S,S)-2-amino-N-{5-[(4-amino-benzenesulfonyl)-isobutyl-amino]-6-hydroxy-hexyl}-3-naphthalen-2-yl-propionamide (product of example 49) as described in general procedure D using cyclohexanecarbonyl chloride. The final product was obtained in 56% yield.

LC-MS: 651.3 (M+H)+, >95% pure; $^1$H NMR ($CD_3OD$): δ 0.89 (d, J=6.4, 6H), 1.01–0.96 (m, 1H), 1.25–1.16 (m, 7H), 1.38–1.30 (m, 2H), 1.55–1.45 (m, 1H), 1.63–1.61 (m, 2H), 1.72 (d, J=10.4, 2H), 1.89–1.87 (m, 1H), 2.18–2.15 (m, 1H), 2.89–2.78 (m, 1H), 2.97–2.90 (m, 2H), 3.10–3.04 (m, 2H), 3.26–3.21 (m, 1H), 3.45–3.37 (m, 1H), 3.52–3.49 (m, 2H), 4.64 (t, J=7.6, 1H), 6.67 (d, J=8.6, 2H), 7.38 (d, J=8.3, 1H), 7.47–7.42 (m, 4H), 7.68 (s, 1H), 7.82–7.77 (m, 3H).

Example 43

Preparation of (1S,5S)-Morpholine-4-carboxylic Acid (1-{5-[(4-Amino-benzenesulfonyl)-isobutyl-amino]-6-hydroxy-hexylcarbamoyl}-2-biphenyl-2-yl-ethyl)-amide (MX-128)

Step A. Preparation of (2S)-3-Biphenyl-2-yl-2-[(morpholine-4-carbonyl)-amino]-propionic Acid 300 mg of (2S)-3-(2-bromo-phenyl)-2-[(morpholine-4-carbonyl)-amino]-propionic acid (product of example 38, step A) and 100 mg phenyl boronic acid are dissolved in 5 mL warm 1 M $Na_2CO_3$ followed by 2 mL EtOH. The mixture is degassed for 15 min after which 300 mg of 10% Pd/C Degussa type E 101 is added. The solution is then heated to reflux for 4 h after which it is cooled and filtered through a thin pad of celite. The solids are washed with 1 M NaOH aliquots (2 mL) and the aqueous solution extracted once with 20 mL EtOAc. The aqueous phase is then acidified with 6N HCl and the resulting solution extracted with EtOAc (2×20 mL). The organic extracts are then combined and evaporated to yield 271 mg (89%) of product. This material was used as such in the next step.

Step B. Preparation of (1S,5S)-Morpholine-4-carboxylic Acid (1-{5-[(4-Amino-benzenesulfonyl)-isobutyl-amino]-6-hydroxy-hexylcarbamoyl}-2-biphenyl-2-yl-ethyl)-amide This derivative was prepared from (1S)-4-amino-N-(5-amino-1-hydroxymethyl-pentyl)-N-isobutyl-benzenesulfonamide (XII) (example 28, step D) as described in general procedure B using (2S)-3-biphenyl-2-yl-2-[(morpholine-4-carbonyl)-amino]-propionic acid (step A). The final product was obtained in 54% yield (61 mg).

LC-MS 680.1 (M+H)+, >95% pure.

Example 44

Preparation of (1S,5S)-Morpholine-4-carboxylic Acid (1-{5-[(4-Amino-3-chloro-benzenesulfonyl)-isobutyl-amino]-6-hydroxy-hexylcarbamoyl}-2-naphthalen-1-yl-ethyl)-amide (MX-132)

Step A. Preparation of Nα-Isobutyl-Nα-(4-acetamido-3-chlorobenzenesulfonyl)-L-α-amino-ε-caprolactam (2S)-3-Isobutylamino-azepan-2-one (example 28, step A) 300 mg was dissolved in DCM (20.0 mL) and treated with 1 ml triethylamine followed by 4-acetamido-3-chlorobenzenesulfonyl chloride (300 mg). A 0.01 g portion of DMAP was added and the mixture was stirred 5 h. The resulting thick slush was poured into 40 mL 0.5 M HCl and shaken vigorously. The solid in the biphasic solution was filtered out and washed with cold acetone to give (310 mg) of clean product.

$^1$H NMR (DMSO-d$_6$): δ 0.93 (d, J=6.0, 3H), 0.96 (d, J=6.0, 3H), 1.30 (t, J=12.0, 1H), 1.85–1.65 (m, 3H), 2.08–2.18 (m and s, 6H), 2.20 (s, 3H), 2.97–3.11 (m, 3H), 3.35 (dd, J=14.2, 8.5, 1H), 4.55 (d, J=8.7, 1H), 7.42 (d, J=8.8, 1H), 7.61 (d, J=8.8, 1 H), 7.70 (s 1H), 8.05 (d, J=8.7 1H), 9.54 (s, 1H).

Step B. Preparation of (1S)-4-Amino-N-(5-amino-1-hydroxymethyl-pentyl)-3-chloro-N-isobutyl-benzenesulfonamide This compound was prepared from Nα-isobutyl-Nα-(4-acetamido-3-chlorobenzenesulfonyl)-L-α-amino-ε-caprolactam (step A) in a three step reaction sequence (Boc activation, reductive ring opening and deprotection) as described for the preparation of (1S)4-amino-N-(5-amino-1-hydroxymethyl-pentyl)-N-isobutyl-benzenesulfonamide (example 28, steps C and D). The final product was obtained in 40% yield (147 mg). It was used as such in the next step.

Step C. Preparation of (1S,5S)-Morpholine-4-carboxylic Acid (1-{5-[(4-Amino-3-chloro-benzenesulfonyl)-isobutyl-amino]-6-hydroxy-hexylcarbamoyl}-2-naphthalen-1-yl-ethyl)-amide This derivative was prepared from (1S)-4-amino-N-(5-amino-1-hydroxymethyl-pentyl)-3-chloro-N-isobutyl-benzenesulfonamide (XII) (this example, step B) as described in general procedure B using (2S)-2-[(morpholine-4-carbonyl)-amino]-3-naphthalen-1-yl-propionic acid (see example 32, step A). The final product was obtained in 41% yield (27 mg).

LC-MS: 688.3 (M+H)+, >95% pure.

Example 45

Preparation of (1S,5S)-Morpholine-4-carboxylic Acid (1-{6-Hydroxy-5-[isobutyl-(4-methoxy-benzenesulfonyl)-amino]-hexylcarbamoyl}-2-naphthalen-1-yl-ethyl)-amide (MX-133)

The title compound was prepared from (1S)-N-(5-amino-1-hydroxymethyl-pentyl)-N-isobutyl-4-methoxy-benzenesulfonamide (XII) (example 35, step B) as described in general procedure B using (2S)-2-[(morpholine-4-carbonyl)-amino]-3-naphthalen-1-yl-propionic acid (see example 32, step A). The final product was obtained in 23% yield (27 mg).

LC-MS: 688.3 (M+H)+, >95% pure.

Example 46

Preparation of (1S,5S)-N-(1-{5-[(4-Amino-benzenesulfonyl)-isobutyl-amino]-6-hydroxy-hexylcarbamoyl}-2-naphthalen-2-yl-ethyl)-2,2-dimethyl-propionamide (MX-134)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure D using tert-butylacetyl chloride. The final product was obtained in 58% yield.

LC-MS: 625.3 (M+H)+, >90% pure; $^1$H NMR (CD$_3$OD): δ 0.89 (s, J=6.7, 6H), 1.07 (m, 9H), 1.29–1.17 (m, 6H), 1.42–1.33 (m, 1H), 1.92–1.88 (m, 1H), 2.90–2.79 (m, 1H), 2.97–2.91 (m, 1H), 3.17–3.11 (m, 2H), 3.26–3.23 (m, 2H), 3.40–3.38 (m, 1H), 5.51–3.45 (m, 2H), 4.68–4.65 (m, 1H), 6.67 (d, J=8.6 2H), 7.38 (d, J=8.6, 1H), 7.47–7.43 (m, 4H), 7.68 (s, 1H), 7.83–7.77 (m, 3H).

Example 47

Preparation of (1S,5S)-Cyclopropanecarboxylic Acid (1-{5-[(4-Amino-benzenesulfonyl)-isobutyl-amino]-6-hydroxy-hexylcarbamoyl}-2-naphthalen-2-yl-ethyl)-amide (MX-135)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure D using cyclopropanecarbonyl chloride. The final product was obtained in 79% yield.

LC-MS: 609.3 (M+H)+, >90% pure; $^1$H NMR (CD$_3$OD): δ 0.71–0.68 (m, 1H), 0.81–0.79 (m, 2H), 0.91–0.88 (m, 6H), 1.32–1.10 (m, 5H), 1.64–1.62 (m, 1H), 1.87–1.77 (m, 1H), 2.85–2.76 (m, 2H), 3.12–2.91 (m, 3H), 3.24–3.20 (m, 2H), 3.45–3.36 (m, 1H), 3.51–3.48 (m, 2H), 4.64–4.62 (m, 1H), 6.66 (d, J=8.4, 2H), 7.52–7.38 (m, 5H), 7.69 (s, 1H), 7.83–7.79 (m, 3H).

Example 48

Preparation of (2S,5S)-2-Acetylamino-N-{5-[(4-amino-benzenesulfonyl)-isobutyl-amino]-6-hydroxy-hexyl}-3-naphthalen-2-yl-propionamide (MX-136)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure D using acetyl chloride. The final product was obtained in 38% yield.

LC-MS: 583.3 (M+H)+, >95% pure; $^1$H NMR (CD$_3$OD): δ 0.98–0.82 (m, 8H), 1.21–1.09 (m, 3H), 1.44–1.34 (m, 1H), 1.91–1.84 (m, 4H), 2.87–2.77 (m, 2H), 2.96–2.92 (m, 2H), 3.08–3.05 (m, 2H), 3.24–3.19 (m, 1H), 3.40–3.35 (m, 1H), 3.47–3.44 (m, 2H), 3.51–3.48 (m, 2H), 4.65–4.61 (m, 1H), 6.66 (d, J=8.5, 2H), 7.39 (d, J=8.5, 1H), 7.48–7.44 (m, 4H), 7.69 (s, 1H), 7.83–7.79 (m, 3H).

Example 49

Preparation of (2S,5S)-2-Amino-N-{5-[(4-amino-benzenesulfonyl)-isobutyl-amino]-6-hydroxy-hexyl}-3-naphthalen-2-yl-propionamide (MX-137)

The preparation of the title is based on scheme 4 of this invention.

(1S,5S)-(1-{5-[(4-amino-benzenesulfonyl)-isobutyl-amino]-6-hydroxy-hexylcarbamoyl}-2-naphthalen-2-yl-ethyl)-carbamic acid tert-butyl ester (698 mg, 1.089 mmol) was added to 6 mL of ethanol and 6 mL of HCl. The mixture was stirred at room temperature until completion by TLC. The ethanol was evaporated and the acidic mixture was poured into an extracting funnel containing 75 mL of ethyl acetate and 50 mL of HCl 1M and separated. The aqueous layer was washed with ethyl acetate. The aqueous phase was basified with pellets of NaOH and poured into an extracting funnel. The organic layer was washed with NaOH 1M and brine, dried over sodium sulfate, filtered, evaporated and dried under vacuum to give 544 mg (92%) of a yellow solid (Rf=0, 100% EtOAc, indicator: ninhydrin).

LC-MS: 541.3 (M+H)$^+$, >95% pure.

Example 50

Preparation of (1S,5S)-(1-{5-[(4-Amino-3-chloro-benzenesulfonyl)-isobutyl-amino]-6-hydroxy-hexylcarbamoyl}-2,2-diphenyl-ethyl)-carbamic Acid Methyl Ester (MX-158)

The title compound was prepared from (1S)4-amino-N-(5-amino-1-hydroxymethyl-pentyl)-3-chloro-N-isobutyl-benzenesulfonamide (XII) (example 44, step B) as described in general procedure B using (2S)-2-methoxycarbonylamino-3,3-diphenyl-propionic acid (see example 34, step A). The final product was obtained in 43% yield (48 mg).

LC-MS: 659.2 (M+H)$^+$, >95% pure; $^1$H NMR (CD$_3$OD): δ 0.71–0.85 (m, 2H), 0.98 (d, J=6.3, 6H), 1.29–1.34 (m, 1H), 1.41–1.52 (m, 1H) 1.86–1.98 (m, 1H), 2.61–2.68 (m, 1H), 2.81–2.85 (m, 2H), 2.94–3.05 (m, 2H), 3.38–3.40 (t, J=5 1H), 3.50–3.56 (m and s, 4H), 4.25 (d, J=11.0, 1H), 4.88 (d, J=11.0, 1H) 6.80 (d, J=7.0, 2H), 7.15–718 (m, 2H), 7.20–7.31 (m, 6H), 7.33 (d, J=7.9, 2H), 7.37 (d, J=7.0, 1H), 7.60 (s, 1H).

Example 51

Preparation of (1S,5S)-Morpholine-4-carboxylic Acid (1-{5-[(4-Amino-3-chloro-benzenesulfonyl)-isobutyl-amino]-6-hydroxy-hexylcarbamoyl}-2-naphthalen-2-yl-ethyl)-amide (MX-161)

This derivative was prepared from (1S)-4-amino-N-(5-amino-1-hydroxymethyl-pentyl)-3-chloro-N-isobutyl-benzenesulfonamide (XII) (example 44, step B) as described in general procedure B using (2S)-2-[(morpholine-4-carbonyl)-amino]-3-naphthalen-2-yl-propionic acid. The latter derivative was prepared from L-2-naphthylalanine as described for the preparation of (2S)-2-[(morpholine-4-carbonyl)-amino]-3-naphthalen-1-yl-propionic acid from L-1-naphthylalanine. The final product was obtained in 25% yield (51 mg).

LC-MS: 688.3 (M+H)$^+$, >95% pure.

Example 52

Preparation of (1S,5S)-[1-{5-[(4-Amino-benzenesulfonyl)-isobutyl-amino]-6-hydroxy-hexylcarbamoyl}-2-(3'-fluoro-biphenyl-2-yl)-ethyl]-carbamic Acid Methyl Ester (MX-162)

This material was prepared from (1S)-4-amino-N-(5-amino-1-hydroxymethyl-pentyl)-N-isobutyl-benzenesulfonamide (XII) (example 28, step D) as described in general procedure B using (2S)-3-(3'-fluoro-biphenyl-2-yl)-2-methoxycarbonylamino-propionic acid (see example 56, step A). The final product was obtained in 33% yield (41 mg).

LC-MS: 643.3 (M+H)$^+$, >95% pure.

Example 53

Preparation of (1S,5S)-Morpholine-4-carboxylic Acid (1-{5-[(3-Amino-4-fluoro-benzenesulfonyl)-isobutyl-amino]-6-hydroxy-hexylcarbamoyl}-2-naphthalen-1-yl-ethyl)-amide (MX-170)

Step A. Preparation of 3-Amino-4-fluorobenzenesulfonyl Chloride 6.7 g of 2-fluoro-acetanilide is added to a solution of 30 mL of chlorosulfonic acid portion wise in a 3 neck flask equipped with a reflux condenser and a gas trap. The solution is slowly heated to 80° C. and stirred for 5 h. The solution is cooled and left a RT overnight. The solution is then poured cautiously into a large beaker containing 150 g of crushed ice and 200 mL of CHCl$_3$. The organic phase is the separated, dried with Na$_2$SO$_4$ and evacuated. The crude product is used as is. Note: This preparation leads sometimes to a mixture of regioisomers the 3-amino-4-fluorobenzenesulfonyl chloride as well as the 4-amino-3-fluorobenzenesulfonyl chloride. However, only the desired regioisomer was isolated in this particular example.

$^1$H NMR (CHCl$_3$): 7.15 (t, J=10.2, 1H), 7.37 (dd, J=7.1, 3.0, 1H), 7.42 (d, J=7.1, 1H).

Step B. Preparation of Nα-Isobutyl-Nα-(3-amino-4-fluorobenzenesulfonyl)-L-α-amino-ε-caprolactam Nα-isobutyl-L-α-amino-ε-caprolactam 300 mg was dissolved in DCM (20.0 mL) and treated with 1 ml triethylamine followed by 3-amino-4-fluorobenzenesulfonyl chloride (300 mg). A 0.01 g portion of DMAP was added and the mixture was stirred 5 h. The resulting thick slush was poured into mL 0.5 M HCl and shaken vigorously. The solid in the biphasic solution was filtered out and washed with cold acetone to give (298 mg) of clean product.

$^1$H NMR (DMSO-d$_6$): δ 0.93 (d, J=6.0, 3H), 0.96 (d, J=6.0, 3H), 1.40 (t, J=12.0, 1H), 1.85–1.65 (m, 3H), 2.08–2.18 (m and s, 6H), 2.23 (s, 3H), 2.97–3.11 (m, 3H), 3.35 (,dd, J=14.2, 8.5, 1H), 4.55 (d, J=8.7, 1H), 6.84 (ddd, J=8.1, 4.1, 2.0, 1H), 7.06 (dd, J=11.2, 8.1, 1H), 7.15 (dd, J=8.1, 2.0, 1H). $^{13}$C NMR (DMSO-d$_6$): δ 173.2, 152.2 (J=245.2), 136.9, 136.2, 114.8 (J=20), 113.2 (J=6.5), 112.9 (J=6.5), 60.0, 53.8, 40.7, 30.2, 28.8, 28.1, 27.7, 20.2.

Step C. Preparation of (1S)-3-Amino-N-(5-amino-1-hydroxymethyl-pentyl)-4-fluoro-N-isobutyl-benzenesulfonamide This derivative was prepared from Nα-isobutyl-Nα-(3-amino-4-fluorobenzenesulfonyl)-L-α-amino-ε-caprolactam (step B) in a three step reaction sequence (Boc activation, reductive ring opening and deprotection) as described for the preparation of (1S)-4-amino-N-(5-amino-1-hydroxymethyl-pentyl)-N-isobutyl-benzenesulfonamide (example 28, steps C and D). The final product was obtained in 68% yield and was used as such in the next step.

Step D. Preparation of (1S,5S)-Morpholine-4-carboxylic Acid (1-{5-[(3-Amino-4-fluoro-benzenesulfonyl)-isobutyl-amino]-6-hydroxy-hexylcarbamoyl}-2-naphthalen-1-yl-ethyl)-amide The title compound was prepared from (1S)-3-amino-N-(5-amino-1-hydroxymethyl-pentyl)-4-fluoro-N-isobutyl-benzenesulfonamide (XII) (step B) as described in general procedure B using (2S)-2-[(morpholine-4-carbonyl)-amino]-3-naphthalen-1-yl-propionic acid (see example 32, step A). The final product was obtained in 34% yield (14 mg).

LC-MS: 672.3 (M+H)$^+$, >95% pure.

Example 54

Preparation of (1S,5S)-N-(1-{5-[(4-Amino-benzenesulfonyl)-isobutyl-amino]-6-hydroxy-hexylcarbamoyl}-2-naphthalen-2-yl-ethyl)-nicotinanide (MX-176)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure E using nicotinic acid. The final product was obtained in 64% yield.

LC-MS: 646.3 (M+H)$^+$, >95% pure; $^1$H NMR (CD$_3$OD): δ 0.92–0.88 (m, 7H), 1.20–1.11 (m, 1H), 1.29–1.24 (m, 3H), 1.38 (m, 1H), 1.89–1.86 (m, 1H), 2.82–2.77 (dd, J=7.0, 14.3, 1H), 2.96–2.91 (m, 2H), 3.17–3.09 (m, 1H), 3.25–3.21 (m, 1H), 3.45–3.36 (m, 2H), 3.59–3.48 (m, 2H), 4.89–4.87 (m, 1H), 6.67 (d, J=9.1, 2H), 7.49–7.44 (m, 5H), 7.88–7.79 (m, 5H), 8.15 (s, 1H), 8.64 (s, 1H), 8.88 (s, 1H).

Example 55

Preparation of (1S,5S)-N-(1-{5-[(4-Amino-benzenesulfonyl)-isobutyl-amino]-6-hydroxy-hexylcarbamoyl}-2-naphthalen-2-yl-ethyl)-isonicotinamide (MX-177)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure E using isonicotinic acid. The final product was obtained in 46% yield.

LC-MS: 646.3 (M+1)$^+$, >95% pure; $^1$H NMR (CD$_3$OD): δ 0.92–0.88 (m, 7H), 1.02–1.00 (m, 1H), 1.26–1.16 (m, 3H), 1.40–1.38 (m, 1H), 1.90–1.86 (m, 1H), 2.82–2.78 (dd, J=6.6, 14.8, 1H), 2.96–2.91 (m, 2H), 3.13–3.09 (m, 1H), 3.25–3.22 (m, 1H), 3.44–3.36 (m, 2H), 3.51–3.48 (m, 2H), 4.87 (d, J=7.4, 1H), 6.67 (d, J=8.4, 2H), 7.45 (m, 5H), 7.83–7.68 (m, 6H), 8.63 (d, J=5.1, 2H).

Example 56

Preparation of (1S,5S)-[1-{5-[(3-Amino-4-fluoro-benzenesulfonyl)-isobutyl-amino]-6-hydroxy-hexylcarbamoyl}-2-(3'-fluoro-biphenyl-2-yl)-ethyl]-carbamic Acid Methyl Ester (MX-178)

Step A. Preparation of (2S)-3-(3'-Fluoro-biphenyl-2-yl)-2-methoxycarbonylamino-propionic Acid 200 mg of (2S)-3-(2-bromo-phenyl)-2-methoxycarbonylamino-propionic acid (example 31, step A) and 100 mg 3-fluorophenyl boronic acid are dissolved in 5 mL warm 1 M Na$_2$CO$_3$ followed by 2 mL EtOH. The mixture is degassed for 15 min after which 100 mg of 10% Pd/C Degussa type E 101 is added. The solution is then heated to reflux for 4 h after which it is cooled and filtered through a thin pad of celite. The solids are washed with 1 M NaOH aliquots (2 mL) and the aqueous solution extracted once with 20 mL EtOAc. The aqueous phase is then acidified with 6N HCl and the resulting solution extracted with EtOAc (2×20 mL). The organic extracts are then combined and evaporated to yield 210 mg of product 99%. This material was used as such in the next step.

Step B. Preparation of (1S,5S)-[1-{5-[(3-Amino-4-fluoro-benzenesulfonyl)-isobutyl-amino]-6-hydroxy-hexylcarbamoyl}-2-(3'-fluoro-biphenyl-2-yl)-ethyl]-carbamic Acid Methyl Ester This derivative was prepared from (1S)-3-amino-N-(5-amino-1-hydroxymethyl-pentyl)-4-fluoro-N-isobutyl-benzenesulfonamide (XII) (example 53, step C) as described in general procedure B using (2S)-3-(3'-fluoro-biphenyl-2-yl)-2-methoxycarbonylamino-propionic acid (step A). The final product was obtained in 26% yield (14 mg).

LC-MS: 661.2 (M+H)$^+$, >95% pure.

Example 57

Preparation of (1S,5S)-[1-{5-[(4-Amino-3-chloro-benzenesulfonyl)-isobutyl-amino]-6-hydroxy-hexylcarbamoyl}-2-(3'-fluoro-biphenyl-2-yl)-ethyl]-carbamic Acid Methyl Ester (MX-179)

This derivative was prepared from (1S)-4-amino-N-(5-amino-1-hydroxymethyl-pentyl)-3-chloro-N-isobutyl-benzenesulfonamide (XII) (example 44, step B) as described in general procedure B using (2S)-3-(3'-fluoro-biphenyl-2-yl)-2-methoxycarbonylamino-propionic acid (see example 56, step A). The final product was obtained in 22% yield (19 mg).

LC-MS: 677.2 (M+H)$^+$, >95% pure.

Example 58

Preparation of (1S,5S)-(1-{5-[(3-Amino-4-fluoro-benzenesulfonyl)-isobutyl-amino]-6-hydroxy-hexylcarbamoyl}-2,2-diphenyl-ethyl)-carbamic Acid Methyl Ester (MX-180)

This product was prepared from (1S)-3-amino-N-(5-amino-1-hydroxymethyl-pentyl)-4-fluoro-N-isobutyl-benzenesulfonamide (XII) (example 53, step B) as described in general procedure B using (2S)-2-methoxycarbonylamino-3,3-diphenyl-propionic acid (example 34, step A). The final product was obtained in 71% yield (34 mg).

LC-MS: 643.3 (M+H)$^+$, >95% pure; $^1$H NMR (CD$_3$OD): δ 0.71–0.85 (m, 2H), 0.88 (d, J=6.3, 6H), 0.91–0.96 (m, 2H), 1.21–1.29 (m, 1H), 1.41–1.52 (m, 1H) 1.82–1.92 (m, 1H), 2.61–2.68 (m, 1H), 2.81–2.85 (m, 2H), 2.94–3.05 (m, 2H), 3.38–3.40 (t, J=5.0, 1H), 3.49–3.52 (m, 5H), 4.28 (d, J=10.0, 1H), 4.87 (d, J=10.0, 1H) 6.95–7.06 (m, 2H), 7.15–718 (m, 2H), 7.20–7.31 (m, 8H), 7.33 (d, J=7.9, 2H).

Example 59

Preparation of (1S,5S)-(1-{5-[(4-Amino-benzenesulfonyl)-isobutyl-amino]-6-hydroxy-hexylcarbamoyl}-2-biphenyl-4-yl-ethyl)-carbamic Acid tert-Butyl Ester (MX-189)

The title compound was prepared from the amine, (1S)-4-amino-N-(5-amino-1-hydroxymethyl-pentyl)-N-isobutyl-benzenesulfonamide (XII) (example 28, step D), and the acid, (2S)-3-biphenyl-4-yl-2-tert-butoxycarbonylamino-propionic acid, as described in general procedure E. The final product was obtained in 67% yield.

LC-MS: 667.4 (M+H)$^+$, >95% pure.

Example 60

Preparation of (1S,5S)-Cyclopentanecarboxylic Acid (1-{5-[(4-Amino-benzenesulfonyl)-isobutyl-amino]-6-hydroxy-hexylcarbamoyl}-2-naphthalen-2-yl-ethyl)-amide (MX-190)

The title compound was prepared from (2S,5S)-2-amino-N-{5-[(4-amino-benzenesulfonyl)-isobutyl-amino]-6- hydroxy-hexyl}-3-naphthalen-2-yl-propionamide (product of example 49) as described in general procedure D using cyclopentanecarbonyl chloride. The final product was obtained in 57% yield.

LC-MS: 637.3 (M+H)$^+$, >90% pure; $^1$H NMR (CD$_3$OD): δ 0.90–0.86 (m, 7H), 0.99–0.96 (m, 1H), 1.29–1.13 (m, 3H), 1.80–1.38 (m, 8H), 1.90–1.88 (m, 1H), 2.64–2.61 (m, 1H), 2.97–2.78 (m, 3H), 3.11–3.04 (m, 2H), 3.26–3.23 (m, 1H), 3.39–3.37 (m, 1H), 3.52–3.45 (m, 2H), 4.65 (t, J=7.4, 1H), 6.67 (d, J=8.4, 2H), 7.46–7.38 (m, 5H), 7.68 (s, 1H), 7.83–7.77 (m, 3H).

Example 61

Preparation of (1S,5S)-N-(1-{5-[(4-Amino-benzenesulfonyl)-isobutyl-amino]-6-hydroxy-hexylcarbamoyl}-2-naphthalen-2-yl-ethyl)-3,3,3-trifluoro-propionamide (MX-191)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure E using 3-trifluoropropionic acid. The product was obtained in 42% yield.

LC-MS: 651.3 (M+H)$^+$, >85% pure; $^1$H NMR (CD$_3$OD): δ 0.82–0.76 (m, 1H), 0.89–0.88 (m, 7H), 1.15–1.09 (m, 2H), 1.23–1.16 (m, 1H), 1.35–1.29 (m, 1H), 1.89–1.83 (m, 1H), 2.85–2.76 (m, 2H), 2.96–2.92 (m, 1H), 3.17–3.05 (m, 2H), 3.23–3.20 (m, 3H), 3.51–3.34 (m, 3H), 4.66 (t, J=7.9, 1H), 6.67 (d, J=8.5, 2H), 7.47–7.38 (m, 5H), 7.68 (s, 1H), 7.83–7.78 (m, 3H).

Example 62

Preparation of (1S,5S)-Pyrazine-2-carboxylic Acid (1-{5-[(4-Amino-benzenesulfonyl)-isobutyl-amino]-6-hydroxy-hexylcarbamoyl}-2-naphthalen-2-yl-ethyl)-amide (MX-192)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure E using pyrazine-2-carboxylic acid. The final product was obtained in 64% yield.

LC-MS: 647.3 (M+H)$^+$, >95% pure; $^1$H NMR (CD$_3$OD): δ 0.88–0.86 (m, 7H), 1.00–0.92 (m, 1H), 1.29–1.17 (m, 3H), 1.45–1.39 (m, 1H), 1.89–1.84 (m, 1H), 2.86–2.77 (m, 1H), 2.99–2.91 (m, 2H), 3.13–3.08 (m, 1H), 3.45–3.34 (m, 3H), 3.51–3.48 (m, 2H), 4.91–4.87 (m, 1H), 6.66 (d, J=8.4, 2H), 7.45–7.42 (m, 5H), 7.81–7.73 (m, 4H), 8.63 (s, 1H), 8.76 (s, 1H), 9.16 (s, 1H).

Example 63

Preparation of (2S,5S)-N-{5-[(4-Amino-benzenesulfonyl)-isobutyl-amino]-6-hydroxy-hexyl}-2-isobutylamino-3-naphthalen-2-yl-propionamide (MX-193)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using isobutyraldehyde. The final product was obtained in 57% yield.

LC-MS: 597.3 (M+H)$^+$, >80% pure; $^1$H NMR (CD$_3$OD): δ 0.96–0.75 (m, 14H), 1.07–1.01 (m, 2H), 1.24–1.10 (m, 1H), 1.33–1.26 (m, 1H), 1.71–1.66 (m, 1H), 1.91–1.83 (m, 1H), 2.34–2.25 (m, 2H), 2.84–2.75 (m, 2H), 2.94–2.90 (m, 1H), 3.10–3.04 (m, 3H), 3.44–3.33 (m, 2H), 3.50–3.45 (m, 2H), 6.66 (d, J=8.5, 2H), 7.49–7.36 (m, 5H), 7.65 (s, 1H), 7.83–7.77 (m, 3H).

Example 64

Preparation of (2S,5S)-N-{5-[(4-Amino-benzenesulfonyl)-isobutyl-amino]-6-hydroxy-hexyl}-3-naphthalen-2-yl-2-propylamino-propionamide (MX-194)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using propionaldehyde. The final product was obtained in 40% yield.

LC-MS: 583.3 (M+H)$^+$, >85% pure; $^1$H NMR (CD$_3$OD): δ 0.84–0.74 (m, 1H), 0.89–0.86 (m, 10H), 1.09–0.98 (m, 2H), 1.16–1.12 (m, 1H), 1.27–1.25 (m, 1H), 1.53–1.43 (m, 2H), 1.87–1.83 (m, 1H), 2.47–2.44 (m, 2H), 2.81–2.74 (m, 2H), 2.93–2.89 (m, 1H), 3.08–3.01 (m, 3H), 3.48–3.32 (m, 4H), 6.67 (d, J=8.3, 2H), 7.49–7.35 (m, 5H), 7.64 (s, 1H), 7.83–7.77 (m, 3H).

Example 65

Preparation of (2S,5S)-N-{5-[(4-Amino-benzenesulfonyl)-isobutyl-amino]-6-hydroxy-hexyl}-2-ethylamino-3-naphthalen-2-yl-propionamide (MX-195)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using acetaldehyde. The final product was obtained in 37% yield.

LC-MS: 569.3 (M+H)$^+$, >85% pure; $^1$H NMR (CD$_3$OD): δ 0.73–0.70 (m, 1H), 0.89–0.81 (m, 7H), 1.01–0.98 (m, 2H), 1.13–1.07 (m, 4H), 1.29–1.22 (m, 1H), 1.89–1.82 (m, 1H), 2.60–2.48 (m, 2H), 2.79–2.74 (m, 2H), 2.98–2.89 (m, 1H), 3.09–3.00 (m, 3H), 3.47–3.32 (m, 4H), 6.65 (d, J=8.3, 2H), 7.46–7.34 (m, 5H), 7.64 (s, 1H), 7.83–7.77 (m, 3H).

Example 66

Preparation of (1S,5S)-Morpholine-4-carboxylic Acid (1-{5-[(Benzo[1,3]dioxole-5-sulfonyl)-isobutyl-amino]-6-hydroxy-hexylcarbamoyl}-2-naphthalen-1-yl-ethyl)-amide (MX-199)

Step A, Preparation of Nα-Isobutyl-Nα-(3,4-methylenedioxybenzenesulfonyl)-L-α-amino-ε-caprolactam (2S)-3-Isobutylamino-azepan-2-one (example 28, step A) 1.0 g was dissolved in DCM (20.0 mL) and treated with 2 ml triethylamine followed by the addition of 3,4-methylenedioxybenzenesulfonyl chloride (900 mg). A 0.05 g portion of DMAP was added and the mixture was stirred 5 h. The resulting solution was poured into mL 0.5 M HCl and shaken vigorously. The organic phase was dried and evaporated to give (1.30 mg) of clean product.

$^1$H NMR (DMSO-d$_6$): δ 0.93 (d, J=6.0, 3H), 0.96 (d, J=6.0, 3H), 1.26–1.47 (m, 1H), 1.85–1.65 (m, 3H), 2.08–2.28 (m and s, 6H), 2.97–3.07 (m, 1H), 3.11–3.33 (m, 3H), 4.65 (d, J=9.0, 1H), 6.02 (s, 2H), 6.88 (d, J=6.6, 1H), 7.14 (s, 1H), 7.30 (d, J=6.7 1H).

Step B. Preparation of (1S)-Benzo[1,3]dioxole-5-sulfonic Acid (5-Amino-1-hydroxymethyl-pentyl)-isobutyl-amide This compound was prepared from Nα-isobutyl-Nα-(3, 4-methylenedioxybenzenesulfonyl)-L-α-amino-ε-caprolactam (step A) in a three step reaction sequence (Boc activation, reductive ring opening and deprotection) as described for the preparation of (1S)-4-amino-N-(5-amino-1-hydroxymethyl-pentyl)-N-isobutyl-benzenesulfonamide (example 28, steps C and D). The final product was obtained in 75% yield and was used as such in the next step.

Step C. Preparation of (1S,5S)-Morpholine-4-carboxylic Acid (1-{5-[(Benzo[1,3]dioxole-5-sulfonyl)-isobutyl-amino]-6-hydroxy-hexylcarbamoyl}-2-naphthalen-1-yl-ethyl)-amide This derivative was prepared from (1S)-benzo[1,3] dioxole-5-sulfonic acid (5-amino-1-hydroxymethyl-pentyl)-isobutyl-amide (XII) (step B) as described in general procedure B using (2S)-2-[(morpholine-4-carbonyl)-amino]-3-naphthalen-1-yl-propionic acid (see example 32, step A). The final product was obtained in 51% yield (52 mg).

LC-MS: 683.3 (M+H)$^+$, >95% pure.

Example 67

Preparation of (1S,5S)-(1-{5-[(Benzo[1,3]dioxole-5-sulfonyl)-isobutyl-amino]-6-hydroxy-hexylcarbamoyl}-2,2-diphenyl-ethyl)-carbamic Acid Methyl Ester (MX-200)

The title compound was prepared from (1S)-benzo[1,3] dioxole-5-sulfonic acid (5-amino-1-hydroxymethyl-pentyl)-isobutyl-amide (XII) (example 66, step B) as described in general procedure B using (2S)-2-methoxycarbonylamino-3,3-diphenyl-propionic acid (see example 34, step A). The final product was obtained in 71% yield (141 mg).

LC-MS: 654.3 (M+H)$^+$, >95% pure; $^1$H NMR (CD$_3$OD): δ 0.71–0.85 (m, 2H), 0.88 (d, J=6.6, 6H), 1.01–1.08 (m, 2H), 1.21–1.29 (m, 1H), 1.41–1.52 (m, 1H) 1.82–1.92 (m, 1H), 2.61–2.68 (m, 1H), 2.81–2.87 (m, 2H), 2.92–3.01 (m, 2H), 3.38–3.40 (t, J=5.0, 1H), 3.49–3.52 (m, 5H), 4.25 (d, J=11.0, 1H), 4.89 (d, J=11.0, 1H), 6.02 (s, 2H) 6.95–7.06 (m, 2H), 7.15–718 (m, 2H), 7.20–7.31 (m, 8H), 7.33 (d, J=7.9, 2H).

Example 68

Preparation of (2S,5S)-N-{5-[(4-Amino-benzenesulfonyl)-isobutyl-amino]-6-hydroxy-hexyl}-2-butylamino-3-naphthalen-2-yl-propionamide (MX-208)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using butyraldehyde. The final product was obtained in 13% yield.

LC-MS: 597.3 (M+H)$^+$, >85% pure; $^1$H NMR (CD$_3$OD): δ 0.86–0.75 (m, 1H), 0.97–0.88 (m, 7H), 1.15–1.01 (m, 5H), 1.33–1.23 (m, 4H), 1.48–1.41 (m, 2H), 1.88–1.82 (m, 1H), 2.51–2.46 (m, 2H), 2.81–2.74 (m, 2H), 2.94–2.89 (m, 1H), 3.08–3.01 (m, 3H), 3.47–3.33 (m, 4H), 6.67 (d, J=8.4, 2H), 7.47–7.35 (m, 5H), 7.65 (s, 1H), 7.83–7.77 (m, 3H).

Example 69

Preparation of (2S,5S)-N-{5-[(4-Amino-benzenesulfonyl)-isobutyl-amino]-6-hydroxy-hexyl}-2-(2,2-dimethyl-propylamino)-3-naphthalen-2-yl-propionamide (MX-209)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using trimethylacetaldehyde. The final product was obtained in 47% yield.

LC-MS: 611.4 (M+H)$^+$, >90% pure; $^1$H NMR (CD$_3$OD): δ 0.92–0.82 (m, 16H), 0.98–0.94 (m, 1H), 1.20–1.08 (m, 2H), 1.25–1.20 (m, 1H), 1.35–1.31 (m, 1H), 1.89–1.84 (m, 1H), 2.24 (s, 2H), 2.94–2.77 (m, 3H), 3.13–3.03 (m, 3H), 3.37–3.34 (m, 2H), 3.49–3.44 (m, 2H), 6.66 (d, J=8.5, 2H), 7.47–7.37 (m, 5H), 7.67 (s, 1H), 7.84–7.78 (m, 3H).

Example 70

Preparation of (2S,5S)-N-{5-[(4-Amino-benzenesulfonyl)-isobutyl-amino]-6-hydroxy-hexyl}-3-naphthalen-2-yl-2-[(pyridin-2-ylmethyl)-amino]-propionamide (MX-210)

The title compound was prepared from (2S,5S)-2-amino-N-{5-[(4-amino-benzenesulfonyl)-isobutyl-amino]-6-hydroxy-hexyl}-3-naphthalen-2-yl-propionamide (product of example 49) as described in general procedure F using 2-pyridinecarboxaldehyde. The final product was obtained in 26% yield.

LC-MS: 632.3 (M+H)$^+$, >95% pure; $^1$H NMR (CD$_3$OD): δ 0.95–0.87 (m, 8H), 1.38–1.12 (m, 4H), 1.89–1.85 (m, 1H), 2.78 (dd, J=6.7, 14.3, 1H), 2.95–2.86 (m, 2H), 3.17–3.01 (m, 3H), 3.50–3.36 (m, 4H), 3.71 (d, J=14.2, 1H), 3.84 (d, J=14.2, 1H), 6.66 (d, J=8.4, 2H), 7.20–7.23 (m, 1H), 7.33–7.28 (m, 2H), 7.47–7.42 (m, 4H), 7.67–7.64 (m, 2H), 7.83–7.76 (m, 3H), 8.35 (d, J=5.0, 1H).

Example 71

Preparation of (2S,5S)-2-Acetylamino-N-{5-[(4-amino-benzenesulfonyl)-isobutyl-amino]-6-hydroxy-hexyl}-3,3-diphenyl-propionamide (MX-211)

Step A. Preparation (2S)-2-Acetylamino-3,3-diphenyl-propionic Acid

To a solution of L-diphenylalanine (100 mg, 0.4 mmol) (Peptech Corp.) in 5 mL 1N NaOH and 0.5 mL saturated Na$_2$CO$_3$ (resulting solution at pH 10) was added acetyl chloride (0.5 mmol) dissolved in 5 mL. Afterwards, the reaction mixture was stirred at room temperature for 2 h. The alkaline solution was extracted once with ether (10 mL) and the aqueous phase was acidified with 1N HCl. This was extracted twice with 20 mL EtOAc, and the combined organic phases were washed with 50 mL 1N HCl. The organic phase was dried over Na$_2$SO$_4$, filtered and evaporated to an oil which solidifies to yields 70 mg (60%) of the desired material. This crude intermediate was used as such in the next step.

Step B. Preparation of (2S,5S)-2-Acetylamino-N-{5-[(4-amino-benzenesulfonyl)-isobutyl-amino]-6-hydroxy-hexyl}-3,3-diphenyl-propionamide The title compound was prepared from (1S)-4-amino-N-(5-amino-1-hydroxymethyl-pentyl)-N-isobutyl-benzenesulfonamide (XII) (example 28, step D) as described in general procedure B using (2S)-2-acetylamino-3,3-diphenyl-propionic acid (step A). The final product was obtained in 56% yield (95 mg).

LC-MS: 609.3 (M+H)$^+$, >95% pure; $^1$H NMR (CD$_3$OD): δ 0.71–0.85 (m, 2H), 0.88 (d, J=6.3, 7H), 0.96–1.02 (m, 1H), 1.29–1.34 (m, 1H), 1.41–1.52 (m, 1H), 1.75 (s, 3H), 1.82–1.92 (m, 1H), 2.61–2.68 (m, 1H), 2.81–2.85 (m, 2H), 2.90–2.98 (m, 2H), 3.38–3.40 (t, J=5.0, 1H), 3.40–3.41 (m, 1H), 3.49–3.52 (m, 3H), 4.28 (d, J=11.0, 1H), 5.11 (d, J=11.0, 1H) 6.69 (d, J=8.0, 2H), 7.15–718 (m, 2H), 7.20–7.31 (m, 6H), 7.33 (d, J=7.9, 2H), 7.47 (d, J=7.5 1H).

Example 72

Preparation of (2S,5S)-2-Amino-N-{5-[(4-amino-benzenesulfonyl)-isobutyl-amino]-6-hydroxy-hexyl}-3,3-diphenyl-propionamide (MX-233)

The compound was prepared from general procedure A using (2S)-2-tert-butoxycarbonylamino-3,3-diphenyl-propionic acid and (1S)-4-amino-N-(5-amino-1-hydroxymethyl-pentyl)-N-isobutyl-benzenesulfonamide (XII) (example 28, step D) but the product was purified by flash chromatography yielding 49% of the Boc derivative. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-3,3-diphenyl-propionamide (see example 24). The product was used without further purification to conduct to a series of diphenyl-propionamide—lysine derived tests compounds.

LC-MS: 567.3 (M+H)$^+$, >95% pure.

Example 73

Preparation of (1S,5S)-N-(1-{5-[(4-Amino-benzenesulfonyl)-isobutyl-amino]-6-hydroxy-hexylcarbamoyl}-2,2-diphenyl-ethyl)-nicotinamide (MX-221)

The title compound was then obtained in 65% yield using (2S,5S)-2-amino-N-{5-[(4-amino-benzenesulfonyl)-isobutyl-amino]-6-hydroxy-hexyl}-3,3-diphenyl-propionamide (product of example 72) and nicotinic acid with general procedure A. However, 1.0N NaOH was used instead of 1.0N hydrochloric acid for the preparation of the title compound.

LC-MS: 672.3 (M+H)$^+$, >98% pure; $^1$H NMR (CD$_3$OD): δ 0.69–0.81 (m, 1H), 0.81–0.92 (m, 1H), 0.90 (d, J=6.6, 6H), 0.92–1.02 (m, 1H), 1.18–1.29 (m, 1H), 1.39–1.49 (m, 1H), 1.83–1.93 (m, 1H), 2.64–2.73 (m, 1H), 2.82 (dd, J=6.8, 14.3, 1H), 2.91–3.03 (m, 2H), 3.40 (dd, J=6.5, 10.3, 1H), 3.45–3.52 (m, 1H), 3.54 (dd, J=5.5, 10.3, 1H), 4.55 (d, J=11.9, 1H), 5.43 (d, J=11.9, 1H), 6.71 (d, J=8.6, 2H), 7.13–7.24 (m, 2H), 7.25–7.33 (m, 4H), 7.39 (d, J=7.5, 2H), 7.40–7.47 (m, 3H), 7.50 (d, J=8.6, 2H), 7.96 (dd, J=1.8, 8.0, 1H), 8.59–8.64 (m, 2H).

Example 74

Preparation of (1S,5S)-N-(1-{5-[(4-Amino-benzenesulfonyl)-isobutyl-amino]-6-hydroxy-hexylcarbamoyl}-2,2-diphenyl-ethyl)-isonicotinamide (MX-222)

The title compound was then obtained in 76% yield using (2S,5S)-2-amino-N-{5-[(4-amino-benzenesulfonyl)-isobutyl-amino]-6-hydroxy-hexyl}-3,3-diphenyl-propionamide (product of example 72) and isonicotinic acid with general procedure A. However, 1.0N NaOH was used instead of 1.0N hydrochloric acid for the preparation of the title compound.

LC-MS: 672.2 (M+H)$^+$, >98% pure; $^1$H NMR (CD$_3$OD): δ 0.70–0.80 (m, 1H), 0.81–0.90 (m, 1H), 0.90 (d, J=6.6, 6H), 0.93–1.04 (m, 2H), 1.19–1.30 (m, 1H), 1.38–1.47 (m, 1H), 1.82–1.92 (m, 1H), 2.64–2.73 (m, 1H), 2.83 (dd, J=6.8, 14.4, 1H), 2.91–3.02 (m, 2H), 3.41 (dd, J=6.4, 10.3, 1H), 3.45–3.53 (m, 1H), 3.54 (dd, J=5.5, 10.3, 1H), 4.55 (d, J=11.8, 1H), 5.43 (d, J=11.8, 1H), 6.71 (d, J=8.7, 2H), 7.15–7.24 (m, 2H), 7.25–7.32 (m, 4H), 7.38 (d, J=7.3, 2H), 7.43 (d, J=7.5, 2H), 7.46–7.52 (m, 4H), 8.58 (dd, J=1.5, 4.7, 2H).

Example 75

Preparation of (1S,5S)-Cyclopropanecarboxylic Acid (1-{5-[(4-Amino-benzenesulfonyl)-isobutyl-amino]-6-hydroxy-hexylcarbamoyl}-2,2-diphenyl-ethyl)-amide (MX-227)

The title compound was then obtained in 22% yield using (2S,5S)-2-amino-N-{5-[(4-amino-benzenesulfonyl)-isobutyl-amino]-6-hydroxy-hexyl}-3,3-diphenyl-propionamide (product of example 72) and cyclopropanecarbonyl chloride with general procedure C.

LC-MS 635.2 (M+H)$^+$, >98% pure; $^1$H NMR (CD$_3$OD): δ 0.55–0.65 (m, 1H), 0.66–0.74 (m, 3H), 0.75–0.86 (m, 2H), 0.88–0.98 (m, 2H), 0.91 (d, J=6.6, 6H), 1.17–1.28 (m, 1H), 1.38–1.50 (m, 2H), 1.83–1.94 (m, 1H), 2.58–2.67 (m, 1H), 2.83 (dd, J=6.7, 14.4, 1H), 2.91–3.02 (m, 2H), 3.41 (dd, J=6.7, 10.5, 1H), 3.45–3.52 (m, 1H), 3.55 (dd, J=5.4, 10.5, 1H), 4.39 (d, J=11.7, 1H), 5.19 (d, J=11.7, 1H), 6.71 (d, J=8.7, 2H), 7.15–7.21 (m, 2H), 7.22–7.38 (m, 8H), 7.50 (d, J=8.7, 2H).

Example 76

Preparation of (1S,5S)-Cyclohexanecarboxylic Acid (1-{5-[(4-Amino-benzenesulfonyl)-isobutyl-amino]-6-hydroxy-hexylcarbamoyl}-2,2-diphenyl-ethyl)-amide (MX-224)

The title compound was then obtained in 66% yield using (2S,5S)-2-amino-N-{5-[(4-amino-benzenesulfonyl)-isobutyl-amino]-6-hydroxy-hexyl}-3,3-diphenyl-propionamide (product of example 72) and cyclohexanecarbonyl chloride with general procedure C.

LC-MS: 677.4 (M+H)$^+$, >98% pure; $^1$H NMR (CD$_3$OD): δ 0.65–0.85 (m, 2H), 0.88–0.98 (m, 2H), 0.90 (d, J=6.6, 6H), 1.07–1.27 (m, 6H), 1.28–1.46 (m, 2H), 1.54–1.65 (m, 3H), 1.65–1.72 (m, 1H), 1.82–1.92 (m, 1H), 1.96–2.05 (m, 1H), 2.58–2.66 (m, 1H), 2.82 (dd, J=6.7, 14.4, 1H), 2.90–3.00 (m, 2H), 3.40 (dd, J=6.6, 10.5, 1H), 3.42–3.50 (m, 1H), 3.54 (dd, J=5.5, 10.5, 1H), 4.36 (d, J=11.8, 1H), 5.17 (d, J=11.8, 1H), 6.70 (d, J=8.6, 2H), 7.14–7.20 (m, 2H), 7.21–7.29 (m, 4H), 7.30–7.37 (m, 4H), 7.49 (d, J=8.6, 2H).

Example 77

Preparation of (1S,3R,S,5S)-Tetrahydro-furan-3-carboxylic Acid (1-{5-[(4-Amino-benzenesulfonyl)-isobutyl-amino]-6-hydroxy-hexylcarbamoyl}-2,2-diphenyl-ethyl)-amide (MX-223)

The title compound was then obtained in 72% yield using (2S,5S)-2-amino-N-{5-[(4-amino-benzenesulfonyl)-isobutyl-amino]-6-hydroxy-hexyl}-3,3-diphenyl-propionamide (product of example 72) and (3R,S)-tetrahydro-furan-3-carboxylic acid with general procedure A.

LC-MS: 665.3 (M+H)$^+$, >98% pure; $^1$H NMR (CD$_3$OD): δ 0.67–0.89 (m, 2H), 0.90–1.00 (m, 2H), 0.91 (d, J=6.6, 6H), 1.18–1.27 (m, 1H), 1.38–1.56 (m, 1.5H), 1.72–1.81 (m, 0.5H), 1.85–2.06 (m, 2H), 2.60–2.69 (m, 1H), 2.80–2.90 (m, 2H), 2.93–3.01 (m, 2H), 3.17 (dd, J=6.3, 8.5, 0.5H), 3.41 (dd, J=6.6, 10.4, 1H), 3.45–3.57 (m, 2.5H), 3.59–3.72 (m, 1.5H), 3.73–3.82 (m, 1.5H), 4.35 and 4.36 (2d, J=11.7, 1H), 5.21 and 5.22 (2d, J=11.7, 1H), 6.71 (d, J=8.6, 2H), 7.16–7.22 (m, 2H), 7.23–7.31 (m, 4H), 7.32–7.40 (m, 4H), 7.50 (d, J=8.6, 2H).

Example 78

Preparation of (1S,5S)-(1-{5-[(4-Fluoro-benzenesulfonyl)-isobutyl-amino]-6-hydroxy-hexylcarbamoyl}-2,2-diphenyl-ethyl)-carbamic Acid Methyl Ester (MX-220)

Step A. Preparation of (2S)-4-Fluoro-N-isobutyl-N-(2-oxo-azepan-3-yl)-benzenesulfonamide (2S)-3-Isobutylamino-azepan-2-one (example 28, step A) 200 mg was dissolved in DCM (20.0 mL) and treated with 1 mL triethylamine followed by 4-fluoro-benzenesulfonyl chloride (200 mg). A 0.01 g portion of DMAP was added and the mixture was stirred 5 h. The resulting thick slush was poured into 40 mL 0.5 M HCl and shaken vigorously. The solid in the biphasic solution was filtered out and washed with cold acetone to give 251 mg of a clean product.

Step B. Preparation of (1S)-N-(5-Amino-1-hydroxymethyl-pentyl)-4-fluoro-N-isobutyl-benzenesulfonamide This compound was prepared from (2S)-4-fluoro-N-isobutyl-N-(2-oxo-azepan-3-yl)-benzenesulfonamide (step A) in a three step reaction sequence (Boc activation, reductive ring opening and deprotection) as described for the preparation of (1S)-4-amino-N-(5-amino-1-hydroxymethyl-pentyl)-N-isobutyl-benzenesulfonamide (example 28, steps C and D). The final product was obtained in 47% yield. It was used as such in the next step.

Step C. Preparation of (1S,5S)-(1-{5-[(4-Fluoro-benzenesulfonyl)-isobutyl-amino]-6-hydroxy-hexylcarbamoyl}-2,2-diphenyl-ethyl)-carbamic Acid Methyl Ester This derivative was prepared from (1S)-N-(5-amino-1-hydroxymethyl-pentyl)-4-fluoro-N-isobutyl-benzenesulfonamide (XII) (this example, step B as described in general procedure E using (2S)-2-methoxycarbonylamino-3,3-diphenyl-propionic acid (product of example 34, step A). The final product was obtained in 48% yield.

LC-MS: 628 (M+H)$^+$, >95% pure.

Example 79

Preparation of (1S,5S)-1-{5-[(4-Cyano-benzenesulfonyl)-isobutyl-amino]-6-hydroxy-hexylcarbamoyl}-2,2-diphenyl-ethyl)-carbamic Acid Methyl Ester (MX-230)

Step A. Preparation of (2S)-4-Cyano-N-isobutyl-N-(2-oxo-azepan-3-yl)-benzenesulfonamide (2S)-3-Isobutylamino-azepan-2-one (example 28, step A) 400 mg was dissolved in DCM (20.0 mL) and treated with 1 mL triethylamine followed by 4-cyano-benzenesulfonyl chloride (400 mg). A 0.01 g portion of DMAP was added and the mixture was stirred 5 h. The resulting thick slush was poured into 40 mL 0.5 M HCl and shaken vigorously. The solid in the biphasic solution was filtered out and washed with cold acetone to give 600 mg of a clean product.

Step B. Preparation of (1S)-N-(5-Amino-1-hydroxymethyl-pentyl)-4-cyano-N-isobutyl-benzenesulfonamide This compound was prepared from (2S)-4-cyano-N-isobutyl-N-(2-oxo-azepan-3-yl)-benzenesulfonamide (step A) in a three step reaction sequence (Boc activation, reductive ring opening and deprotection, in this case with trifluoroacetic acid in DCM instead of HCl) as described for the preparation of (1S)-4-amino-N-(5-amino-1-hydroxymethyl-pentyl)-N-isobutyl-benzenesulfonamide (example 28, steps C and D). The final product was obtained in 50% yield. It was used as such in the next step.

Step C. Preparation of (1S,5S)-1-{5-[(4-Cyano-benzenesulfonyl)-isobutyl-amino]-6-hydroxy-hexylcarbamoyl}-2,2-diphenyl-ethyl)-carbamic Acid Methyl Ester This derivative was prepared from (1S)-N-(5-amino-1-hydroxymethyl-pentyl)-4-cyano-N-isobutyl-benzenesulfonamide (XII) (this example, step B) as described in general procedure E using (2S)-2-methoxycarbonylamino-3,3-diphenyl-propionic acid (product of example 34, step A). The final product was obtained in 7% yield.

LC-MS: 635 (M+H)$^+$, 97% pure.

Example 80

Preparation of (1S,5S)-(1-{5-[(2,4-Difluoro-benzenesulfonyl)-isobutyl-amino]-6-hydroxy-hexylcarbamoyl}-2,2-diphenyl-ethyl)-carbamic Acid Methyl Ester (MX-232)

Step A. Preparation of (2S)-2,4-Difluoro-N-isobutyl-N-(2-oxo-azepan-3-yl)-benzenesulfonamide (2S)-3-Isobutylamino-azepan-2-one (example 28, step A) 147 mg was dissolved in DCM (1.5 mL) and treated with 0.17 mL triethylamine followed by 2,4-difluoro-benzenesulfonyl chloride (170 mg). The mixture was stirred 24 h. The resulting thick slush was poured into 40 mL 0.5 M HCl and shaken vigorously. The solid in the biphasic solution was filtered out and washed with cold acetone to give 289 mg of a clean product.

Step B. Preparation of (1S)-N-(5-Amino-1-hydroxymethyl-pentyl)-2,4-difluoro-N-isobutyl-benzenesulfonamide This compound was prepared from (2S)-2,4-difluoro-N-isobutyl-N-(2-oxo-azepan-3-yl)-benzenesulfonamide (step A) in a three step reaction sequence (Boc activation, reductive ring opening and deprotection) as described for the preparation of (1S)4-amino-N-(5-amino-1-hydroxymethyl-pentyl)-N-isobutyl-benzenesulfonamide (example 28, steps C and D). The final product was obtained in 50% yield. It was used as such in the next step.

Step C. Preparation of (1S,5S)-(1-{5-[(2,4-Difluoro-benzenesulfonyl)-isobutyl-amino]-6-hydroxy-hexylcarbamoyl}-2,2-diphenyl-ethyl)-carbamic Acid Methyl Ester This derivative was prepared from (5S)-N-(5-amino-1-hydroxymethyl-pentyl)-2,4-difluoro-N-isobutyl-benzenesulfonamide (XII) (this example, step B) as described in general procedure E using (2S)-2-methoxycarbonylamino-3,3-diphenyl-propionic acid (product of example 34, step A). The final product was obtained in 7% yield.

LC-MS: 646 (M+H)$^+$, >95% pure.

Example 81

Preparation of (2S,5S)-2-Amino-N-{5-[(3-amino-4-fluoro-benzenesulfonyl)-isobutyl-amino]-6-hydroxy-hexyl}-3-naphthalen-2-yl-propionamide (MX-243)

This title compound was prepared from the hydrolysis of (1S,5S)-(1-{5-[(3-amino-4-fluoro-benzenesulfonyl)-isobutyl-amino]-6-hydroxy-hexylcarbamoyl}-2-naphthalen-2-yl-ethyl)-carbamic acid tert-butyl ester (example 90) as described in example 49. The yield obtained was 93%.

LC-MS: 559.2 (M+H)$^+$, >95% pure.

Example 82

Preparation of (1S,5S)-(1-{5-[(3-Amino-4-fluoro-benzenesulfonyl)-isobutyl-amino]-6-hydroxy-hexylcarbamoyl}-2-naphthalen-2-yl-ethyl)-carbamic Acid Methyl Ester (MX-244)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) using the same procedure used for the preparation of (2S)-2-methoxycarbonylamino-3-naphthalen-2-yl-propionic (example 28, step E). The final product was obtained in 98% yield.

LC-MS: 617.2 (M+H)$^+$, >95% pure.

Example 83

Preparation of (1S,5S)-(N-(1-{5-[(3-Amino-4-fluoro-benzenesulfonyl)-isobutyl-amino]-6-hydroxy-hexylcarbamoyl}-2-naphthalen-2-yl-ethyl)-nicotinamide (MX-245)

The title compound was prepared from (2S,5S)-2-amino-N-{5-[(3-amino4-fluoro-benzenesulfonyl)-isobutyl-amino]-6-hydroxy-hexyl}-3-naphthalen-2-yl-propionamide (example 81) as described in general procedure E using nicotinic acid. The final product was obtained in 35% yield.

LC-MS: 664.2 (M+H)$^+$, 95% pure.

Example 84

Preparation of (1S,5S)-N-(1-{5-[(3-Amino-4-fluoro-benzenesulfonyl)-isobutyl-amino]-6-hydroxy-hexylcarbamoyl}-2-naphthalen-2-yl-ethyl)-isonicotinamide (MX-246)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure E using isonicotinic acid. The final product was obtained in 66% yield.

LC-MS: 664.2 (M+H)$^+$, 85% pure.

Example 85

Preparation of (1S,5S)-Tetrahydro-furan-3-carboxylic Acid (1-{5-[(3-Amino-4-fluoro-benzenesulfonyl)-isobutyl-amino]-6-hydroxy-hexylcarbamoyl}-2-naphthalen-2-yl-ethyl)-amide (MX-247)

The title compound was prepared from (2S,5S)-2-amino-N-{5-[(3-amino4-fluoro-benzenesulfonyl)-isobutyl-amino]-6-hydroxy-hexyl}-3-naphthalen-2-yl-propionamide (example 81) as described in general procedure E using (3-R,S)-tetrahydro-3-furoic acid. The final product was obtained in 34% yield.

LC-MS: 657.2 (M+H)$^+$, 94% pure.

Example 86

Preparation of (2S,5S)-N-{5-[(3-Amino-4-fluoro-benzenesulfonyl)-isobutyl-amino]-6-hydroxy-hexyl}-2-(3,3-dimethyl-ureido)-3-naphthalen-2-yl-propionamide (MX-249)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure D using dimethylcarbamyl chloride. The final product was obtained in 57% yield.

LC-MS: 630.2 (M+H)$^+$, 95% pure.

Example 87

Preparation of (1S,5S)-Cyclopropanecarboxylic Acid (1-{5-[(3-Amino-4-fluoro-benzenesulfonyl)-isobutyl-amino]-6-hydroxy-hexylcarbamoyl}-2-naphthalen-2-yl-ethyl)-amide (MX-250)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure D using cyclopropanecarbonyl chloride. The final product was obtained in 48% yield.

LC-MS: 627.2 (M+H)$^+$, 94% pure.

Example 88

Preparation of (1S,5S)-Cyclohexanecarboxylic Acid (1-{5-[(3-Amino-4-fluoro-benzenesulfonyl)-isobutyl-amino]-6-hydroxy-hexylcarbamoyl}-2-naphthalen-2-yl-ethyl)-amide (MX-251)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure D using cyclohexanecarbonyl chloride. The final product was obtained in 48% yield.

LC-MS: 669.2 (M+H)$^+$, >95% pure.

Example 89

Preparation of (2S,5S)-2-Acetylamino-N-{5-[(3-amino-4-fluoro-benzenesulfonyl)-isobutyl-amino]-6-hydroxy-hexyl}-3-naphthalen-2-yl-propionamide (MX-252)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure D using acetyl chloride. The final product was obtained in 26% yield.

LC-MS: 601.3 (M+H)$^+$, 92% pure.

Example 90

Preparation of (1S,5S)-(1-{5-[(3-Amino-4-fluoro-benzenesulfonyl)-isobutyl-amino]-6-hydroxy-hexylcarbamoyl}-2-naphthalen-2-yl-ethyl)-carbamic Acid tert-Butyl Ester (MX-236)

The title compound was prepared from the crude amine mixture of (1S)-N-(5-amino-1-hydroxymethyl-pentyl)-N-isobutyl-3-amino-4-fluoro-benzenesulfonamide which is described earlier (example 53, step C, which was made from a batch of sulfonyl chloride containing the two regioisomers) and (2S)-2-tert-butoxycarbonylamino-3-naphthalen-2-yl-propionic acid using general procedure A. The crude residue was purified by semi-preparative HPLC in several batches of 80 mg using a gradient of 35 to 90% of acetonitrile over 30 min and a flow rate of 15 mL/min, retention time=23.9 min. All the pure fractions were combined to provide 460 mg (38% yield) of the title compound.

LC-MS: 659.2 (M+H)$^+$, >95% pure.

Example 91

Preparation of (1S,5S)-(1-{5-[(4-Amino-3-fluoro-benzenesulfonyl)-isobutyl-amino]-6-hydroxy-hexylcarbamoyl}-2-naphthalen-2-yl-ethyl)-carbamic Acid tert-Butyl Ester (MX-235)

The title compound was isolated as a side product of example 90 (18% yield). The crude amine mixture used as starting material also contained one third of (1S)-N-(5-amino-1-hydroxymethyl-pentyl)-N-isobutyl-4-amino-3-fluoro-benzenesulfonamide. The final compound was isolated within the same semi-preparative HPLC purifcation steps as described for example 90, retention time=23.2 min.

LC-MS: 659.2 (M+H)$^+$, >85% pure.

Example 92

Preparation of (1S,5S)-(1-{5-[(3-Amino-4-fluoro-benzenesulfonyl)-isobutyl-amino]-6-hydroxy-hexylcarbamoyl}-2,2-diphenyl-ethyl)-carbamic Acid tert-Butyl Ester (MX-XX)

The title compound was prepared from the crude amine mixture of (1S)-N-(5-amino-1-hydroxymethyl-pentyl)-N-isobutyl-3-amino-4-fluoro-benzenesulfonamide which is described earlier (example 53, step C) and (2S)-2-tert-butoxycarbonylamino-3,3-diphenyl-propionic acid using general procedure A. The crude residue was purified by semi-preparative HPLC in several batches of 80 mg using a gradient of 50 to 80% of acetonitrile over 30 min and a flow rate of 15 mL/min, retention time=20.2 min. All the pure fractions were combined to provide 630 mg (46% yield) of the title compound.

LC-MS: 685.2 (M+H)$^+$, >90% pure.

Example 93

Preparation of (1S,5S)-(1-{5-[(4-Amino-3-fluoro-benzenesulfonyl)-isobutyl-amino]-6-hydroxy-hexylcarbamoyl}-2,2-diphenyl-ethyl)-carbamic Acid tert-Butyl Ester (MX-XX)

The title compound was isolated as a side product of example 92 in 17% yield. The crude amine mixture used as starting material also contained one third of (1S)-N-(5-amino-1-hydroxymethyl-pentyl)-N-isobutyl-4-amino-3-fluoro-benzenesulfonamide. The final compound was isolated within the same semi-preparative HPLC purifcation steps as described for example 92, retention time=19.1 min.

LC-MS: 685.2 (M+H)$^+$, >85% pure.

Example 94

Preparation of (2S,5S)-N-{5-[(4-Amino-benzenesulfonyl)-isobutyl-amino]-6-hydroxy-hexyl}-2-(3,3-dimethyl-ureido)-3,3-diphenyl-propionamide (MX-237)

The title compound was obtained in 53% yield using (2S,5S)-2-amino-N-{5-[(4-amino-benzenesulfonyl)-isobutyl-amino]-6-hydroxy-hexyl}-3,3-diphenyl-propionamide (product of example 72) and dimethylcarbamoyl chloride with general procedure C.

LC-MS: 638.3 (M+H)$^+$, >98% pure.

Example 95

Preparation of (1S,5S)-(1-{5-[(4-Amino-benzenesulfonyl)-isobutyl-amino]-6-hydroxy-hexylcarbamoyl}-2,2-diphenyl-ethyl)-carbamic Acid Pyridin-2-ylmethyl Ester (MX-238)

The title compound was obtained in 34% yield using (2S,5S)-2-amino-N-{5-[(4-amino-benzenesulfonyl)-isobutyl-amino]-6-hydroxy-hexyl}-3,3-diphenyl-propionamide (product of example 72) and dimethylcarbamoyl chloride with general procedure G but without the acidic workup.

LC-MS: 702.2 (M+H)$^+$, >98% pure.

Example 96

Preparation of (1S,5S)-Pyridine-2-carboxylic Acid (1-{5-[(4-Amino-benzenesulfonyl)-isobutyl-amino]-6-hydroxy-hexylcarbamoyl}-2,2-diphenyl-ethyl)-amide (MX-254)

The title compound was obtained in 73% yield using (2S,5S)-2-amino-N-{5-[(4-amino-benzenesulfonyl)-isobutyl-amino]-6-hydroxy-hexyl}-3,3-diphenyl-propionamide (product of example 72) and picolinic acid with general procedure A but without the acidic workup.

LC-MS: 672.2 (M+H)$^+$, >98% pure.

Example 97

Preparation of (1S,5S)-Pyrazine-2-carboxylic Acid (1-{5-[(4-Amino-benzenesulfonyl)-isobutyl-amino]-6-hydroxy-hexylcarbamoyl}-2,2-diphenyl-ethyl)-amide (MX-255)

The title compound was obtained in 30% yield using (2S,5S)-2-amino-N-{5-[(4-amino-benzenesulfonyl)-isobutyl-amino]-6-hydroxy-hexyl}-3,3-diphenyl-propionamide (product of example 72) and pyrazine-2-carboxylic acid with general procedure A but without the acidic workup.

LC-MS: 673.2 (M+H)$^+$, >93% pure.

Example 98

Preparation of (1S,5S)-Pyrrole-2-carboxylic Acid (1-{5-[(4-Amino-benzenesulfonyl)-isobutyl-amino]-6-hydroxy-hexylcarbamoyl}-2,2-diphenyl-ethyl)-amide (MX-256)

The title compound was obtained in 70% yield using (2S,5S)-2-amino-N-{5-[(4-amino-benzenesulfonyl)-isobutyl-amino]-6-hydroxy-hexyl}-3,3-diphenyl-propionamide (product of example 72) and pyrrole-2-carboxylic acid with general procedure A but without the acidic workup.

LC-MS: 660.3 (M+H)$^+$, >98% pure.

Example 99

Preparation of (2S,5S)-N-{5-[(4-Amino-benzenesulfonyl)-isobutyl-amino]-6-hydroxy-hexyl}-3,3-diphenyl-2-(2-pyridin-3-yl-acetylamino)-propionamide (MX-257)

The title compound was obtained in 80% yield using (2S,5S)-2-amino-N-{5-[(4-amino-benzenesulfonyl)-isobutyl-amino]-6-hydroxy-hexyl}-3,3-diphenyl-propionamide (product of example 72) and pyridin-3-yl-acetic acid with general procedure A but without the acidic workup.

LC-MS: 686.3 (M+H)$^+$, >96% pure.

Example 100

Preparation of (1S,5S)-(1-{5-[(4-Amino-benzenesulfonyl)-isobutyl-amino]-6-hydroxy-hexylcarbamoyl}-2,2-diphenyl-ethyl)-carbamic Acid Pyridin-3-ylmethyl Ester (MX-267)

The title compound was obtained in 38% yield using (2S,5S)-2-amino-N-{5-[(4-amino-benzenesulfonyl)-isobutyl-amino]-6-hydroxy-hexyl}-3,3-diphenyl-propionamide (product of example 72) and pyridin-3-yl-methanol with general procedure G.

LC-MS: 702.2 (M+H)$^+$, >98% pure.

Example 101

Preparation of (1S,5S)-(1-{5-[(4-Amino-benzenesulfonyl)-isobutyl-amino]-6-hydroxy-hexylcarbamoyl}-2,2-diphenyl-ethyl)-carbamic Acid Pyridin-4-ylmethyl Ester (MX-270)

The title compound was obtained in 36% yield using (2S,5S)-2-amino-N-{5-[(4-amino-benzenesulfonyl)- isobutyl-amino]-6-hydroxy-hexyl}-3,3-diphenyl-propionamide (product of example 72) and pyridin-4-yl-methanol with general procedure G.

LC-MS: 702.2 (M+H)+, >98% pure.

Example 102

Preparation of (1S,5S)-N-(1-{5-[(4-Amino-benzenesulfonyl)-isobutyl-amino]-6-hydroxy-hexylcarbamoyl}-2,2-diphenyl-ethyl)-4-hydroxy-benzamide (MX-268)

The title compound was obtained in 55% yield using (2S,5S)-2-amino-N-{5-[(4-amino-benzenesulfonyl)-isobutyl-amino]-6-hydroxy-hexyl}-3,3-diphenyl-propionamide (product of example 72) and 4-hydroxybenzoic acid with general procedure A.

LC-MS: 687.2 (M+H)+, >98% pure.

Example 103

Preparation of (1S,5S)-N-(1-{5-[(4-Amino-benzenesulfonyl)-isobutyl-amino]-6-hydroxy-hexylcarbamoyl}-2,2-diphenyl-ethyl)-4-hydroxy-3-nitro-benzamide (MX-269)

The title compound was obtained in 55% yield using (2S,5S)-2-amino-N-{5-[(4-amino-benzenesulfonyl)-isobutyl-amino]-6-hydroxy-hexyl}-3,3-diphenyl-propionamide (product of example 72) and 4-hydroxy-3-nitro-benzoic acid with general procedure A.

LC-MS: 732.2 (M+H)+, >98% pure.

Example 104

Preparation of (1S,5S)-N-(1-{5-[(4-Amino-benzenesulfonyl)-isobutyl-amino]-6-hydroxy-hexylcarbamoyl}-2,2-diphenyl-ethyl)-2-hydroxy-benzamide (MX-271)

The title compound was obtained in 73% yield using (2S,5S)-2-amino-N-{5-[(4-amino-benzenesulfonyl)-isobutyl-amino]-6-hydroxy-hexyl}-3,3-diphenyl-propionamide (product of example 72) and salicylic acid with general procedure A.

LC-MS: 687.2 (M+H)+, >98% pure.

Example 105

Preparation of (1S,5S)-N-(1-{5-[(4-Amino-benzenesulfonyl)-isobutyl-amino]-6-hydroxy-hexylcarbamoyl}-2,2-diphenyl-ethyl)-3-hydroxy-benzamide (MX-272)

The title compound was obtained in 50% yield using (2S,5S)-2-amino-N-{5-[(4-amino-benzenesulfonyl)-isobutyl-amino]-6-hydroxy-hexyl}-3,3-diphenyl-propionamide (product of example 72) and 3-hydroxy-benzoic acid with general procedure A.

LC-MS: 687.2 (M+H)+, >98% pure.

Example 106

Preparation of (1S,5S)-N-(1-{5-[(4-Amino-benzenesulfonyl)-isobutyl-amino]-6-hydroxy-hexylcarbamoyl}-2,2-diphenyl-ethyl)-4-hydroxy-3-methoxy-benzamide (MX-273)

The title compound was obtained in 31% yield using (2S,5S)-2-amino-N-{5-[(4-amino-benzenesulfonyl)-isobutyl-amino]-6-hydroxy-hexyl}-3,3-diphenyl-propionamide (product of example 72) and 4-hydroxy-3-methoxy-benzoic acid with general procedure A.

LC-MS: 717.2 (M+H)+, >98% pure.

Example 107

Preparation of (1S,5S)-N-(1-{5-[(4-Amino-benzenesulfonyl)-isobutyl-amino]-6-hydroxy-hexylcarbamoyl}-2,2-diphenyl-ethyl)-3-hydroxy-4-nitro-benzamide (MX-274)

The title compound was obtained in 43% yield using (2S,5S)-2-amino-N-{5-[(4-amino-benzenesulfonyl)-isobutyl-amino]-6-hydroxy-hexyl}-3,3-diphenyl-propionamide (product of example 72) and 3-hydroxy-4-nitro-benzoic acid with general procedure A.

LC-MS: 732.2 (M+H)+, >96% pure.

Example 108

Preparation of (1S,5S)-3-Hydroxy-pyridine-2-carboxylic Acid-N-(1-{5-[(4-amino-benzenesulfonyl)-isobutyl-amino]-6-hydroxy-hexylcarbamoyl}-2,2-diphenyl-ethyl)-amide (MX-275)

The title compound was obtained in 15% yield using (2S,5S)-2-amino-N-{5-[(4-amino-benzenesulfonyl)-isobutyl-amino]-6-hydroxy-hexyl}-3,3-diphenyl-propionamide (product of example 72) and 3-hydroxy-picolinic acid with general procedure A.

LC-MS: 688.2 (M+H)+, >98% pure.

Example 109

Preparation of (1S,5S)-6-Amino-N-(1-{5-[(4-amino-benzenesulfonyl)-isobutyl-amino]-6-hydroxy-hexylcarbamoyl}-2,2-diphenyl-ethyl)-nicotinamide (MX-276)

The title compound was obtained in 33% yield using (2S,5S)-2-amino-N-{5-[(4-amino-benzenesulfonyl)-isobutyl-amino]-6-hydroxy-hexyl}-3,3-diphenyl-propionamide (product of example 72) and 6-amino-nicotinic acid with general procedure A.

LC-MS: 687.2 (M+H)+, >98% pure.

Example 110

Preparation of (1S,5S)-N-(1-{5-[(4-Amino-benzenesulfonyl)-isobutyl-amino]-6-hydroxy-hexylcarbamoyl}-2,2-diphenyl-ethyl)-6-hydroxy-nicotinamide (MX-277)

The title compound was obtained in 18% yield using (2S,5S)-2-amino-N-{5-[(4-amino-benzenesulfonyl)-isobutyl-amino]-6-hydroxy-hexyl}-3,3-diphenyl-propionamide (product of example 72) and 6-hydroxy-nicotinic acid with general procedure A.

LC-MS: 688.2 (M+H)+, >98% pure.

Example 111

Preparation of (1S,5S)-N-(1-{5-[(4-Amino-benzenesulfonyl)-isobutyl-amino]-6-hydroxy-hexylcarbamoyl}-2,2-diphenyl-ethyl)-2-methyl-nicotinamide (MX-278)

The title compound was obtained in 66% yield using (2S,5S)-2-amino-N-{5-[(4-amino-benzenesulfonyl)- isobutyl-amino]-6-hydroxy-hexyl}-3,3-diphenyl-propionamide (product of example 72) and 2-methyl-nicotinic acid with general procedure A.

LC-MS: 686.3 (M+H)$^+$, >98% pure.

Example 112

Preparation of (1S,5S)-N-(1-{5-[(4-Amino-benzenesulfonyl)-isobutyl-amino]-6-hydroxy-hexylcarbamoyl}-2,2-diphenyl-ethyl)-6-methyl-nicotinamide (MX-279)

The title compound was obtained in 74% yield using (2S,5S)-2-amino-N-{5-[(4-amino-benzenesulfonyl)-isobutyl-amino]-6-hydroxy-hexyl}-3,3-diphenyl-propionamide (product of example 72) and 6-methyl-nicotinic acid with general procedure A.

LC-MS: 686.3 (M+H)$^+$, >98% pure.

Example 113

Preparation of (2S,5S)-2-Amino-N-{5-[(4-amino-3-fluoro-benzenesulfonyl)-isobutyl-amino]-6-hydroxy-hexyl}-3-naphthalen-2-yl-propionamide (MX-260)

This title compound was prepared from the hydrolysis of (1S,5S)-(1-{5-[(4-amino-3-fluoro-benzenesulfonyl)-isobutyl-amino]-6-hydroxy-hexylcarbamoyl}-2-naphthalen-2-yl-ethyl)-carbamic acid tert-butyl ester (example 91) as described in example 49. The yield obtained was 65%.

LC-MS: 559.2 (M+H)$^+$, 90% pure.

Example 114

Preparation of (1S,5S)-3H-Imidazole-4-carboxylic Acid (1-{5-[(3-Amino-4-fluoro-benzenesulfonyl)-isobutyl-amino]-6-hydroxy-hexylcarbamoyl}-2-naphthalen-2-yl-ethyl)-amide (MX-261)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure E using 4-imidazolecarboxylic acid. The final product was obtained in 20% yield.

LC-MS: 653.2 (M+H)$^+$, >95% pure.

Example 115

Preparation of (1S,5S)Pyrrolidine-1-carboxylic Acid (1-{5-[(3-Amino-4-fluoro-benzenesulfonyl)-isobutyl-amino]-6-hydroxy-hexylcarbamoyl}-2-naphthalen-2-yl-ethyl)-amide (MX-263)

The title compound was prepared from (2S,5S)-2-amino-N-{5-[(3-amino-4-fluoro-benzenesulfonyl)-isobutyl-amino]-6-hydroxy-hexyl}-3-naphthalen-2-yl-propionamide (example 81) as described in general procedure D using 1-pyrrolidinecarbonyl chloride. The final product was obtained in 57% yield.

LC-MS: 656.2 (M+H)$^+$, >95% pure.

Example 116

Preparation of (1S,5S) (1-{5-[(4-Amino-3-fluoro-benzenesulfonyl)-isobutyl-amino]-6-hydroxy-hexylcarbamoyl}-2-naphthalen-2-yl-ethyl)-carbamic Acid Methyl Ester (MX-266)

The title compound was prepared from (2S,5S)-2-amino-N-{5-[(4-amino-3-fluoro-benzenesulfonyl)-isobutyl-amino]-6-hydroxy-hexyl}-3-naphthalen-2-yl-propionamide (product of example 113) using the same procedure used for the preparation of (2S)-2-methoxycarbonylamino-3-naphthalen-2-yl-propionic (example 28, step E). The final product was obtained in 61% yield.

LC-MS: 617.3 (M+H)$^+$, >95% pure.

Enzymatic Assay for Determining the Inhibition Constant (Ki) of Synthetic Compounds Targeting the HIV Protease This is a fluorometric assay based on the cleavage by protease of a substrate carrying a donor group (EDANS) and an acceptor group (DABCYL) on each side of the cleavage site, interacting together through fluorescence resonance energy transfer (FRET) as described by Matayoshi et al. (Science 247:954–954, 1990).

After calculation of Vo and Vi, the inhibition constant (Ki) of the compound is determined using the equation of Henderson:

$$\frac{Vo}{Vi} = 1 + \frac{[I]}{Ki_{app}} \text{ Where } Ki = \frac{Ki_{app}}{1 + \frac{[S]}{Km}}$$

where Vo=the enzyme's initial velocity

Vi=the enzyme velocity in the presence of the inhibitory compound,

[I]=inhibitor concentration, [S]=substrate concentration,

Km=Michaelis-Menten constant and Ki$_{app}$=apparent Ki

Graphs are traced and the Ki determined using GraphPad Prism software v. 3.0.

Anti-viral and Cytotoxicity Assays In Vitro

To evaluate the EC$_{50}$ of our compounds, various drug concentrations are incubated with the infected cell for six days and then the metabolic activity of the cells is monitored by the MTT assay. (See A. J. Japour et al, Antimicrobial Agents and Chemotherapy, 37, 1095–1101, 1993 and R. Pauwels et al. Journal of Virological Methods, 20, 309–321, 1988)

We use the laboratory viral strain NL4.3 as wild type virus and the cell line used is MT-4 which is a T-cell line highly sensitive to HIV-1. We also use some WT clinical strains. To address the resistance issue we assay the inhibitors with NL4.3 mutants which are designed to be resistant to specific commercially,available inhibitors The same MTT assay is used to evaluate the CCIC$_{50}$ (cell culture IC$_{50}$) of our compounds except that the virus is omitted.

The compounds listed in Table 1 were prepared by following scheme 1, 2, 3 or 4; and more particularly as described in each example listed above. The numbers of the compounds listed in Table 1 (Ex. No.) corresponds to the example numbers presented above. The activities of the compounds are also listed in the same tables demonstrating their potential usefulness. The CCIC$_{50}$ are not shown in the table but were found to be in the range of 25 to 35 μM for each of the HIV protease inhibitors of this invention. Thus, in Table 1 are shown compounds of formula I wherein n, X, Y, R$_1$, R$_2$, and R$_3$ are as presented in Table 1. Ki and EC$_{50}$ results for compounds of formula I are also presented in Table 1 illustrating their potential usefulness.

TABLE 1

Anti-protease activity of the new HIV aspartyl protease inhibitors in accordance with this invention

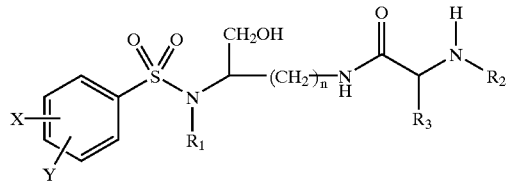

I

| Ex. No. | X/Y | R$_1$ | R$_2$ | R$_3$ | n | Ki* | EC$_{50}$* | D, L, DL R, S, RS |
|---|---|---|---|---|---|---|---|---|
| 1 | 4-NH$_2$/H | i-C$_4$H$_9$ | CH$_3$O—CO | Naphthyl-2-CH$_2$ | 3 | 7.3 | 1473 | S, S |
| 2 | 4-NH$_2$/H | i-C$_4$H$_9$ | CH$_3$O—CO | Naphthyl-1-CH$_2$ | 3 | 2.8 | 674 | S, S |
| 3 | 4-NH$_2$/H | i-C$_4$H$_9$ | CH$_3$O—CO | Biphenyl-2-CH$_2$ | 3 | 2.4 | 64 | S, RS |
| 4 | 4-NH$_2$/H | i-C$_4$H$_9$ | 4-Morpholine-CO | Naphthyl-1-CH$_2$ | 3 | 1.4 | 728 | S, S |
| 5 | 4-NH$_2$/H | i-C$_4$H$_9$ | 4-CH$_3$OC$_6$H$_4$CH$_2$CO | Naphthyl-1-CH$_2$ | 3 | 11 | | S, S |
| 6 | 4-NH$_2$/H | i-C$_4$H$_9$ | CH$_3$O—CO | 4'-CH$_3$O-biphenyl-2-CH$_2$ | 3 | 13 | | S, S |
| 7 | 4-NH$_2$/H | i2C$_4$H$_9$ | CF$_3$CH$_2$O—CO | Naphthyl-1-CH$_2$ | 3 | 4 | | S, S |
| 8 | 4-NH$_2$/H | i-C$_4$H$_9$ | H | Naphthyl-1-CH$_2$ | 3 | 1.6 | | S, S |
| 9 | 4-NH$_2$/H | i-C$_4$H$_9$ | 4-Morpholine-CO | (C$_6$H$_5$)$_2$CH | 3 | 4.2 | 1300 | S, S |
| 10 | 4-NH$_2$/H | i-C$_4$H$_9$ | CH$_3$O—CO | (C$_6$H$_5$)$_2$CH | 3 | 5.0 | 514 | S, S |
| 11 | 4-NH$_2$/H | i-C$_4$H$_9$ | CH$_3$O$_2$C-CO | Naphthyl-1-CH$_2$ | 3 | 5.0 | 64000 | S, S |
| 12 | 4-NH$_2$/H | i-C$_4$H$_9$ | CF$_3$CH$_2$CO | Naphthyl-1-CH$_2$ | 3 | 1.6 | 747 | S, S |
| 13 | 4-NH$_2$/H | i-C$_4$H$_9$ | C$_6$H$_{11}$CO | Naphthyl-1-CH$_2$ | 3 | 2.3 | | S, S |
| 14 | 4-NH$_2$/H | i-C$_4$H$_9$ | H | Biphenyl-2-CH$_2$ | 3 | 7.1 | | S, S |
| 15 | 4-NH$_2$/H | i-C$_4$H$_9$ | CH$_3$O$_2$C-CH$_2$ | Naphthyl-1-CH$_2$ | 3 | 4.2 | | S, S |
| 16 | 4-NH$_2$/H | i-C$_4$H$_9$ | t-ButylO—CO (Boc) | (C$_6$H$_5$)$_2$CH | 3 | 9.3 | | S, S |
| 17 | 4-NH$_2$/H | i-C$_4$H$_9$ | CH$_3$OCH$_2$CH$_2$O—CO | Naphthyl-1-CH$_2$ | 3 | 3.7 | | S, S |
| 18 | 4-NH$_2$/H | i-C$_4$H$_9$ | CH$_3$CH$_2$O—CO | Naphthyl-1-CH$_2$ | 3 | 3.9 | | S, S |
| 19 | 4-NH$_2$/H | i-C$_4$H$_9$ | CH$_3$OCH$_2$—CO | Naphthyl-1-CH$_2$ | 3 | 2.6 | | S, S |
| 20 | 4-NH$_2$/H | i-C$_4$H$_9$ | CH$_3$CH$_2$CH$_2$CH$_2$ | Naphthyl-1-CH$_2$ | 3 | 4.4 | | S, S |
| 21 | 4-NH$_2$/H | i-C$_4$H$_9$ | AcOCH$_2$CH$_2$ | Naphthyl-1-CH$_2$ | 3 | 3.9 | | S, S |
| 22 | 4-NH$_2$/H | i-C$_4$H$_9$ | CH$_3$CH$_2$CH$_2$ | Naphthyl-1-CH$_2$ | 3 | 2.5 | | S, S |
| 23 | 4-NH$_2$/H | i-C$_4$H$_9$ | Cyclopentyl-CO | Naphthyl-1-CH$_2$ | 3 | 2.0 | | S, S |
| 24 | 4-NH$_2$/H | i-C$_4$H$_9$ | H | (C$_6$H$_5$)$_2$CH | 3 | 7.5 | | S, S |
| 25 | 4-NH$_2$/H | i-C$_4$H$_9$ | i-C$_4$H$_9$ | Naphthyl-1-CH$_2$ | 3 | 3.7 | | S, S |
| 26 | 4-NH$_2$/H | i-C$_4$H$_9$ | CH$_3$CH$_2$ | Naphthyl-1-CH$_2$ | 3 | 3.0 | | S, S |
| 27 | 4-NH$_2$/H | i-C$_4$H$_9$ | HO$_2$C-CH$_2$ | Naphthyl-1-CH$_2$ | 3 | 2.5 | | S, S |
| 28 | 4-NH$_2$/H | i-C$_4$H$_9$ | CH$_3$O—CO | Naphthyl-1-CH$_2$ | 4 | 1.2 | | S, S |
| 29 | 4-NH$_2$/H | i-C$_4$H$_9$ | CH$_3$O—CO | Naphthyl-2-CH$_2$ | 4 | 1.2 | | S, S |
| 30 | 4-NH$_2$/H | i-C$_4$H$_9$ | CH$_3$O—CO | Biphenyl-2-CH$_2$ | 4 | 1.4 | 344 | S, RS |
| 31 | 4-NH$_2$/H | i-C$_4$H$_9$ | CH$_3$O—CO | 4'-CH$_3$O-biphenyl-2-CH$_2$ | 4 | 0.667 | 118 | S, S |
| 32 | 4-NH$_2$/H | i-C$_4$H$_9$ | 4-Morpholine-CO | Naphthyl-1-CH$_2$ | 4 | 0.782 | 30 | S, S |
| 33 | 4-NH$_2$/H | i-C$_4$H$_9$ | 4-Morpholine-CO | Naphthyl-2-CH$_2$ | 4 | 0.800 | 92 | S, S |
| 34 | 4-NH$_2$/H | i-C$_4$H$_9$ | CH$_3$O—CO | (C$_6$H$_5$)$_2$CH | 4 | 0.500 | 12 | S, S |
| 35 | 4-NH$_2$/H | i-C$_4$H$_9$ | 4-Morpholine-CO | Naphthyl-2-CH$_2$ | 4 | 1.3 | 275 | S, S |
| 36 | 4-NH$_2$/H | i-C$_4$H$_9$ | CH$_3$O—CO | 4'-CH$_3$O-biphenyl-2-CH$_2$ | 4 | 3.2 | 2185 | S, S |
| 37 | 4-NH$_2$/H | i-C$_4$H$_9$ | 3-Tetrahydrofuranyl-CO | Naphthyl-2-CH$_2$ | 4 | 2.7 | 325 | S, S |
| 38 | 4-NH$_2$/H | i-C$_4$H$_9$ | 4-Morpholine-CO | 4'-CH$_3$O-biphenyl-2-CH$_2$ | 4 | 0.533 | 93 | S, S |
| 39 | 4-NH$_2$/H | i-C$_4$H$_9$ | CH$_3$O—CO | Biphenyl-2-CH$_2$ | 4 | 0.521 | 200 | S, S |
| 40 | 4-NH$_2$/H | i-C$_4$H$_9$ | 4-Morpholine-CO | (C$_6$H$_5$)$_2$CH | 4 | 0.512 | 78 | S, S |
| 41 | 4-NH$_2$/H | i-C$_4$H$_9$ | (CH$_3$)$_2$N—CO | Naphthyl-2-CH$_2$ | 4 | 1.1 | 79 | S, S |
| 42 | 4-NH$_2$/H | i-C$_4$H$_9$ | C$_6$H$_{11}$CO | Naphthyl-2-CH$_2$ | 4 | 1.2 | | S, S |
| 43 | 4-NH$_2$/H | i-C$_4$H$_9$ | 4-Morpholine-CO | Biphenyl-2-CH$_2$ | 4 | 0.598 | 697 | S, S |
| 44 | 3-Cl/4-NH$_2$ | i-C$_4$H$_9$ | 4-Morpholine-CO | Naphthyl-1-CH$_2$ | 4 | 0.904 | 134 | S, S |
| 45 | 4-CH$_3$O/H | i-C$_4$H$_9$ | 4-Morpholine-CO | Naphthyl-1-CH$_2$ | 4 | 1.5 | 597 | S, S |
| 46 | 4-NH$_2$/H | i-C$_4$H$_9$ | t-Butyl-CO | Naphthyl-2-CH$_2$ | 4 | 0.809 | 167 | S, S |
| 47 | 4-NH$_2$/H | i-C$_4$H$_9$ | Cyclopropyl-CO | Naphthyl-2-CH$_2$ | 4 | 1.4 | 323 | S, S |
| 48 | 4-NH$_2$/H | i-C$_4$H$_9$ | Ac | Naphthyl-2-CH$_2$ | 4 | 3.6 | 948 | S, S |
| 49 | 4-NH$_2$/H | i-C$_4$H$_9$ | H | Naphthyl-2-CH$_2$ | 4 | 1.3 | | S, S |
| 50 | 3-Cl/4-NH$_2$ | i-C$_9$H$_9$ | CH$_3$O—CO | (C$_6$H$_5$)$_2$CH | 4 | 0.776 | 95 | S, S |
| 51 | 3-Cl/4-NH$_2$ | i-C$_4$H$_9$ | 4-Morpholine-CO | Naphthyl-2-CH$_2$ | 4 | 0.800 | 194 | S, S |
| 52 | 4-NH$_2$/H | i-C$_4$H$_9$ | CH$_3$O—CO | 3'-F-biphenyl-2-CH$_2$ | 4 | 0.700 | 152 | S, S |
| 53 | 4-F/3-NH$_2$ | i-C$_4$H$_9$ | 4-Morpholine-CO | Naphthyl-1-CH$_2$ | 4 | 0.626 | 40 | S, S |
| 54 | 4-NH$_2$/H | i-C$_4$H$_9$ | 3-Pyridyl-CO | Naphthyl-2-CH$_2$ | 4 | 1.4 | 146 | S, S |
| 55 | 4-NH$_2$/H | i-C$_4$H$_9$ | 4-Pyridyl-CO | Naphthyl-2-CH$_2$ | 4 | 1.3 | 110 | S, S |
| 56 | 4-F/3-NH$_2$ | i-C$_4$H$_9$ | CH$_3$O—CO | 3'-F-biphenyl-2-CH$_2$ | 4 | 1.3 | 300 | S, S |
| 57 | 3-Cl/4-NH$_2$ | i-C$_4$H$_9$ | CH$_3$O—CO | 3'-F-biphenyl-2-CH$_2$ | 4 | 1.7 | | S, S |
| 58 | 4-F/3-NH$_2$ | i-C$_4$H$_9$ | CH$_3$O—CO | (C$_6$H$_5$)$_2$CH | 4 | 0.650 | 25 | S, S |

TABLE 1-continued

Anti-protease activity of the new HIV aspartyl protease inhibitors in accordance with this invention

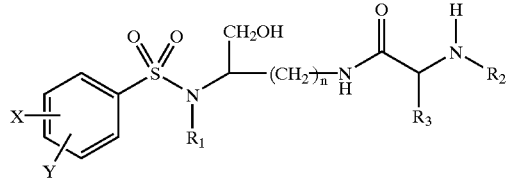

| Ex. No. | X/Y | $R_1$ | $R_2$ | $R_3$ | n | Ki* | EC$_{50}$* | D, L, DL R, S, RS |
|---|---|---|---|---|---|---|---|---|
| 59 | 4-NH$_2$/H | i-C$_4$H$_9$ | t-ButylO—CO (Boc) | Biphenyl-4-CH$_2$ | 4 | 6.0 | | S, S |
| 60 | 4-NH$_2$/H | i-C$_4$H$_9$ | Cyclopentyl-CO | Naphthyl-2-CH$_2$ | 4 | 1.9 | | S, S |
| 61 | 4-NH$_2$/H | i-C$_4$H$_9$ | CF$_3$CH$_2$CO | Naphthyl-2-CH$_2$ | 4 | 1.6 | 161 | S, S |
| 62 | 4-NH$_2$/H | i-C$_4$H$_9$ | Pyrazine-CO | Naphthyl-2-CH$_2$ | 4 | 2.1 | 361 | S, S |
| 63 | 4-NH$_2$/H | i-C$_4$H$_9$ | i-C$_4$H$_9$ | Naphthyl-2-CH$_2$ | 4 | 3.9 | | S, S |
| 64 | 4-NH$_2$/H | i-C$_4$H$_9$ | CH$_3$CH$_2$CH$_2$ | Naphthyl-2-CH$_2$ | 4 | 4.6 | | S, S |
| 65 | 4-NH$_2$/H | i-C$_4$H$_9$ | CH$_3$CH$_2$ | Naphthyl-2-CH$_2$ | 4 | 6.2 | | S, S |
| 66 | 3,4-methylenedioxy | i-C$_4$H$_9$ | 4-Morpholine-CO | Naphthyl-1-CH$_2$ | 4 | 1.1 | 409 | S, S |
| 67 | 3,4-methylenedioxy | i-C$_4$H$_9$ | CH$_3$O—CO | (C$_6$H$_5$)$_2$CH | 4 | 1.6 | 146 | S, S |
| 68 | 4-NH$_2$/H | i-C$_4$H$_9$ | CH$_3$CH$_2$CH$_2$CH$_2$ | Naphthyl-2-CH$_2$ | 4 | 5.8 | | S, S |
| 69 | 4-NH$_2$/H | i-C$_4$H$_9$ | (CH$_3$)$_3$CCH$_2$ | Naphthyl-2-CH$_2$ | 4 | 22 | | S, S |
| 70 | 4-NH$_2$/H | i-C$_4$H$_9$ | 2-Picolyl | Naphthyl-2-CH$_2$ | 4 | 4.9 | | S, S |
| 71 | 4-NH$_2$/H | i-C$_4$H$_9$ | Ac | (C$_6$H$_5$)$_2$CH | 4 | 1.5 | 66 | S, S |
| 72 | 4-NH$_2$/H | i-C$_4$H$_9$ | H | (C$_6$H$_5$)$_2$CH | 4 | 7.5 | | S, S |
| 73 | 4-NH$_2$/H | i-C$_4$H$_9$ | 3-Pyridyl-CO | (C$_6$H$_5$)$_2$CH | 4 | 0.681 | 39 | S, S |
| 74 | 4-NH$_2$/H | i-C$_4$H$_9$ | 4-Pyridyl-CO | (C$_6$H$_5$)$_2$CH | 4 | 0.647 | 32 | S, S |
| 75 | 4-NH$_2$/H | i-C$_4$H$_9$ | Cyclopropyl-CO | (C$_6$H$_5$)$_2$CH | 4 | <3.8 | 25 | S, S |
| 76 | 4-NH$_2$/H | i-C$_4$H$_9$ | Cyclohexyl-CO | (C$_6$H$_5$)$_2$CH | 4 | <3.8 | 93 | S, S |
| 77 | 4-NH$_2$/H | i-C$_4$H$_9$ | 3-Tetrahydrofuranyl-CO | (C$_6$H$_5$)$_2$CH | 4 | 0.581 | 68 | S, S |
| 78 | H/4-F | i-C$_4$H$_9$ | CH$_3$O—CO | (C$_6$H$_5$)$_2$CH | 4 | <3.8 | 94 | S, S |
| 79 | 4-CN/H | i-C$_4$H$_9$ | CH$_3$O—CO | (C$_6$H$_5$)$_2$CH | 4 | <3.8 | 65 | S, S |
| 80 | 2-F/4-F | i-C$_4$H$_9$ | CH$_3$O—CO | (C$_6$H$_5$)$_2$CH | 4 | <3.8 | 48 | S, S |
| 81 | 3-NH$_2$/4-F | i-C$_4$H$_9$ | H | Naphthyl-2-CH$_2$ | 4 | <3.8 | | S, S |
| 82 | 3-NH$_2$/4-F | i-C$_4$H$_9$ | CH$_3$O—CO | Naphthyl-2-CH$_2$ | 4 | <3.8 | | S, S |
| 83 | 3-NH$_2$/4-F | i-C$_4$H$_9$ | 3-Pyridyl-CO | Naphthyl-2-CH$_2$ | 4 | <3.8 | | S, S |
| 84 | 3-NH$_2$/4-F | i-C$_4$H$_9$ | 4-Pyridyl-CO | Naphthyl-2-CH$_2$ | 4 | <3.8 | | S, S |
| 85 | 3-NH$_2$/4-F | i-C$_4$H$_9$ | 3-Tetrahydrofuranyl-CO | Naphthyl-2-CH$_2$ | 4 | <3.8 | | S, S |
| 86 | 3-NH$_2$/4-F | i-C$_4$H$_9$ | (CH$_3$)$_2$N—CO | Naphthyl-2-CH$_2$ | 4 | <3.8 | | S, S |
| 87 | 3-NH$_2$/4-F | i-C$_4$H$_9$ | Cyclopropyl-CO | Naphthyl-2-CH$_2$ | 4 | <3.8 | | S, S |
| 88 | 3-NH$_2$/4-F | i-C$_4$H$_9$ | Cyclohexyl-CO | Naphthyl-2-CH$_2$ | 4 | <3.8 | | S, S |
| 89 | 3-NH$_2$/4-F | i-C$_4$H$_9$ | Ac | Naphthyl-2-CH$_2$ | 4 | <3.8 | | S, S |
| 90 | 3-NH$_2$/4-F | i-C$_4$H$_9$ | t-ButylO—CO (Boc) | Naphthyl-2-CH$_2$ | 4 | 4.0 | | S, S |
| 91 | 4-NH$_2$/3-F | i-C$_4$H$_9$ | t-ButylO—CO (Boc) | Naphthyl-2-CH$_2$ | 4 | <3.8 | | S, S |
| 92 | 3-NH$_2$/4-F | i-C$_4$H$_9$ | t-ButylO—CO (Boc) | (C$_6$H$_5$)$_2$CH | 4 | | | S, S |
| 93 | 4-NH$_2$/3-F | i-C$_4$H$_9$ | t-ButylO—CO (Boc) | (C$_6$H$_5$)$_2$CH | 4 | | | S, S |
| 94 | 4-NH$_2$/H | i-C$_4$H$_9$ | (CH$_3$)$_2$N—CO | (C$_6$H$_5$)$_2$CH | 4 | <3.8 | | S, S |
| 95 | 4-NH$_2$/H | i-C$_4$H$_9$ | 2-PicolylO—CO | (C$_6$H$_5$)$_2$CH | 4 | <3.8 | | S, S |
| 96 | 4-NH$_2$/H | i-C$_4$H$_9$ | 2-Pyridyl-CO | (C$_6$H$_5$)$_2$CH | 4 | <3.8 | | S, S |
| 97 | 4-NH$_2$/H | i-C$_4$H$_9$ | Pyrazine-CO | (C$_6$H$_5$)$_2$CH | 4 | <3.8 | | S, S |
| 98 | 4-NH$_2$/H | i-C$_4$H$_9$ | Pyrrole-2-CO | (C$_6$H$_5$)$_2$CH | 4 | <3.8 | | S, S |
| 99 | 4-NH$_2$/H | i-C$_4$H$_9$ | 3-Picolyl-CO | (C$_6$H$_5$)$_2$CH | 4 | <3.8 | | S, S |
| 100 | 4-NH$_2$/H | i-C$_4$H$_9$ | 3-PicolylO—CO | (C$_6$H$_5$)$_2$CH | 4 | <3.8 | | S, S |
| 101 | 4-NH$_2$/H | i-C$_4$H$_9$ | 4-PicolylO—CO | (C$_6$H$_5$)$_2$CH | 4 | <3.8 | | S, S |
| 102 | 4-NH$_2$/H | i-C$_4$H$_9$ | 4-HO-Phenyl-CO | (C$_6$H$_5$)$_2$CH | 4 | <3.8 | | S, S |
| 103 | 4-NH$_2$/H | i-C$_4$H$_9$ | 4-HO-3-NO$_2$-Phenyl-CO | (C$_6$H$_5$)$_2$CH | 4 | <3.8 | | S, S |
| 104 | 4-NH$_2$/H | i-C$_4$H$_9$ | 2-HO-Phenyl-CO | (C$_6$H$_5$)$_2$CH | 4 | <3.8 | | S, S |
| 105 | 4-NH$_2$/H | i-C$_4$H$_9$ | 3-HO-Phenyl-CO | (C$_6$H$_5$)$_2$CH | 4 | <3.8 | | S, S |
| 106 | 4-NH$_2$/H | i-C$_4$H$_9$ | 4-HO-3-CH$_3$O-Phenyl-CO | (C$_6$H$_5$)$_2$CH | 4 | <3.8 | | S, S |
| 107 | 4-NH$_2$/H | i-C$_4$H$_9$ | 3-HO-4-NO$_2$-Phenyl-CO | (C$_6$H$_5$)$_2$CH | 4 | <3.8 | | S, S |
| 108 | 4-NH$_2$/H | i-C$_4$H$_9$ | 3-HO-2-Pyridyl-CO | (C$_6$H$_5$)$_2$CH | 4 | <3.8 | | S, S |
| 109 | 4-NH$_2$/H | i-C$_4$H$_9$ | 6-H$_2$N-3-Pyridyl-CO | (C$_6$H$_5$)$_2$CH | 4 | <3.8 | | S, S |
| 110 | 4-NH$_2$/H | i-C$_4$H$_9$ | 6-HO-3-Pyridyl-CO | (C$_6$H$_5$)$_2$CH | 4 | <3.8 | | S, S |
| 111 | 4-NH$_2$/H | i-C$_4$H$_9$ | 2-CH$_3$-3-Pyridyl-CO | (C$_6$H$_5$)$_2$CH | 4 | <3.8 | | S, S |
| 112 | 4-NH$_2$/H | i-C$_4$H$_9$ | 6-CH$_3$-3-Pyridyl-CO | (C$_6$H$_5$)$_2$CH | 4 | <3.8 | | S, S |
| 113 | 4-NH$_2$/3-F | i-C$_4$H$_9$ | H | Naphthyl-2-CH$_2$ | 4 | <3.8 | | S, S |
| 114 | 3-NH$_2$/4-F | i-C$_4$H$_9$ | 3H-Imidazole-4-CO | Naphthyl-2-CH$_2$ | 4 | <3.8 | | S, S |
| 115 | 3-NH$_2$/4-F | i-C$_4$H$_9$ | Pyrrolidine-CO | Naphthyl-2-CH$_2$ | 4 | <3.8 | | S, S |
| 116 | 4-NH$_2$/3-F | i-C$_4$H$_9$ | CH$_3$O—CO | Naphthyl-2-CH$_2$ | 4 | <3.8 | | S, S |

*nM

We claim:
1. A compound of formula I

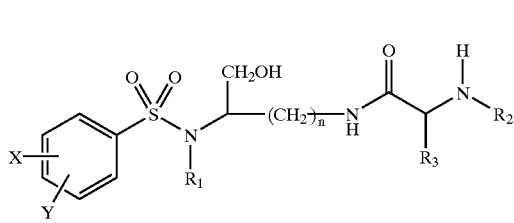

and when the compound of formula I comprises an amino group, pharmaceutically acceptable ammonium salts thereof, wherein n is 3 or 4, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein $R_1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein $R_2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

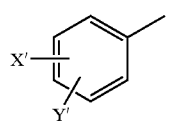

a picolyl group selected from the group consisting of

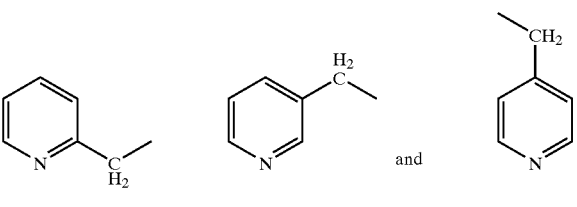

a picolyloxy group selected from the group consisting of

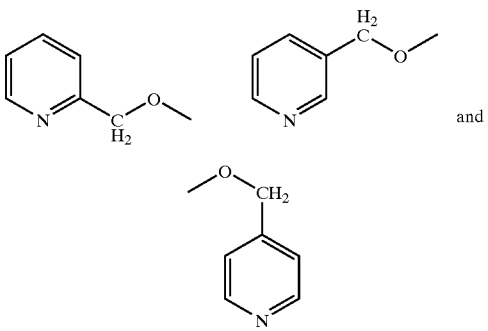

a substituted pyridyl group selected from the group consisting of

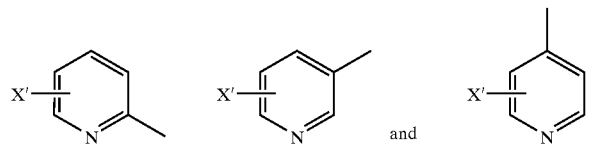

a group selected from the group consisting of

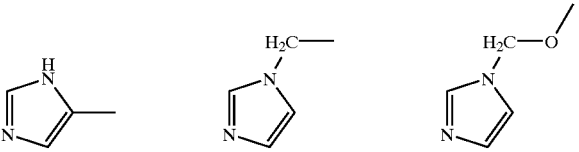

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R_4$ and $R_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein $R_3$ is selected from the group consisting of a diphenylmethyl group of formula IV

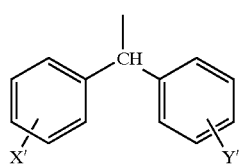

a naphthyl-1-CH₂— group of formula V

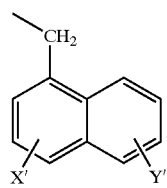

a naphthyl-2-CH₂— group of formula VI

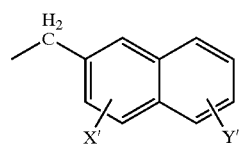

a biphenylmethyl group of formula VII

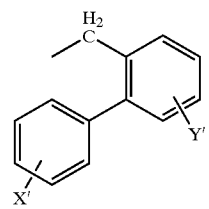

and an anthryl-9-CH₂— group of formula VIII

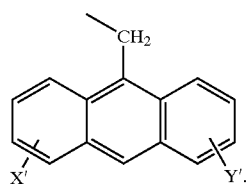

2. A compound of formula II,

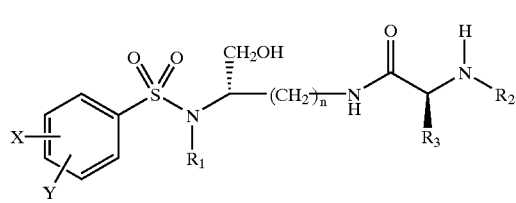

and when the compound of formula II comprises an amino group, pharmaceutically acceptable ammonium salts thereof, wherein n is 3 or 4, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —CF₃, —OCF₃, —CN, —NO₂, —NR₄R₅, —NHCOR₄, —OR₄, —SR₄, —COOR₄, —COR₄, and —CH₂OH or X and Y together together define an alkylenedioxy group selected from the group consisting of a methylenedioxy group of formula —OCH₂O— and an ethylenedioxy group of formula —OCH₂CH₂O—, wherein R₁ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, wherein R₂ is selected from the group consisting of H, a straight alkyl group of 1 to 6 carbon atoms, a branched alkyl group of 3 to 6 carbon atoms, a cycloalkyl group of 3 to 6 carbon atoms, and a group of formula R₂ₐ—CO—, R₂ₐ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —CH₂OH, —CF₃, —CH₂CF₃, —CH₂CH₂CF₃, pyrrolidinyl, piperidinyl, 4-morpholinyl, CH₃O₂C—, CH₃O₂CCH₂—, Acetyl-OCH₂CH₂—, HO₂CCH₂—, 3-hydroxyphenyl, 4-hydroxyphenyl, 4-CH₃OC₆H₄CH₂—, CH₃NH—, (CH₃)₂N—, (CH₃CH₂)₂N—, (CH₃CH₂CH₂)₂N—, HOCH₂CH₂NH—, CH₃OCH₂O—, CH₃OCH₂CH₂O—, C₆H₅CH₂O—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula

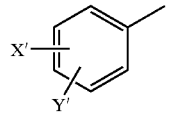

a picolyl group selected from the group consisting of

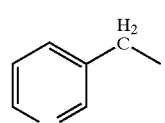 and 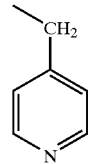

a picolyloxy group selected from the group consisting of

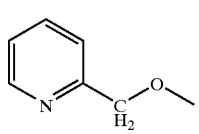 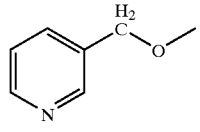 and

-continued

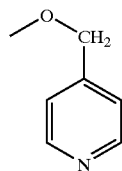

a substituted pyridyl group selected from the group consisting of

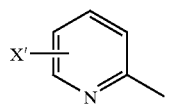 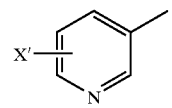 and 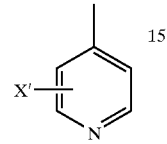

a group selected from the group consisting of

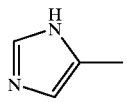 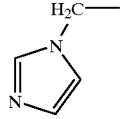 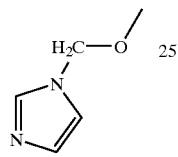

wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, wherein $R_4$ and $R_5$, the same or different, are selected from the group consisting of H, a straight alkyl group of 1 to 6 carbon atoms, a branched alkyl group of 3 to 6 carbon atoms, and a cycloalkyl group of 3 to 6 carbon atoms, wherein $R_3$ is selected from the group consisting of a diphenylmethyl group of formula IV

IV

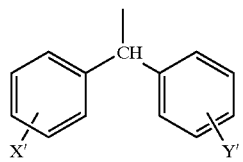

a naphthyl-1-$CH_2$— group of formula V

V

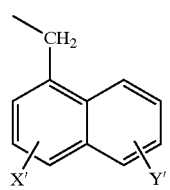

a naphthyl-2-$CH_2$— group of formula VI

VI

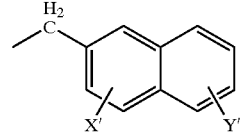

a biphenylmethyl group of formula VII

VII

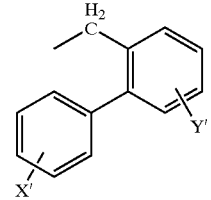

and an anthryl-9-$CH_2$— group of formula VIII

VIII

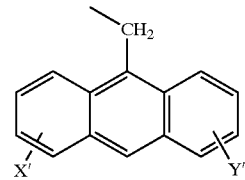

3. A compound as defined in claim 2, wherein $R_1$ is iso-butyl and n is 3.

4. A compound as defined in claim 2, wherein $R_1$ is iso-butyl and n is 4.

5. A compound as defined in claim 3, wherein $R_2$ is selected from the group consisting of $CH_3O$—CO, $(CH_3)_2N$—CO, 3-pyridyl-CO, 4-pyridyl-CO and 4-morpholinyl-CO.

6. A compound as defined in claim 4, wherein $R_2$ is selected from the group consisting of $CH_3O$—CO, $(CH_3)_2N$—CO, 3-pyridyl-CO, 4-pyridyl-CO and 4-morpholinyl-CO.

7. A compound as defined in claim 5, wherein, X is 4-$NH_2$ and Y is H.

8. A compound as defined in claim 6, wherein, X is 4-$NH_2$ and Y is H.

9. A compound as defined in claim 5, wherein, X is 4-F and Y is 3-$NH_2$.

10. A compound as defined in claim 6, wherein, X is 4-F and Y is 3-$NH_2$.

11. A compound as defined in claim 7, wherein $R_3$ is selected from the group consisting of a diphenylmethyl group of formula IV, a naphthyl-1-$CH_2$— group of formula V, a naphthyl-2-$CH_2$— group of formula VI, a biphenylmethyl group of formula VII and an anthryl-9-$CH_2$— group of formula VIII.

12. A compound as defined in claim 11, wherein $R_3$ is selected from the group consisting of a diphenylmethyl group of formula IV, a naphthyl-1-$CH_2$— group of formula V, a naphthyl-2-$CH_2$— group of formula VI, and a biphenylmethyl group of formula VII.

13. A compound as defined in claim 12, wherein X' and Y' is H.

14. A compound as defined in claim 8, wherein $R_3$ is selected from the group consisting of a diphenylmethyl group of formula IV, a naphthyl-1-$CH_2$— group of formula V, a naphthyl-2-$CH_2$— group of formula VI, a biphenylmethyl group of formula VII and an anthryl-9-$CH_2$— group of formula VIII.

15. A compound as defined in claim 14, wherein $R_3$ is selected from the group consisting of a diphenylmethyl group of formula IV, a naphthyl-1-$CH_2$— group of formula V, a naphthyl-2-$CH_2$— group of formula VI, and a biphenylmethyl group of formula VII.

16. A compound as defined in claim 15, wherein X' and Y' is H.

17. A compound as defined in claim 9, wherein $R_3$ is selected from the group consisting of a diphenylmethyl group of formula IV, a naphthyl-1-$CH_2$— group of formula V, a naphthyl-2-$CH_2$— group of formula VI, a biphenylmethyl group of formula VII and an anthryl-9-$CH_2$— group of formula VIII.

18. A compound as defined in claim 17, wherein $R_3$ is selected from the group consisting of a diphenylmethyl group of formula IV, a naphthyl-1-$CH_2$— group of formula V, a naphthyl-2-$CH_2$— group of formula VI, and a biphenylmethyl group of formula VII.

19. A compound as defined in claim 18, wherein X' and Y' is H.

20. A compound as defined in claim 10, wherein $R_3$ is selected from the group consisting of a diphenylmethyl group of formula IV, a naphthyl-1-$CH_2$— group of formula V, a naphthyl-2-$CH_2$— group of formula VI, a biphenylmethyl group of formula VII and an anthryl-9-$CH_2$— group of formula VIII.

21. A compound as defined in claim 20, wherein $R_3$ is selected from the group consisting of a diphenylmethyl group of formula IV, a naphthyl-1-$CH_2$— group of formula V, a naphthyl-2-$CH_2$— group of formula VI, and a biphenylmethyl group of formula VII.

22. A compound as defined in claim 21, wherein X' and Y' is H.

23. A compound of formula IIa

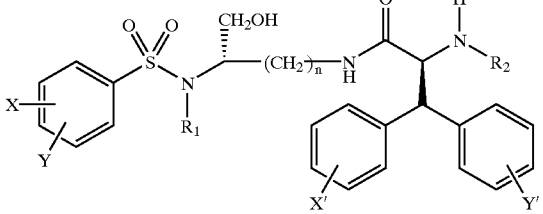

IIa and when the compound of formula IIa comprises an amino group, pharmaceutically acceptable ammonium salts thereof, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, and wherein n, $R_1$, $R_2$, $R_4$, and $R_5$ are as defined in claim 1.

24. A compound as defined in claim 23, wherein $R_1$ is iso-butyl.

25. A compound as defined in claim 24, wherein n is 4.

26. A compound as defined in claim 25, wherein $R_2$ is selected from the group consisting of $CH_3O$—CO, $(CH_3)_2$N—CO, 3-pyridyl-CO, 4-pyridyl-CO and 4-morpholine-CO.

27. A compound as defined in claim 26, wherein, X is 4-$NH_2$, Y is H, X' is H and Y' is H.

28. A compound as defined in claim 26, wherein, X is 3-$NH_2$, Y is 4-F, X' is H and Y' is H.

29. A compound as defined in claim 26, wherein, X is 4-$NH_2$, Y is 3-F, X' is H and Y' is H.

30. A compound as defined in claim 25, wherein X is 4-$NH_2$, Y is H, X' is H, Y' is H and $R_2$ is $CH_3O$—CO.

31. A compound as defined in claim 25, wherein X is 4-F, Y is 3-$NH_2$, X' is H, Y' is H and $R_2$ is $CH_3O$—CO.

32. A compound as defined in claim 25, wherein X is 4-$NH_2$, Y is H, X' is H, Y' is H and $R_2$ is cyclopropyl-CO.

33. A compound as defined in claim 25, wherein X is 4-$NH_2$, Y is H, X' is H, Y' is H and $R_2$ is $(CH_3)_2$N—CO.

34. A compound as defined in claim 25, wherein X is 4-$NH_2$, Y is H, X' is H, Y' is H and $R_2$ is 3-pyridyl-CO.

35. A compound as defined in claim 25, wherein X is 4-$NH_2$, Y is H, X' is H, Y' is H and $R_2$ is 4-pyridyl-CO.

36. A compound as defined in claim 25, wherein X is 4-$NH_2$, Y is H, X' is H, Y' is H and $R_2$ is 2-picolylO—CO.

37. A compound of formula IIb

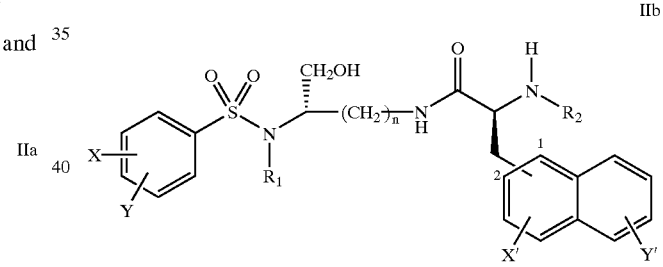

IIb and when the compound of formula IIb comprises an amino group, pharmaceutically acceptable ammonium salts thereof, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_5R_5$, —$NHCOR_4$, —$OR_4$, —$SR_4$, —$COOR_4$, —$COR_4$, and —$CH_2OH$ or X and together define an alkylenedioxy group selected from the group consisting of a methylenedioxy group of formula —$OCH_2O$— and an ethylenedioxy group of formula —$OCH_2CH_2O$—, wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, and wherein n, $R_1$, $R_2$, $R_4$, and $R_5$ as defined in claim 1.

38. A compound as defined in claim 37, wherein $R_1$ is iso-butyl.

39. A compound as defined in claim 38, wherein n is 4.

40. A compound as defined in claim 39, wherein $R_2$ is selected from the group consisting of $CH_3O$—CO, $(CH_3)_2N$—CO, 3-pyridyl-CO, 4-pyridyl-CO and 4-morpholinyl-CO.

41. A compound as defined in claim 40, wherein, X is 4-$NH_2$, Y is H, X' is H and Y' is H.

42. A compound as defined in claim 40, wherein, X is 3-$NH_2$, Y is 4-F, X' is H and Y' is H.

43. A compound as defined in claim 40, wherein, X is 4-$NH_2$, Y is 3-F, X' is H and Y' is H.

44. A compound as defined in claim 39, wherein X is 4-$NH_2$, Y is H, X' is H, Y' is H and $R_2$ is $(CH_3)_2N$—CO.

45. A compound as defined in claim 44, wherein the naphthyl group is a naphthyl-2-$CH_2$ group.

46. A compound of formula IIc

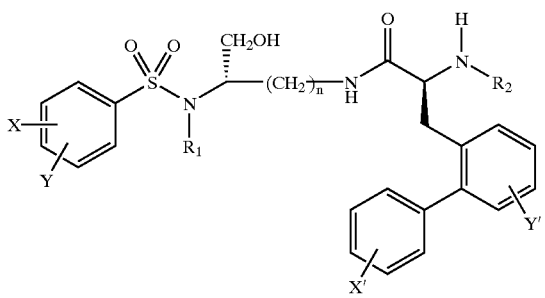

and when the compound of formula IIc comprises an amino group, pharmaceutically acceptable ammonium salts thereof, wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$ and —$CH_2OH$ or X and Y together define an alkylenedioxy group selected from the group consisting of a methylenedioxy group of formula —$OCH_2O$— and an ethylenedioxy group of formula —$OCH_2CH_2O$—, wherein X' and Y', same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_4R_5$, —$NHCOR_4$, —$OR_4$, —$SR_4$, —$COOR_4$, —$COR_4$ and —$CH_2OH$, and wherein n, $R_1$, $R_2$, $R_4$, and $R_5$ are as defined in claim 1.

47. A compound as defined in claim 46, wherein $R_1$ is iso-butyl.

48. A compound as defined in claim 47, wherein n is 4.

49. A compound as defined in claim 48, wherein $R_2$ is selected from the group consisting of $CH_3O$—CO, $(CH_3)_2N$—CO, 3-pyridyl-CO, 4-pyridyl-CO and 4-morpholine-CO.

50. A compound as defined in claim 49, wherein, X is 4-$NH_2$, Y is H, X' is H and Y' is H.

51. A compound as defined in claim 49, wherein, X is 3-$NH_2$, Y is 4-F, X' is H and Y' is H.

52. A compound as defined in claim 49, wherein, X is 4-$NH_2$, Y is 3-F, X' is H and Y' is H.

53. A pharmaceutical composition comprising a pharmaceutically acceptable carrier and at least one compound as defined in claim 1.

54. A pharmaceutical composition comprising a pharmaceutically acceptable carrier and at least one compound as defined in claim 2.

55. A pharmaceutical composition comprising a pharmaceutically acceptable carrier and a compound as defined in claim 30.

56. A pharmaceutical composition comprising a pharmaceutically acceptable carrier and a compound as defined in claim 31.

57. A pharmaceutical composition comprising a pharmaceutically acceptable carrier and a compound as defined in claim 32.

58. A pharmaceutical composition comprising a pharmaceutically acceptable carrier and a compound as defined in claim 33.

59. A pharmaceutical composition comprising a pharmaceutically acceptable carrier and a compound as defined in claim 34.

60. A pharmaceutical composition comprising a pharmaceutically acceptable carrier and a compound as defined in claim 35.

61. A pharmaceutical composition comprising a pharmaceutically acceptable carrier and a compound as defined in claim 36.

62. A pharmaceutical composition comprising a pharmaceutically acceptable carrier and a compound as defined in claim 45.

* * * * *